United States Patent [19]
Prince et al.

[11] Patent Number: 5,348,519
[45] Date of Patent: Sep. 20, 1994

[54] EXERCISE AND DIAGNOSTIC APPARATUS AND METHOD

[75] Inventors: Jeffrey T. Prince, Grass Valley; Robert L. Rawls, Davis; Philip T. Dempster, St. Helena; Jody Ono, Davis, all of Calif.

[73] Assignee: Loredan Biomedical, Inc., West Sacramento, Calif.

[21] Appl. No.: 934,293

[22] Filed: Aug. 24, 1992

Related U.S. Application Data

[63] Continuation of Ser. No. 478,098, Feb. 9, 1990, abandoned, which is a continuation-in-part of Ser. No. 152,259, Feb. 4, 1988, abandoned.

[51] Int. Cl.$^5$ ............................................. A63B 21/005
[52] U.S. Cl. ............................................. 482/6; 482/4; 482/901; 482/903; 73/379.01; 364/413.02; 364/551.01; 414/744.3
[58] Field of Search .................. 482/1, 4–8, 482/51, 900–903; 128/25 R; 73/379.01–379.03, 379.06, 379.08; 254/266, 270, 335, 336, 358, 362; 364/413.02, 413.27, 551.01; 901/17, 46; 414/744.3, 744.6

[56] References Cited

U.S. PATENT DOCUMENTS

| | | | |
|---|---|---|---|
| 3,465,592 | 9/1969 | Perrine | 73/379 |
| 3,760,956 | 9/1973 | Burch | 414/744.03 |
| 4,235,437 | 11/1980 | Ruis et al. | 272/134 |
| 4,652,204 | 3/1987 | Arnett | 901/17 X |
| 4,822,037 | 4/1989 | Makansi et al. | 272/129 |
| 4,848,152 | 7/1989 | Pratt, Jr. | 272/129 X |
| 4,882,677 | 11/1989 | Curran | 73/379 X |
| 4,907,797 | 3/1990 | Gezari et al. | 272/129 |

OTHER PUBLICATIONS

"Ergometer Brochure" by Ergometrics, Inc., 1986.

*Primary Examiner*—Richard J. Apley
*Assistant Examiner*—Joe H. Cheng
*Attorney, Agent, or Firm*—Townsend and Townsend Khourie and Crew

[57] ABSTRACT

A horizontal support arm is mounted for upward and downward movement on a vertical support column. An interface unit having an actual mass value is disposed on a free end of the horizontal support arm and is adapted to be grasped and lifted by a human subject. A simulated mass value independent of said actual mass value may be set for the interface unit, and the amount of vertical force exerted by the human subject upon the interface unit is measured. An exercise control unit provides for controlled vertical movement of the interface unit as a function of the simulated mass value such that the interface unit responds to a lifting force by the human subject in a manner that simulates the inertia of an object having a mass value equal to the simulated mass value in a gravitational field.

64 Claims, 31 Drawing Sheets

EXERCISE AND DIAGNOSTIC APPARATUS AND METHOD

CROSS REFERENCE TO RELATED APPLICATIONS

This is a continuation of application Ser. No. 07/478,098 filed Feb. 9, 1990, now abandoned, which is a continuation-in-part of application Ser. No. 07/152,259 filed Feb. 4, 1988, now abandoned.

FIELD OF THE INVENTION

This invention relates generally to systems for testing and improving human performance and more specifically to systems for lift task exercise and diagnosis.

BACKGROUND OF THE INVENTION

Prior Art Cable and Reel Systems

Prior art lift task exercise systems which employ a cable and cable reel system for controlling the exercise motion typically have a fixed cable outlet point. A cable reel with a cable carried thereon extends through an exit point in a floor mat with the free end of the cable attached to a human interface mechanism which is typically a handle or a pair of handles separated by a bar. A resisting system for driving and/or resisting rotation of the cable reel may be either a passive isokinetic type of accommodating resistance mechanism or it may be an active servo motor drive and control system. In the case of a passive resistance system, a separate mechanism is required for returning the cable to the lowered position. In the latter case, the active system can reel in the cable.

Prior art systems of this type have limited capability of accurately measuring and controlling lift task parameters such as cable tension to imitate a real life lifting task. They are accurate only if the movement of the handle is in a substantially vertical direction. In other words, cable tension is only equivalent to a free weight being lifted if the cable is maintained in a substantially true vertical orientation.

When the cable direction is substantially altered from the vertical direction, the cable tension resolves into a vertical component corresponding to perceived "box" weight and a horizontal component perceived by the person as a sideways movement restraint. The person will thus sense that the handle is tethered to a fixed point on the platform and is not only resisting the lift of the handle but also the forward movement thereof. Thus this type of prior art system is incapable of accurately imitating a typical real life lift task of picking up a weighted box and setting it on a shelf. The change in orientation of the cable as the handle is moved forward to set it on a shelf produces change in the perceived "box" weight and places other forces on the person that are not the same as lifting and placing an actual weighted box on the shelf.

The resisting system of the prior art also do not control cable tension in a way that imitates the inertial effects of accelerated motion of the "box." Typically, isokinetic resistance is offered to movement of the handle and this does not simulate the forces actually experienced by the muscle and bone structure of a person as they lift a box. Box is used in quotes here, because the system of the prior art also do not use an actual box as the human interface mechanism and thus do not simulate the aspect of a lift task that involves the actual positioning of hands and fingers thereon around the type of object that is actually used in the lift task being simulated.

The prior art systems are thus unable to simulate accurately the actual lift tasks that workers perform. They are not capable of providing a basis for accurately assessing the capability of a worker to do particular lifting and placing tasks. Furthermore they do not provide a basis for accurately training persons in performing a variety of lift tasks.

An additional disadvantage with this type of prior art system is that the fixed cable outlet point can interfere with the natural movement of the feet of the person performing the lift task and could in some circumstances create a tripping hazard.

Lever Systems

Other lift task system in the prior art use a long lever arm attached to the head of a dynamometer with some type of mechanical constraint to produce a lifting motion that is of greater or lesser accuracy depending on the nature of the mechanism. These systems are even less capable of accurately imitating actual workplace lift tasks than prior art cable and reel lift task systems.

The cable and reel lift task apparatus in the parent application referred to above had many advantages over the prior art systems and implemented a version of a gravity/inertial control mode which simulated a real life lift task. However, certain control difficulties are present in that system and further improvements are needed for a system to be fully satisfactory for commercialization of the inventions involved.

It is thus apparent that there is a definite need in the art for an improved lift task system that is capable of imitating lift tasks in an accurate manner so that accurate diagnosis and training of lifting abilities can be accomplished.

OBJECTS OF THIS INVENTION

It is the principal object of this invention to provide an improved lift task exercise and diagnostic system.

It is another object of this invention to provide an improved lift task system with three degrees of freedom of movement of the patient attachment.

It is another object of this invention to provide a lift task system that is capable of accurately simulating a variety of real life lift task challenges and operating parameteres thereof.

It is a specific object of this invention to provide a lift task system of the type in which the patient interface device is free to move throughout a substantial working area in a horizontal plane while maintaining accurate control of simulated weight and inertia of the interface device.

FEATURES AND ADVANTAGES OF THE INVENTION

One aspect of this invention features a method for controlling the performance of a lift task by a human subject using an interface means adapted to be grasped and lifted by the human subject with the method involving the steps of:

a. presetting a simulated mass value for the interface means;

b. measuring the amount of vertical force exerted on the interface means by the human subject; and c. controlling the vertical movement of the interface means in accordance with a prearranged function of the simulated mass value and the amount of vertical force such that the interface means responds to the vertical force in a manner that simulates substantially the inertia of a body having the simulated mass value in a gravitational field.

The method of this invention provides for the first time the ability to simulate a real world lift task by providing the same intertial response for an interface device that a real mass of the same weight and inertia would have. This enables new testing modalities to be performed in the occupational medicine and physical therapy fields.

Another feature of the method of this invention is preferably carried out in apparatus in which the interface means comprises an attachment member of predetermined geometry adapted to be grasped and lifted by a human subject, a horizontal mounting arm means carrying the box member on one end thereof, and vertical mounting means for mounting the horizontal mounting arm for bidirectional vertical movement and for rotational movement in a horizontal plane, the system further comprising an obstruction of known geometry and position which may interfere with free vertical movement of the attachment member when moved into proximal relation thereto. In this case the method of this invention further comprises the steps of:

determining the borders of a safe working envelope for the attachment member from the predetermined geometry thereof and the known geometry and position of the obstruction expressed in terms of vertical and rotational coordinate positions of the mounting arm;

measuring the vertical coordinate position of the mounting arm;

measuring the rotational coordinate position of the mounting arm;

and wherein the controlling step includes the steps of:

examining the measured vertical and horizontal coordinate positions to indicate when the interface means is outside the border of the safe working envelope; and stopping vertical movement of the interface means until the interface means is moved to a vertical and rotational coordinate position within the safe working envelope.

The method of this invention thus provides the advantage of safe operation by precluding vertical movement of the interface means when the boundaries of a safe working envelope are violated.

Another feature of the method of this invention involves application of the method in apparatus in which the interface means comprises a box member of predetermined box geometry adapted to be grasped and lifted by a human subject, a horizontal arm means carries the box member on one end thereof, and a vertical mounting means mounts the horizontal arm means for bidirectional vertical movement and for rotational movement in a horizontal plane, the system further comprising shelf means of predetermined shelf geometry and mounted in a predetermined shelf location such that the lift task may comprise placing the box member on the shelf means. In this case the method further comprises the steps of:

measuring the vertical coordinate position of the mounting arm;

measuring the rotational coordinate position of the mounting arm;

and wherein the controlling step includes the steps of:

determining from the measured vertical and rotational coordinate positions when the box member is in a predetermined position above the shelf means;

controlling the downward movement of the box member onto the shelf to decelerate the movement of the box member as the box member approaches the shelf means.

The feature of the method of this invention which permits controlled placement of a box type of interface onto a shelf further facilitates real world lift task simulation since lifting a box from the floor and placing it on a shelf is a typical manual lifting task in many occupations.

Another feature of the method of this invention is realized when the method is carried out in apparatus in which the interface means comrises an attachment member of unknown mass adapted to be grasped and lifted by a human subject, a horizontal arm means carries the attachment member on one end thereof and includes load cell means for measuring the vertical force applied by the attachment member to the horizontal arm means and acceleration measuring means for measuring the vertical acceleration of the horizontal arm means, a vertical mounting means mounts the horizontal arm means for bidirectional vertical movement, and a motor drive means actively drives the vertical mounting means in bidirectional vertical movement. In this case the method step b. described above comprises the steps of:

b.1. performing an attachment member weight and inertia calibration prior to performance of a lift task exercise by the human subject, including the steps of:

b.1.1. recording the output of the load cell means when the attachment member is being acted on only by earth gravitational forces as a member weight value;

b.1.2. controlling the motor drive means to move the attachment member through a pattern of different acceleration values;

b.1.3. recording the outputs of the load cell means and the acceleration measuring means during the step b.1.2. and b.1.4. determining from the recorded outputs obtained in step b.1.3. an inertial calibration value which accurately correlates measured output of the load cell means due to inertia of the attachment member under conditions of acceleration and measured output of the acceleration measuring means;

and b.2. determining the amount of vertical force exerted on the attachment member by a human subject during a lift task exercise by performing the steps of:

b.2.1. repeatedly reading and recording the outputs of the load cell means and the acceleration measuring means; and b.2.2. after each reading and recording performed in step b.2.1., calculating the human subject applied force as the load cell output less the member weight value determined in step b.1.1 less the product of the inertial calibration value determined in step b.1.4 and the output of the acceleration measuring means.

The feature of being able to determine the actual force applied by the human subject to the interface device permits more accurate control of the vertical movement of the lift task system in various operating modes and more accurate measurement of the lifting capabilities of the subject.

Another aspect of this invention features apparatus for performing a lift task which combines the following elements:

interface means adapted to be grasped and lifted by a human subject and having an actual mass value;

means for setting a simulated mass value for the interface means independent of the actual mass value thereof;

force measuring means for measuring the value of vertical force exerted by the human subject upon the interface means;

exercise control means coupled to the interface means for providing a controlled vertical movement thereof, including means responsive to the force measuring means for controlling the vertical movement of the interface means as a function of the simulated mass value such that the interface means responds to a lifting force by the human subject in a manner that simulates the inertia of an object having a mass value equal to the simulated mass value in a gravitational field.

In a preferred embodiment of this apparatus the interface means has an unknown mass; and further comprises horizontal arm means for carrying the interface means on a free end thereof; and vertical transport means for transporting the horizontal arm means in upward and downward motion, including transmission means coupled to the servo motor drive means such that the servo control means, the servo motor drive means and the transmission means cooperatively control the upward and downward movement of the horizontal arm means. In this embodiment, the force measuring means comprises:

load measuring means coupled between the horizontal arm means and the interface means for measuring the total vertical force applied to the arm means by the interface means, acceleration measuring means mounted on the horizontal arm means for measuring the actual vertical acceleration of the horizontal arm means and the interface means;

weight calibration means operatively associated with the servo control means for positioning the interface means with only its mass exerting force on the load measuring means and for recording the output of the load measuring means as an Actual Mass Value of the interface means;

inertia calibration means operatively associated with the servo control means for driving the servo motor means to move the horizontal arm means through a predetermined pattern of different acceleration values, for recording a sequence of outputs of the load measuring means and associated outputs of the acceleration measuring means, and for calculating from the recorded sequence of outputs an Inertia Calibration Factor which correlates acceleration values with load values; and force calculating means operative when a human subject is applying force to the interface means to calculate the actual force applied by the human subject as a predetermined function of the current output of the load measuring means, the Acutal Mass Value, the current output of the acceleration measuring means and the Inertia Calibration Factor.

This invention thus has the advantage of being able accurately to simulate real world lift task and accurately measure the force applied by the suject by subtracting out the weight of the interface device and the inertial force produced by its acceleration in a gravitational field. This permits the interface device to simulate a mass of selected weight independent of the acutal mass thereof for facile control over the parameters of a particular lift task. This is especially important in the gravity/inertia mode where the apparatus is capable of simulating the lifting of a box or other object with a selected mass independent of the actual mass of the box being lifted. Both feel and inertial response of a heavier object are reproduced.

Another aspect of this invention features apparatus for performing a lift task which includes horizontal arm means, a vertical support means and a carriage means mounted on the vertical support means for carrying the horizontal arm means for vertical upward and downward movement. A transmission means is coupled to the carriage means for driving the carriage means in the upward and downward movement. A servo motor means is coupled to the transmission means for powering the transmission means to drive the carriage means, and a servo control means is coupled to the servo motor means for controlling the operation of the servo motor means in driving the transmission means. A load measuring means is mounted on a free end of the horizontal arm means and an acceleration measuring means is mounted on the horizontal arm means for measuring the vertical acceleration thereof and producing an output acceleration signal communicated to the servo control means. An interface means is coupled to the load measuring means for enabling a human subject to apply vertical force to the horizontal arm through the load measuring means. The load measuring means is operative to measure the amount of vertical force applied thereto and produces an output force signal communicated to the servo control means. The servo control means controls the servo motor means for driving the transmission means as a prearranged function of a preselected lift task control mode and associated control mode parameters including a simulated mass value for the interface means, the force signal and the acceleration signal.

Preferably, the servo control means includes a programmed digital computer control means which comprises central processor means, converter means for converting the output acceleration signal and the output force signal from analog to digital signal values for input to the central processor means at a preselected data acquisiton rate, and control program means for operating the central processor means. The control program preferably includes an interface calibration module operative during a calibration interval prior to operation of the apparatus in the preselected lift task control mode and a velocity command calculating module for calculating a velocity command value to supply to the servo motor control means during operation of the apparatus in the preselected lift task control mode. The interface calibration module includes the following elements:

means for storing as an Interface Weight parameter the digital signal value corresponding to the force signal when the interface means is being acted on only by earth gravitational forces, means for controlling the servo motor means during an inertial calibration interval prior to performing a lift exercise task to move the interface means through a pattern of different acceleration values, means for storing the associated digital signal values corresponding to the output force signal and the output acceleration signal during the inertial calibration interval, and means for analyzing the stored associated digital signal values to determine an Inertial Calibration Factor which translates an acceleration signal value into a corresponding inertial force value due to acceleration applied to the interface means.

The velocity command calculation module preferably includes the following elements:

means for inputting and storing Set Mass and a Set Threshold Force parameter values associated with inertia and weight of an object to be simulated as the object to be lifted by a human subject;

means for reading and storing the digital signal value corresponding to the output force signal as a Lift Force parameter value and for reading and storing the digital signal value corresponding to the output acceleration signal as a Current Acceleration parameter value, means for calculating a Force parameter as the actual force being applied by a human subject to the interface means as a predetermined function of the Lift Force parameter, the Interface Weight Parameter, the Current Acceleration parameter, and the Inertial Calibration Factor, means for calculating a simulated Net Force applied to the interface means as a function of the Force parameter and the Set Threshold Force parameter, means for calculating a Velocity Change parameter as a function of the Net Force parameter and the Set Mass parameter, and means for calculating and storing a new Velocity Command parameter as a function of the currently stored Velocity Command parameter and the Velocity Change paramter.

It will be readily appreciated that the apparatus of this invention thus provides sophisticated computer control of a lift task exercise system which is readily programmable to perform various lift task simulations in a faithful manner.

Other objects, features and advantages of this invention will be apparaent from a consideration of the detained description given below in conjunction with the accompanying drawings.

BRIEF DESCRIPTION OF THE DRAWING FIGURES

FIG. 14 is a partial perspective view of one end of an assembled combination of the fixed arm subassembly of FIG. 12 and the moving arm subassembly of FIG. 13.

DETAILED DISCLOSURE OF PREFERRED EMBODIMENTS

Figure 1:
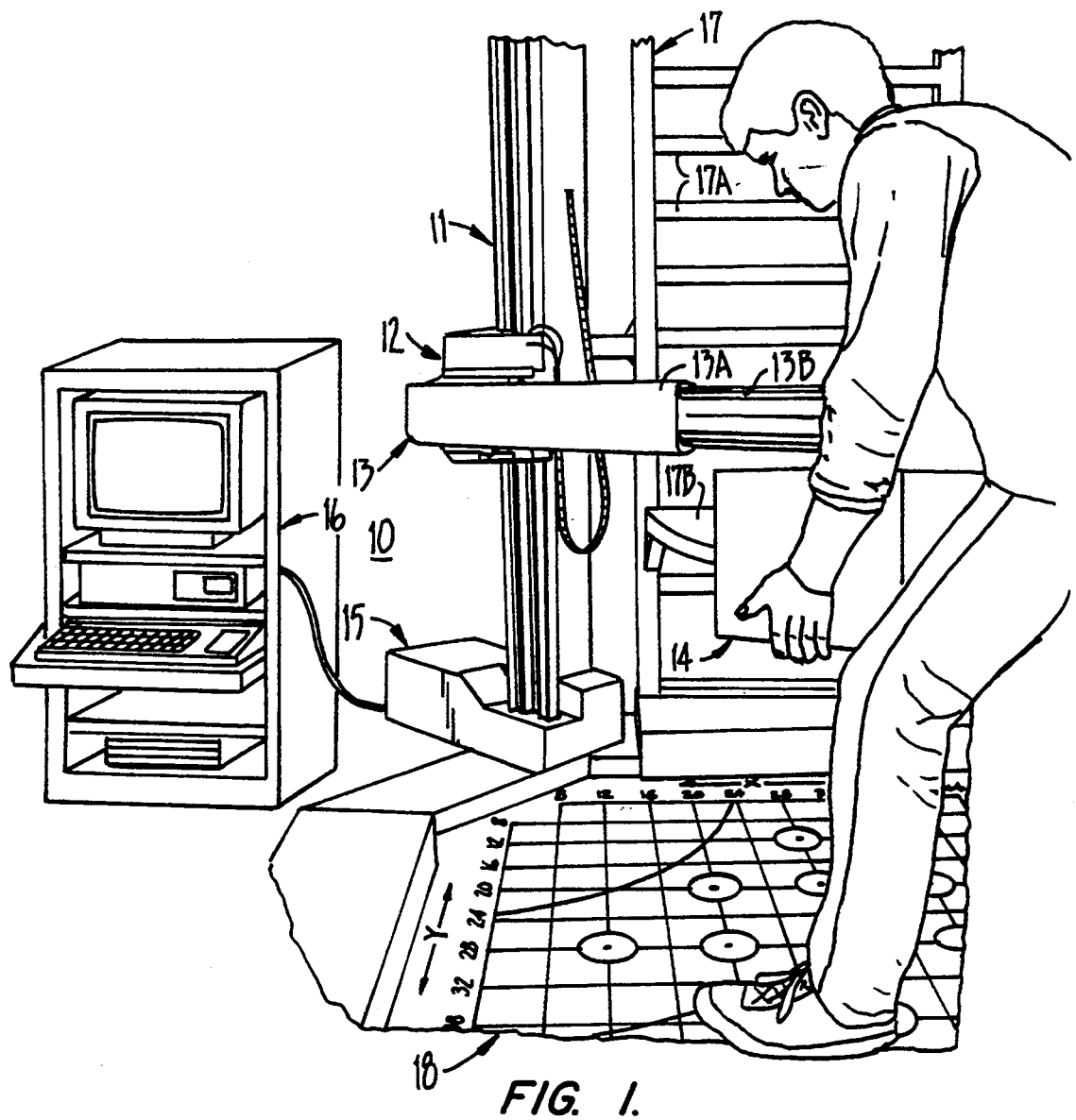
FIG. 1 is a pictorial view of components of a lift task apparatus in accordance with this invention.

Lift Task System and Major Components (FIGS. 1-4)

FIGS. 1 through 4 illustrate the major components of a lift task system 10 in accordance with this invention. A vertical support column assembly 11 carries a carriage and hinge assembly 12 thereon and provides a z-axis component of movement in a cylindrical coordinate system. Carriage and hinge assembly 12 carries a telescoping arm assembly 13 thereon and provides an angle (Theta) component of movement. Telescoping arm assembly 13 includes a first arm subassembly 13A and a second, telescoping arm subassembly 13B carried thereon. First arm subassembly 13A rotates in a horizontal plane and second arm assembly translates in and out relative to the first arm subassembly to provide a radius component of movement. A box 14 or other patient interface device is carried on a free end of second arm subaassembly 13B. With this overall arrangement of components, box 14 can be moved simultanously in all three component directions of a cylindrical coordinate system.

A drive and controller assembly 15 is coupled to a continuous belt transmission arrangement in vertical support column assembly 11 actively to drive carriage and hinge assembly 12 along the z-axis. A host computer arrangement 16 is coupled to a microprocessor based controller in drive and controller assembly 15 which also preferably includes a servo motor drive arrangement. Host computer 16 operates in accordance with a host software program to provide functions such as lift task mode selection, test parameter entry, data collection and realtime display, patient biofeedback display, test result calculations and printouts, and communication of commands and test parameters to the microprocessor based controller. This arrangement will be discussed in more detail below.

A shelf and bracket assembly is also included in the lift task system 10 and includes a plurality of spaced shelf brackets 17A on which a shelf 17B may be selectably mounted. This shelf arrangement, together with the three component motion arrangement for box 14 permits simulation of a lift task involving picking up a box from the floor and placing it on a shelf at a selected height above the floor. A foot mat arrangement 18 may also be provided with the system and, as shown, may include a calibrated grid for entering and duplicating foot positions, together with prepositioned and numbered foot position locations which have known coordinates and can be entered as position numbers.

Patient Interface Attachments

Figure 2:
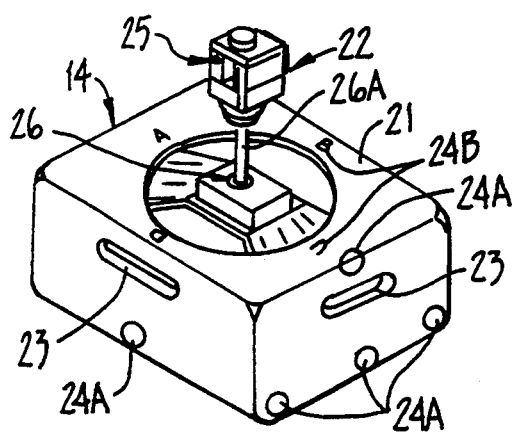
FIGS. 2-4 are perspective views of various patient interface attachments for a lift task apparatus in accordance with this invention.
Figure 3:
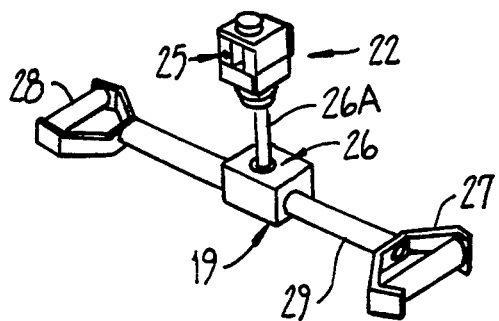
Figure 4:
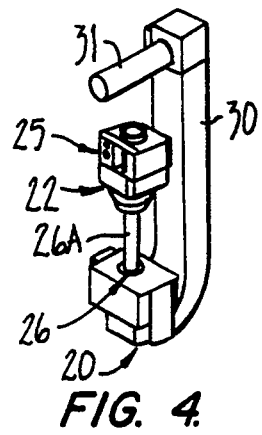

FIGS. 2–4 illustrate various types of patient interface attachments that may be included in the overall lift task system 10. FIG. 2 illustrates in more detail attachment 14 that simulates a box. One or more box type attachments of varying size and configuration may be supplied with the system. FIG. 3 illustrates a T-handle type of attachment 19 which permits set up of different handle widths and hand positions. A stirrup attachment 20 as shown in FIG. 4 may be provided for single handed lift task simulation. Each of these three types of attachment devices includes a coupler arrangement 22 for mounting the device on the free end of arm subassembly 13B as depicted more completely in FIGS. 14, 15, and 17 and described below. An attachment coding arrangement 25 is included in the coupler arrangements 22 for cooperating with a sensor arrangement on arm subassembly 13B for signalling the type of attachment to the controller in controller and drive arrangement 15.

All three attachements also include a ball-swivel type bracket and post mounting assembly 26 that permits both tilting and rotation of the box or handles relative to post 26A. The combination of this swivel mounting arrangement and the three components of movement of the free end of arm subassembly 13B provide a patient interface that has the feel of lifting and moving about with a box without mechanical constraint except for the weight and inertia which is simulated by the system drive and control in a manner discussed in more detail below.

Box Simulation Attachment (FIG. 2)

Box attachment 14 preferably comprises a hollow box element 21 with hand grip cutouts 23 formed in each of the four sides thereof. Color coded box holding position markings 24A and box orientation labels 24B may be provided on box element 21 for registering the box orientation and symmetric or asymmetric hand grip positions used in a particular lift task. These coding arrangement facilitate set up and duplication of lift tasks from one testing or exercise bout to the next and provision is made in the test parameter entry modules in host computer 16 for entry of this information.

T-Bar Handle Attachment (FIG. 3)

In this type of patient interface or attachment device a pair of handles 27, 28 are mounted at the end of an elongeated bar 29, preferably using a mounting arrangement which permits rotation of each handle relative to the axis of bar 29. By providing either a telescoping arrangement for bar 29 or by using bars of different lengths, a variety of customized handle widths and hand positions can be simulated for various types of lift tasks. Provision is preferably made in the parameter entry program modules running in host computer 16 for entering data on these custom positions for purposes of replication of the same task at a later time in a testing or rehabilitation mode and for collection of comparative data from one patient to another in a research mode.

Stirrup Attachment (FIG. 4)

Stirrup attachment 20 includes a single handle 31 which is preferably mounted in rotatable fashion to a bracket arrangement 0 so that the handle 31 is positioned directly above the point of attachment of the coupler assembly 25 to the free end of arm subassembly 13B.

Lift Task System Variations

It should be apparent from the description of the lift task system embodiment of FIGS. 1–4 that many variations of the system could be implemented to produce different embodiments of the invention with less or different features. For example, arm assembly 13 could be altered to eliminate any telescoping feature. This would restrict the working envelope of the system but still furnish lift task simulation of greater variety than prior art systems. In this more limited embodiment, a shelf arrangement could still be used and a box could be placed on the shelf by a lifting and swinging motion restricted to a single circular arc.

Rotation of arm assembly 13 on carriage assembly 12 could be eliminated, which would further restrict lift task simulation but still provide improvement over some prior art systems in the area of control of lift task modes and models. Shelf arrangements could not be employed with such an embodiment.

A variety of changes in the patient interface attachments could be made by removing some of the degrees of freedom of movement. Each of these changes reduces the performance of the overall system relative to the preferred embodiment but would still be useful under some conditions.

Additional types of patient interface attachments could be included to simulate the shapes of other types of loads. For example a hollow cylindrical object might be provided to simulate barrels or paper rolls.

In addition to providing embodiments of this invention with reduced functional features, it should be apparent that features could be added to the preferred embodiment. For example, electrically operated brake mechanisms might be added to each of the carriage and hinge assembly 12 and the arm assembly 13. The brake associated with the carriage and hinge assembly would slow or stop further angular rotation of the arm and the brake associated with the arm assembly would slow or stop further radial movement of the box or other attachment. This added movement control capability could be used in connection with the collision avoidance software routines to preclude moving the patient attachment and arm outside of a safe working envelope.

It is also conceivable that small servo motor drive and control mechanisms might be added to control the angular movement of the arm assembly and/or the radial movement of the movable arm subassembly relative to the fixed arm subassembly so that two dimensional or a full three dimensional control over movements would be achieved.

Figure 5:
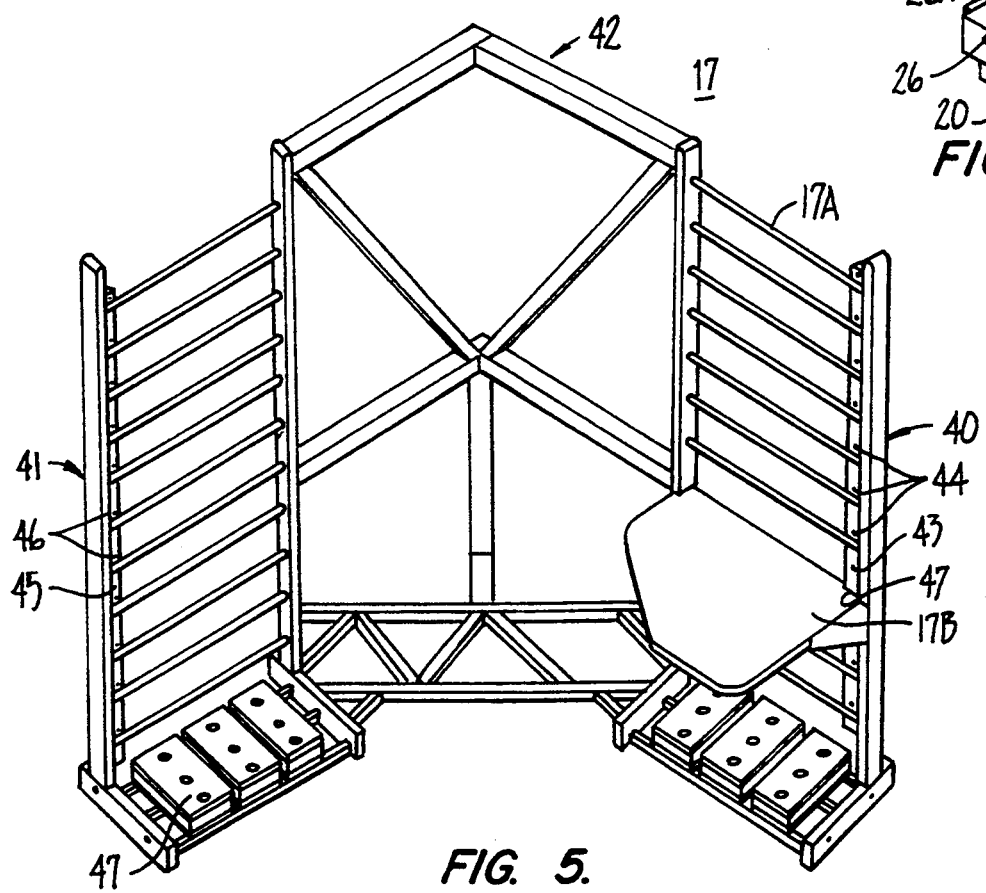
FIG. 5 is a perspective view of a shelf and shelf bracket arrangement for a lift task apparatus in accordance with this invention.

Shelf Bracket and Shelf Assembly (FIG. 5)

Shelf bracket and shelf assembly 17 is depicted in greater detail in FIG. 5. The overall assembly 17 includes a right hand shelf bracket section 40, a left hand shelf bracket assembly 41, a central support section 42, a right hand shelf 17B, and a left hand shelf (not shown) which is like the right hand shelf with a mirror image configuration of the shelf top. Shelf 17B includes a lockout section 47 which cooperates with a sensor mounting bracket 43 to prevent a left hand shelf from being placed on one of the right hand bracket locations and vice versa for the left hand shelf.

A magnet is mounted on the back wall of this lockout area and cooperates with a magnet sensing switch 44 at each shelf bracket position to signal when a shelf is on a particular bracket. The outputs of these switches are polled by the controller during operation of the system to keep track of the operating conditions of the system as part of a shelf collision avoidance feature of the system. A similar sensor mounting bracket 45 and arrangement of sensors 46 is provided in connection with the left hand shelf bracket arrangement 41.

A series of weights 47 are positioned on the foot of each of the shelf bracket sections 40 and 41 for stability. These foot sections are covered with appropriately formed cover sections in the finished installation. Preferably the right and left hand shelf bracket sections are formed as separate assemblies which bolt to the central support assembly 42 for ease of shipping and handling.

The vertical support column assembly 12 is mounted between the right and left hand shelf bracket assemblies and fastened to the central support assembly struts in an convenient manner (not shown).

Figure 8:
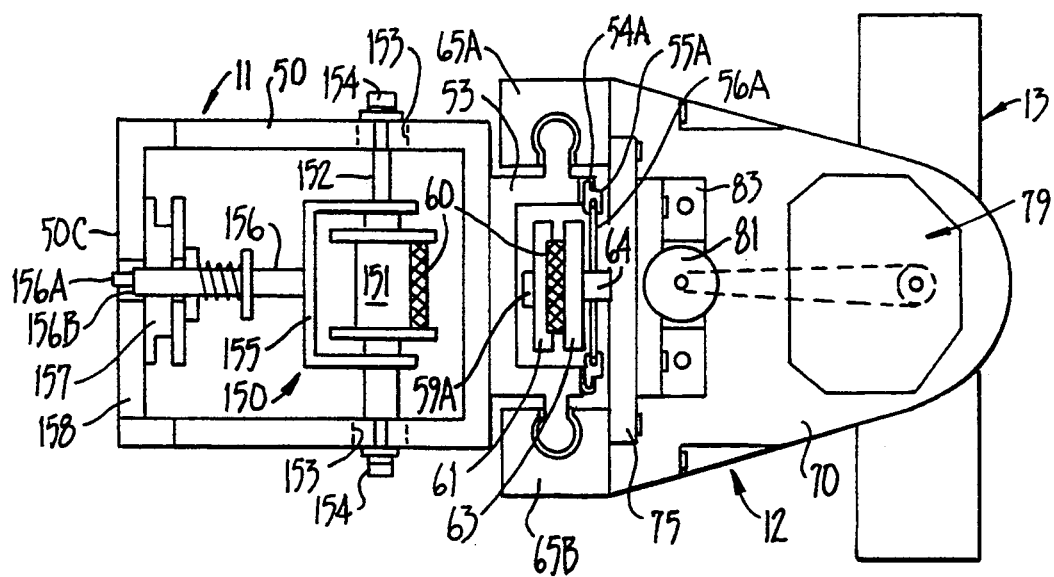
FIG. 8 is a partly sectioned view of a support column and drive arrangement and an associate carriage and hinge arrangement in accordance with this invention.
Figure 6:
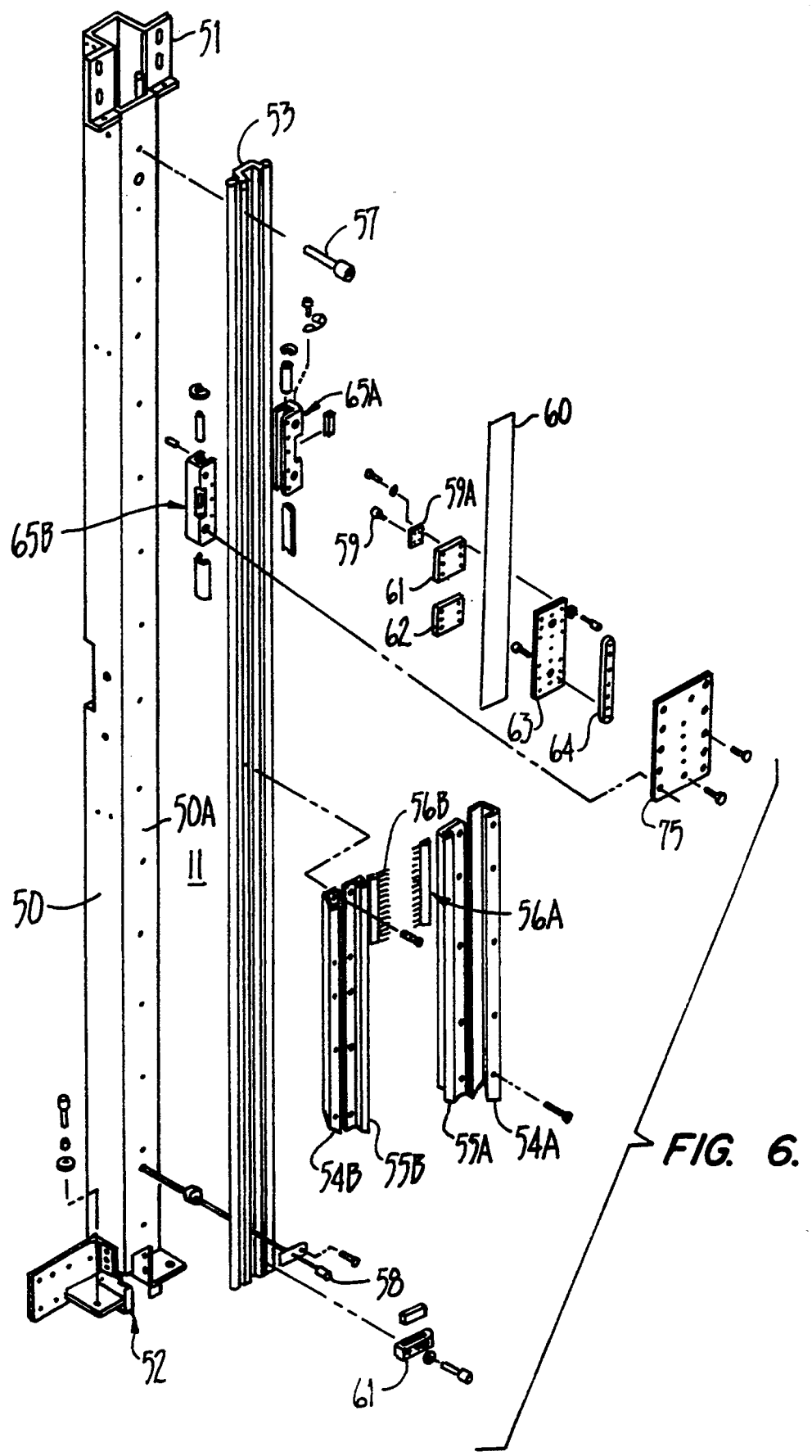
FIG. 6 is an exploded perspective view of a support column, carriage track and belt drive arrangement in accordance with this invention.

Vertical Support Column Assembly (FIGS. 6 and 8)

The major components of vertical support column assembly 11 are illustrated in the exploded view of FIG. 6. A hollow box member 50 has a upper belt reel mounting bracket 51 on a top end thereof and a lower belt reel mounting bracket arrangement 52 on a bottom end thereof. An elongated dual rail asssembly 53 is bolted to wall 50A and serves as the guide rails for a linear ball bearing arrangement 65 on which carriage and hinge assembly 12 is mounted. Only the carriage tie plate 75 of carriage and hinge assembly is shown in FIG. 6 for purposes of correlation with the elements thereof shown in exploded perspective in FIG. 7.

Mounting plate 75 is bolted to the two linear bearings 65A and 65B. Continuous drive belt 60 is mounted to mounting plate 75 using a pair of toothed back clamp elements 61 and 62 and a front clamp element 63 bolted to the two back clamp elements and a spacer plate 64 which is bolted both to front clamp element 63 and carriage tie plate 75. A hall effect magnet 59 is mounted on a carriage stop block 59A which is fastened to the back of belt clamp element 61. This Hall effect magnet cooperates with an upper hall effect sensor 57 mounted at an upper limit position on rail assembly 53 and a lower hall effect sensor 58 mounted at a lower limit position on rail assembly 53 to signal when the carriage is at the upper or lower limit of permitted vertical travel respectively.

A hard stop block 61 is mounted below the mounting position of lower hal effect sensor 58 and cooperates with carriage stop block 59A to provide a hard structural/mechanical stop for the carriage assembly at maximum lower limit of travel.

For both safety and appearance, brush type belt cover assemblies 56A and 56B are mounted to the dual rail assembly 53 using a pair of brush holder extrusions 55A, 55B and brush extrusion mounting brackets 54A, 54B. The section view of FIG. 8 illustrates the arrangement of these components after assembly.

Figure 7:
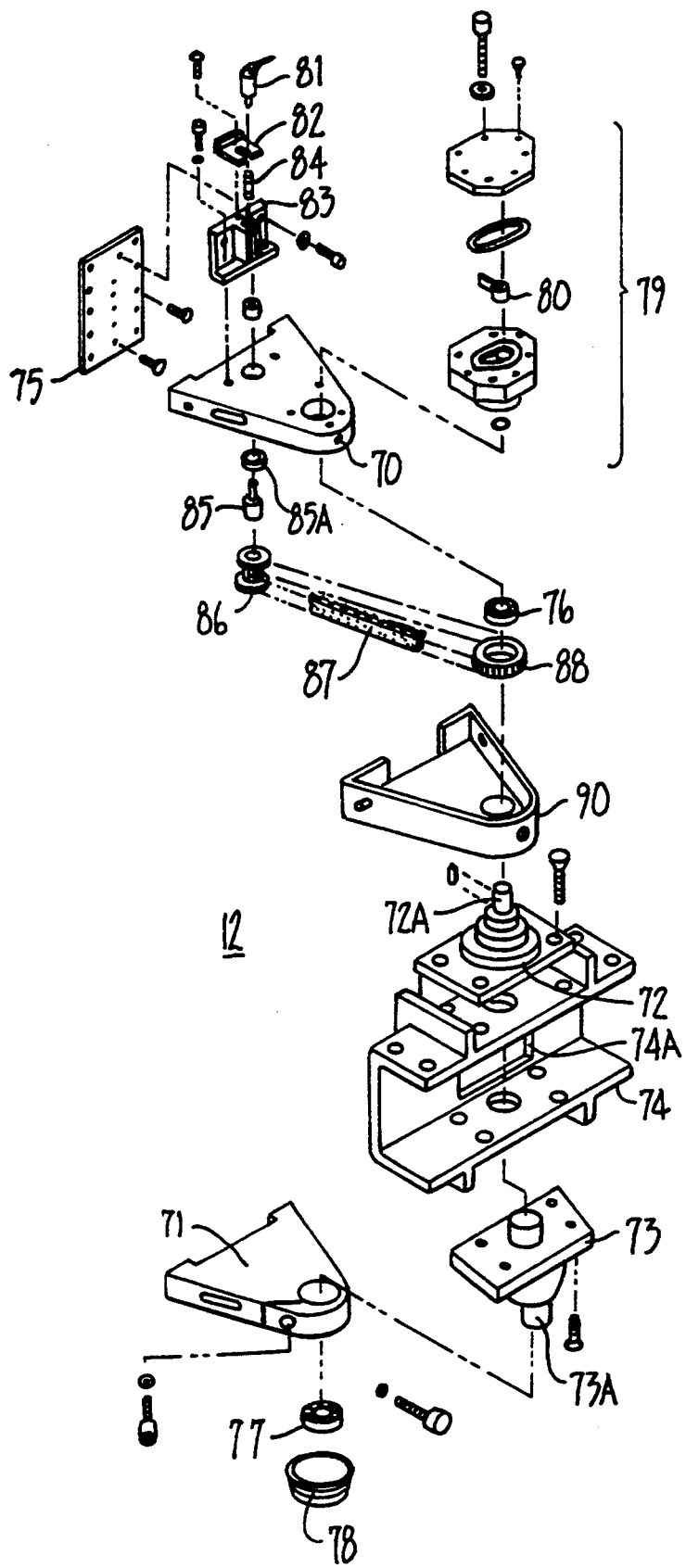
FIG. 7 is an exploded perspective view of a carriage and hinge arrangement in accordance with this invention.

Carriage and Hinge Assembly (FIGS. 7 and 8)

Components of carriage and hinge assembly 12 are illustrated in exploded perspective in FIG. 7. Upper hinge plate 70 and lower hinge plate 71 bolt directly to linear bearing assemblies 65A and 65B as shown generally in FIG. 8. These hinge plates are formed of one inch thick aluminum and provide the main structural support for the carriage and hinge assembly 12. Carriage tie plate 75 also bolts directly to the linear bearing assemblies.

A top hinge pin assembly 72 and a bottom hinge pin assembly 73 are mounted on the top and bottom walls of an arm mouting bracket 74. Pin 72A of top hinge pin assembly 72 is journalled for rotation in a bearing 76 associated with top hinge plate 70. Pin 73A is journalled for rotation in a bearing 77 and bearing housing arrangement associated with bottom hinge plate 71.

A hydraulic damper assembly 79 is mounted on the top wall of upper hinge plate 70 and damper pivot 80 is mounted to the top of pin 72A to rotate therewith and damp the rotation of the arm assembly 13 and arm bracket 74. A rotation sensing potentiometer is mounted on a bracket 82 which is in turn mounted on a pot bracket 83 which is fastened both to upper hinge plate 70 and hinge tie plate 75. A misalignment coupler 84 couples the shaft of potentiometer 81 to shaft 85 which is both journalled for rotation in a bearing 85A and carries thereon a pulley 86 which is turned by a belt driven by a pulley 88 carried on and keyed to hinge pin 72A. Thus potentiometer 81 tracks the Theta position of the arm assembly 13.

A bottom cover 90 covers the belt and pulley drive arrangement. A top cover (not shown) is mounted over the upper hinge plate 70 to cover the potentiometer 81 and the damper assembly 79.

Figure 9:
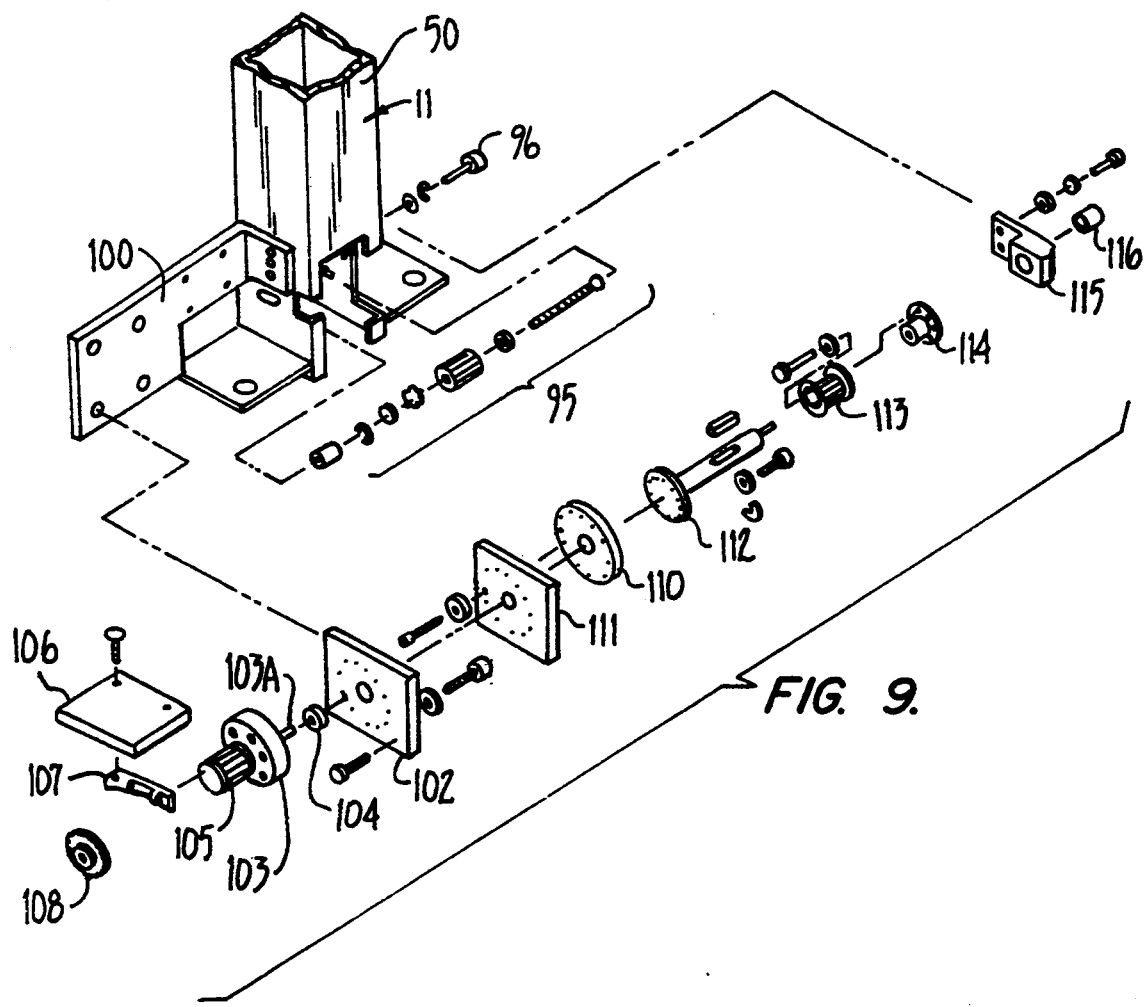
FIG. 9 is an exploded perspective view of a servo motor and drive arrangement useful in connection with this invention.

Motor Drive Assembly and Mounting (FIG. 9)

FIG. 9 illustrates in exploded perspective the components of a motor drive arrangement which is one portion of motor drive and control assembly 15. An idler pulley and shaft arrangement 95 mounts at the bottom end of support column 50 with a mounting bolt 96 at the location shown. Motor mounting bracket 100 is bolted to the bottom of support column 50. A motor support bracket 102 is bolted to motor mounting bracket 100 and servo motor 103 with associated tachometer 105 is bolted thereto with the motor shaft 103A journalled in a companion bearing 104. An optical board 106 mounts over motor 103 on a bracket 107 and together with optical disk 108 carried on the back of the motor and tachometer combination forms an optical position encoder which senses motor shaft rotation and thus measures changes in the position of the carriage and arm assembly.

A cycloidal type of reducer 110 mounts on its own support bracket 111 which is, in turn, mounted to support bracket 100. Reducer 110 is driven by motor shaft 103A and in turn has a drive shaft 112 mounted thereto. Drive pulley 113 is carried on and keyed to drive shaft 112. A tapered bushing 114, a mounting bracket 115 and a companion bearing 116 complete the mounting of the drive shaft and drive pulley to the support column 50.

Figure 10:
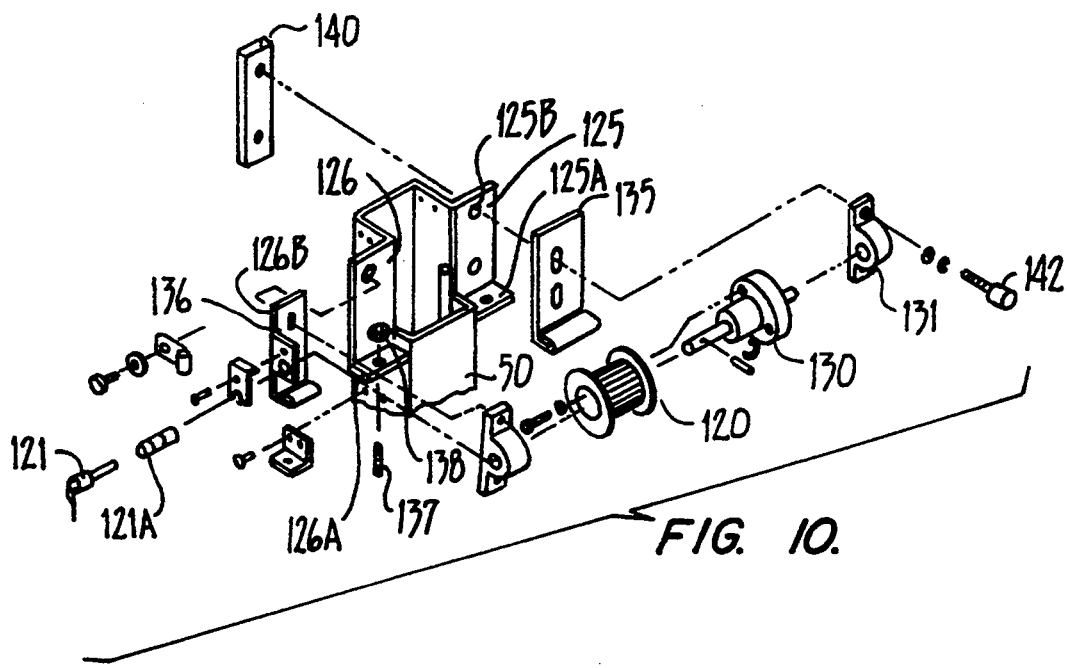
FIG. 10 is an exploded perspective view of a drive belt reel mounting arrangement with position tracking potentiometer and belt tensioning features used in a system in accordance with this invention.

Upper Pulley Mount and Tensioner (FIG. 10)

FIG. 10 illustrates in exploded perspective the mounting arrangement for the upper pulley 120 and associated position potentiometer 121 which includes a belt tension adjustment arrangement. A pair of mounting brackets 125 and 126 are formed on the top of support column 50. Each of these mounting brackets has a horizontally extending foot 125A and 126A. Upper pulley 120 is carried on a tapered bushing and shaft arrangement with the two end shafts thereof journalled in pillow block bearing arrangements 131, 132. These pillow block bearings are in turn carried on L-shaped mounting brackets 135 and 136. Bearings 131, 132 and associated brackets 135, 136 are bolted to column brackets 125 and 126 utilizing a nut and bolt mounting arrangement with bolts extending through mounting slots 125B and 126B (which allow for vertical adjustment of the position of brackets 136 and 136) and pillow block nut plates 140 (only one shown). An arrangement of a set screw 137 and nut 138 associated with each of the foot portions 125A and 126A provides the tensioning adjustment by pushing the bearing brackets 135 and 136 up, followed by tightening the mounting bolt and nut arrangement generally indicated at 142.

Bracket 136 also has a mounting tab for mounting potentiometer 121 thereon with a flexible coupler 121A between the shaft thereof and the pulley shaft.

Figure 11:
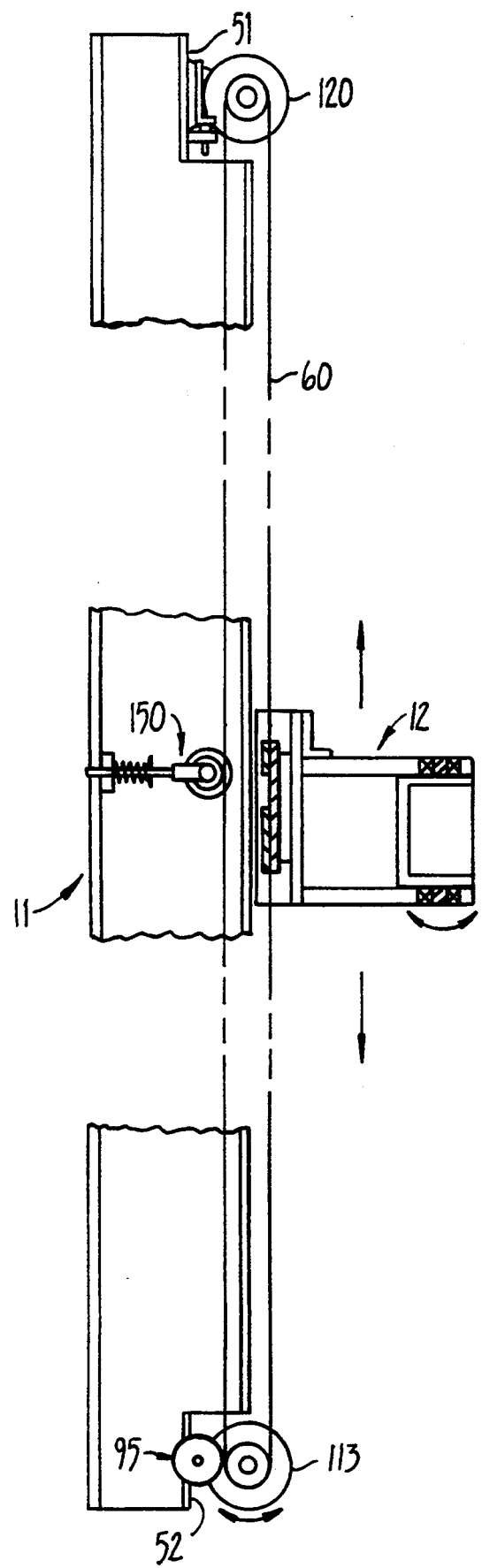
FIG. 11 is a schematic view illustrating the operation of a column support and drive arrangement useful in accordance with this invention.

Belt Transmission and Tensiometer (FIGS. 8 and 11)

FIGS. 8 and 11 illustrate the assembled belt drive arrangement with lower pulley 113 actively driven by the motor and reducer combination, upper pulley 120 with tension mounting arrangement and a tensiometer arrangement 150 which provides an indication of proper or improper belt tension and also serves the function of damping out bowstring harmonics from drive belt 60. Tensiometer 150 includes an idler pulley 151 which is carried on a shaft and bearing arrangement 152 with the ends of the shaft extending through horizontal slots 153 in the walls of support column 50 and captivated by a nut and washer arrangement which can be tightened down against the outer walls of the support column to lock this idler pulley 151 in position.

With this mounting arrangement, when the tensiometer is used to gage belt tension, the external mounting bolts 154 are loosened so that pulley 151 is free to move back and forth in the slots 153. A spring loaded fork 155 urges pulley 151 against belt 60. Fork handle 156 extends through a nut plate and bushing arrangement fastened to a removable back plate section 158 on support column 50. Back plate section 158 has an aperture therein through which a tension indicating section 156A,156B extends. The tensiometer 150 is designed such that, if belt 60 is at the value of the upper limit of acceptable belt tension, then surface 156B will be substantially flush with the wall surface 50C. If belt 60 is at the value of the lower limit of acceptable belt tension, then surface 156A will be flush with surface 50C. Thus if surface 156A is back behind the surface 50C, this indicates that belt tension is too loose. If surface 56B is in front of surface 50C, this indicates that belt tension is too tight. Once belt tension has been adjusted to the correct value, the bolts 154 are again tightened down to capture the idler pulley against the belt.

Figure 12:
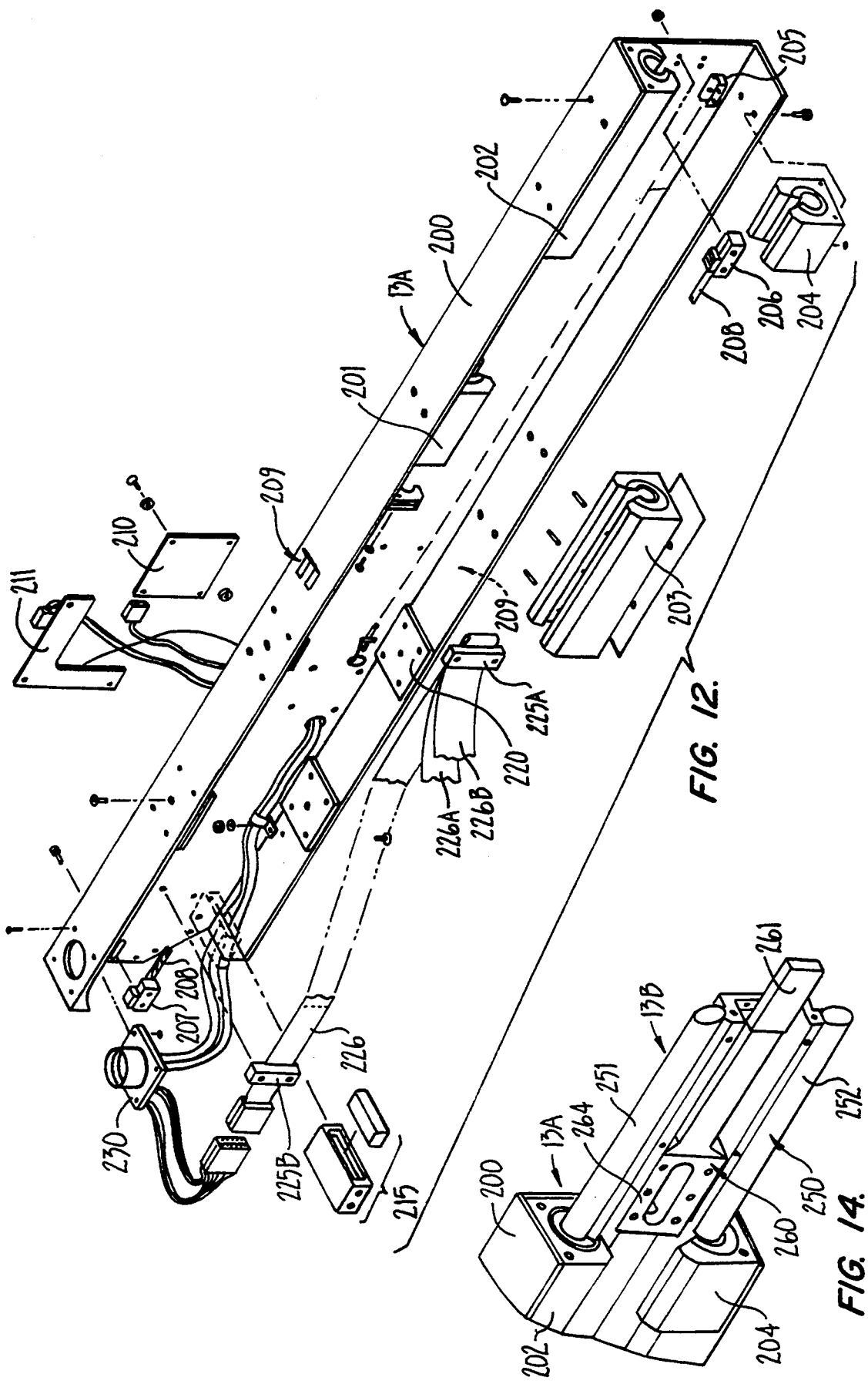
FIG. 12 is an exploded perspective view of a fixed arm subassembly used in a preferred embodiment of lift task apparatus in accordance with this invention.

Stationary Arm Subassemly (FIG. 12)

FIG. 12 illustrates in exploded perspective the components of stationary arm subassembly 13A. Metal housing 200 has four Linear ball bearings 201–204 mounted on upper and lower walls thereof in the positions indicated. The two longer bearings 202 and 203 are located at positions which will experience the larger thrust due to upward force placed on the slide 250 of the moving arm subassembly which extends therethrough as shown in FIG. 14.

An accelerometer 205 is mounted to a wall of housing 200 as indicated and signal leads therefrom are routed to circuit board 210 which is mounted to a wall section of housing 200 which is aligned with access aperture 74A in arm mounting bracket 74 (FIG. 7).

Timing belt brackets 206 and 207 are mounted to the back wall of housing 200 at positions shown and timing belt 208 is stretched therebetween. Timing belt 208 cooperates with a potentiometer and drive arrangement mounted on moving arm subassembly 13B to track the position of the moving arm subassembly relative to the stationary arm subassembly.

An arrangement of four strain gages 209 mounted on top and bottom walls of housing 200 have leads coupled to a strain measurement board 211 for measuring the amount of force applied to the stationary arm subassembly independent of the amount of force measured by the load cell arrangement 260 mounted at the end of the moving arm subassembly 13B as shown in FIG. 14. These four strain gages are mounted at a preset distance from the front end of housing 200 so that the strain measurement can be converted to an equivalent force value for comparison with the force measured by the load cell arrangement 260 in a safety check routine discussed below.

A stop block arrangement 215 is mounted to housing 200 at the back end thereof to serve as a mechanical stop on movement of the slide arrangement 250 in the moving arm subassembly 13B. This stops the inward movement of the slide arrangement before an attachment coupler mounted on the end of the moving arm will strike the end of the stationary arm.

Four arm backing plates 220 are fastened to inside top and bottom walls of housing 200 at locations where housing 200 is attached to arm bracket 74 (FIG. 7).

A pair of cable mounting brackets 225A and 225B mount a pair of flexible ribbon cable sections 226 to the back wall of housing 200 and continuing sections 226A and 226B extend to the moving arm subassembly 13A and carry parameter monitoring signals therefrom. A shielded cable connector 230 mounts in an aperture in the back of a top wall of housing 200 and couples all of the parameter measurement signals from the arm assembly 13. A mating connector and cable arrangement carries these signals to the drive and controller assembly 15 through a flexible chain cable protector as shown in FIG. 1.

Appropriately configured covers are mounted over the open front end, back end and side of housing 200 to complete this subassembly.

Figure 13:
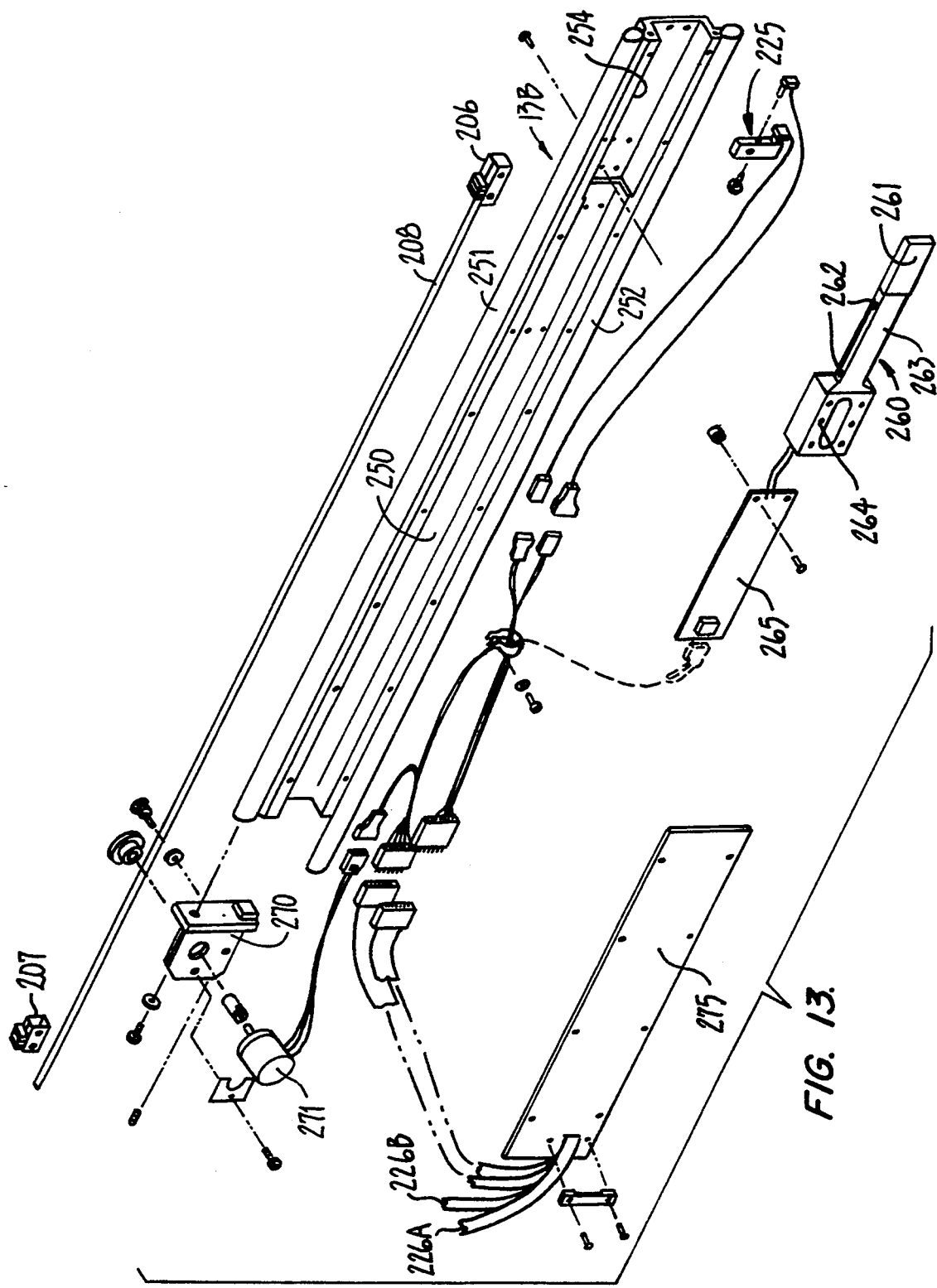
FIG. 13 is an exploded perspective view of a moving arm subassembly used in a preferred embodiment of lift task apparatus in accordance with this invention.

Moving Arm Subassembly (FIG. 13)

Moving arm subassembly 13 includes a specially fashioned dual bearing slide arm 250 whose slide rails 251 and 252 are received in linear ball bearings in the stationary arm subassembly 13A as shown in FIG. 14. An attachment detector arrangement 255 with two hall effect sensors incorporated therein is mounted in the front end of slide arm 250 in recessed area 254. Signal leads from this detector arrangement 255 extend back through a series of connectors into one of the ribbon cables 226A and 226B. Also mounted in recessed area 254 is a force measuring load cell arrangement 260 with a front end beam portion 261 which extends beyond the front end of slide arm 250 to cooperate with an attachment coupler to mount an attachment on the force measuring arrangement 260. A back end mounting section 264 is received in a precision machined slot 254 as shown in FIG. 14 to prevent horizontal or rotational movement of the load cell when under load. Six machine screws cooperate with six threaded apertures in the mounting section 264 to attach the load cell to the arm.

An arrangement of four strain gages 262, two on a top surface of bar section 263 and two on a bottom surface thereof in positions generally as shown, are connected through signal leads to a parametric amplifier board 265 and the output signals from this board are led via a cable and connector arrangement into one of the ribbon cables 226A, 226B. As will be discussed in more detail below in connection with FIGS. 15, 16, and 18, this force measuring arrangement accurately measures the amount of vertical force applied to front beam section 261 by an attachment mounted thereon without parasitic sensitivity to side thrust forces or bending moments applied to beam section 261 by the attachment.

A potentiometer mounting bracket 270 is mounted at the rear end of slide arm 250 and carries potentiometer 271 thereon. The shaft of potentiometer 271 is coupled to a timing gear wheel 272 carried on mounting bracket 270 and this timing gear wheel is turned by timing belt 208 as slide arm 250 moves in and out of stationary arm subassembly 13A. The output of potentiometer 271 is coupled via signal leads and connectors into one of the ribbon cables 226A, 226B and reports the current position of the slide arm (the R-coordinate in the cylindrical coordinate system associated with the lift system 10). An arrangement of cover plates such as plate 275 is utilized to cover the components and cables mounted on the slide arm 250.

Figure 16:
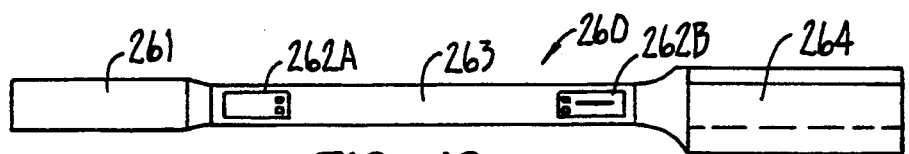
FIG. 16 is a top plan view of a force measuring load cell employed in a preferred embodiment of this invention.
Figure 15:
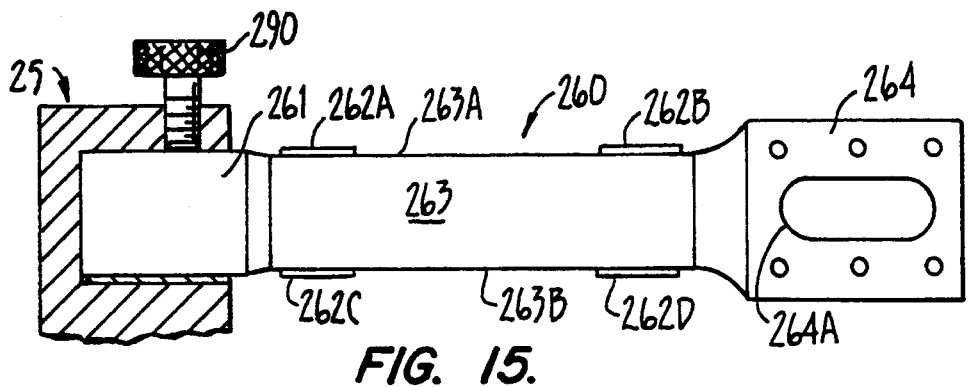
FIG. 15 is an elevational view of a force measuring load cell employed in a preferred embodiment of this invention.
Figure 18:
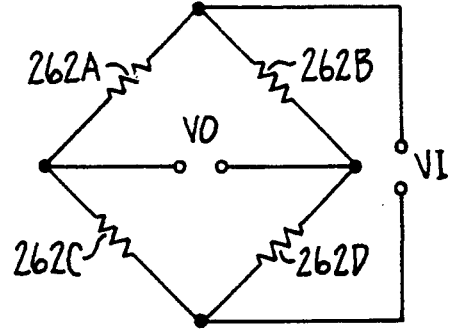
FIG. 18 is a schematic drawing of the connection of the strain gages of the load cell of FIGS. 15 and 16 into a bridge circuit.

Force Measuring Arrangement (FIGS. 15, 16, 18)

Structural details of the load cell of force measuring arrangement 260 are shown in FIGS. 15 and 16. This load cell is formed from a bar of stainless steel and has a mounting section 264, a strain measuring center section 263 of reduced thickness and height and a load attachment section 261. Two strain gages 262A and 262B are mounted at accurately registered positions on top surface 263A and two strain gages 262C and 262D are mounted at precisely opposite locations on bottom surface 263B.

FIG. 18 shows the electrical connection of the four strain gages in a bridge arrangement and the application of an input voltage VI across the strain gage bridge and the reading of an output voltage VO as shown.

The structure and operation of the load cell arrangement is such that only the component of upward force exerted by the attachment on the arm of the lift assembly is measured by this load cell arrangement and other forces applied thereto are automatically nulled out by the arrangement. Thus the output voltage VO is proportional to the input voltage VI multiplied by the vertical force value. Since the moving arm will have side forces and bending moments applied thereto due to the R-component of movement and the Theta-component of movement of the arm, this improved force measuring arrangement provides the needed accuracy of measurement of only the vertical force for accurate intertial response of the system and accurate measurement of vertical lifting force applied by the patient.

Figure 17:
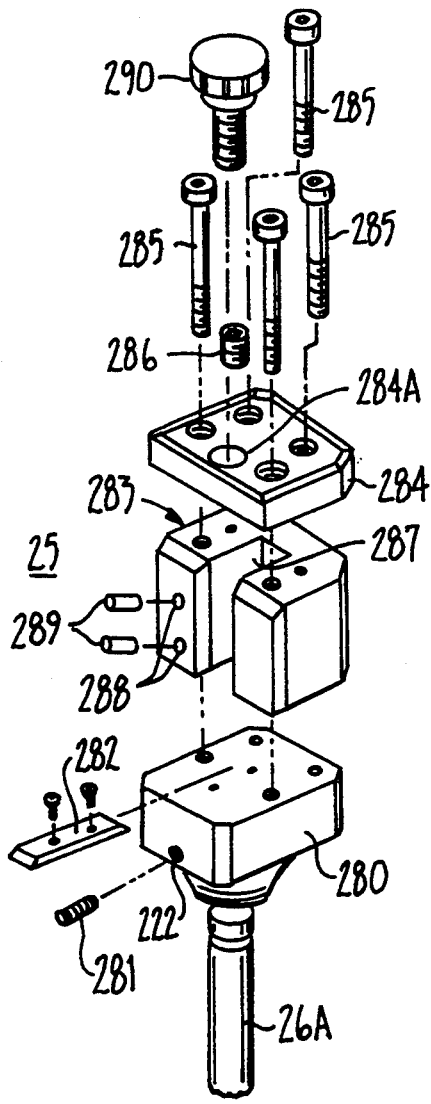
FIG. 17 is an exploded perspective view of a connector assembly useful for attaching patient interface devices to the arm of a lift task apparatus in accordance with this invention.

Attachment Connector Subassembly (FIG. 17)

The attachment connector subassembly 25 used on all of the attachments for the lift task system of this invention is illustrated in exploded perspective in FIG. 17. A base coupler block 280 has a cylindrical bore (not shown) in the bottom thereof which receives coupler shaft 26A and a set screw 281 is employed as shown to fasten these two pieces together. A squash plate 282 of resilient material is fastened on a top surface of block 280 as shown. Spacer block 283 and top block 284 are mounted on the top surface of base block 280 by a set of four bolts 285 which extend through mating apertures in top block 284 and spacer block 283 into threaded apertures in base block 280. Recess 287 formed in spacer block 283 receives the free end section 261 of load cell arrangement 260 as shown in FIG. 15.

A pair of shallow bores 288 in spacer block 283 are formed to receive an arrangement of one or two magnets which code the related attachment with a binary number in a four number sequence. The presence or absence of these magnets is sensed by the hall effect sensor arrangement 255 on the end of the sliding arm 250 (FIG. 13).

A threaded E-Z Lock insert is mounted in aperture 284A in top block 284 and receives a fastening hand screw 290 which can be tightened to hold the associated attachment on the bar section 261 as shown in FIG. 15.

Figure 19:
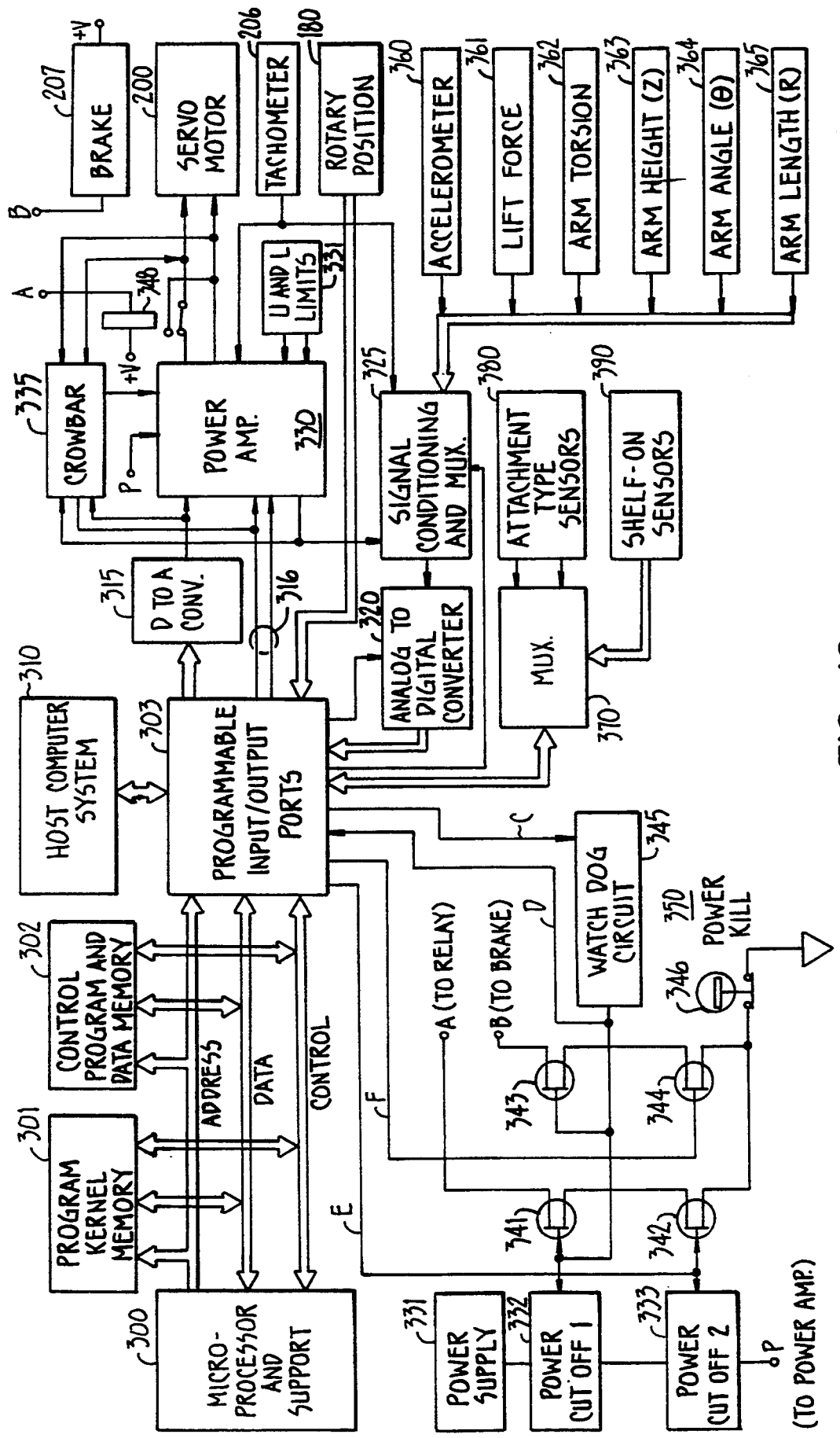
FIG. 19 is a block schematic diagram of one embodiment of a microprocessor based data acquisition and controller arrangement for a lift task apparatus in accordance with this invention.
Figure 20:
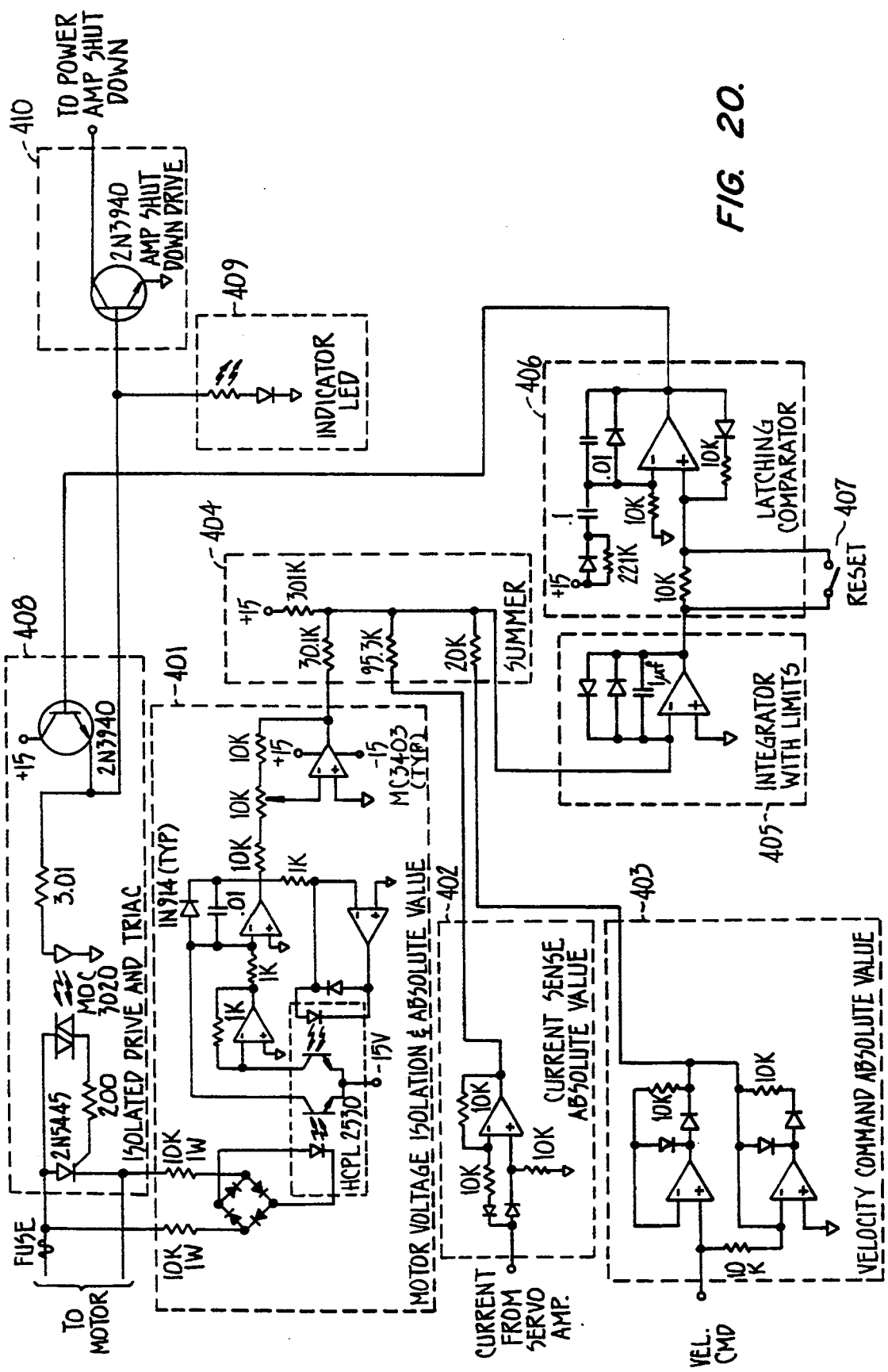
FIG. 20 is an electrical schematic diagram of a crowbar safety circuit useful in the controller arrangement of FIG. 19.

Microprocessor Based Controller (FIGS. 19-20)

FIGS. 19 and 20 are block diagrams which illustrate one embodiment of a computer control system for use in the lift task method and apparatus of this invention. The computer control arrangement is based on a standard real time microprocessor control system architecture which does not need to be explained in detail. A microprocessor and support circuit arrangment 300 of standard design communicates via data, address and control busses with program memory 301, data memory 302, and programmable input and output ports 303. Ports 303 provide data and control communication channels to a host computer system 310, a digital to analog converter 315 and analog to digital converter 320. D/A converter 315 has its output coupled to power amplifier 330. This is the path by which microprocessor 300 sends a velocity command to power amp 330 which operates with servo motor 200 and tachometer 206 in a velocity servo loop.

This invention is not limited to any particular form of servo control system and other forms than velocity servo control may be employed, for example the position based servo control system disclosed in co-pending and commonly assigned Dempster et al. application Ser. No. 07/866,112, filed Apr. 7, 1992, which is the continuation of application Ser. No. 07/472,399 filed Jan. 31, 1990, now abandoned, and entitled "POSITION BASED MOTION CONTROLLER" could be used in place of the velocity based servo system shown in FIG. 19 and that application is hereby incorporated by reference as if fully set forth herein.

Ports 303 also directly couple two disable signal channels 316 into power amp 330 so that the microprocessor 316 can immediately disable the power amp under certain emergency conditions when it detects that the system is not behaving in a safe manner. These are redundant disable channels and completely disable the power amp from driving the servo motor in either direction. Ports 303 also send and receive signals on direct channels C, D, E, and F to safety circuit 350.

A/D converter 320 provides the channel through which microprocessor 300 acquires digital versions of the various signals which are sent out by various parts of the system. Rotary position encoder 180 provides a digital signal output directly into ports 303. All other signal inputs are analog and are routed through a signal conditioning and multiplexing circuit 325 which conditions each signal, as necessary, and also does low pass filtering and buffering. This circuit then multiplexes one signal at a time in sequence to the A/D converter 320. In this manner the microprocessor obtains the value of the output signals from tachometer 206, accelerometer 360, lift force measurement system 361, arm force measurement system 362, arm height (Z-coordinate) transducer 363, arm angle (theta-coordinate) transducer 364, and arm length (R-Coordinate) transducer 365. It also obtains the power amp current from power amp 330.

The attachment type sensor group 380 and the shelf-on sensor group 390 have outputs coupled thorugh a multiplexor 370 into ports 303 so that the condition of these sensors can be read one at a time in sequence. This enables the software control program to determine the presence and type of attachment and the presence and location of a shelf.

Upper and lower hall effect limit switches 331 directly control the power amp to disable it when either switch is triggered. Crowbar circuit 335 also performs an important safety function. Its structure and operation are discussed below in connection with the diagram of FIG. 20.

Safety Circuit System 350

Safety circuit system 350 functions together with relay 348 and brake 207 to prevent the servo motor system from operating in an unsafe manner. Relay 348 is connected in a series circuit with two field effect transistor (FET) switching devices 341 and 342 and a power kill switch 346. For relay 348 to be operated to maintain contact arrangement 349 in the position shown, the power kill switch 346 must be closed and both FETs 341 and 342 must be on. Brake 207 is connected in a series circuit with two FETs 343 and 344 and kill switch 346. When no power is applied to brake 207 it is in a brake applied condition and prevents rotation of the servo motor shaft. When power is applied, the brake is released.

Power kill switch 346 has normally closed contacts and can be operated by a person monitoring the systems performance to open the circuit to relay 348. When relay 348 has its power interrupted, switch 349 connects the ends of the windings of the servo motor together and servo motor 200 operates in a regenerative braking mode and brakes itself and the output shaft and tool thereon to a stop. Operation of the power kill switch 346 also interrupts power to brake 207 and brake 207 responds by immediately braking the shaft and motor to a stop.

A signal over line E from port 302 can be sent by the microprocessor to turn off FET 342 and another separate signal can be sent over line F to FET 344. A signal on line E operates AC power cut off 333 and turns off relay 348 to disable the power amp and cause the servo motor regeneratively to brake itself. A signal on line F only applies the brake 207. These provide the computer with the ability to shut down the servo motor system under defined safety conditions. Also the direct control of the operation of the brake is used by the computer during an isometric hold mode of operation of the system. This avoids requiring the servo motor to absorb all of the torque applied during an isometric hold and eliminates the possibility of overheating the motor during a long isometric hold.

Watchdog circuit 345 receives a series of timed pulses from microprocessor 300 over line C from port 303. If the microprocessor and its program are operating correctly, these pulses will arrive at a nominal rate of one hundred Hertz. If the frequency of arrival of these pulses goes outside of upper and lower limits built into the watchdog circuit 345, it will produce an output that turns off both FETs 341 and 343 and removes AC power via cutoff device 332 to disable the power amp 330.

It is thus seen that there are five separate and independent systems and methods for shutting down the servo motor drive system under safety or fault conditions:

1. Turn off relay 348 and thereby disconnect the motor 200 from the power amp 330 while also shorting the motor windings to produce regenerative braking;
2. Disable power amp 330 via commands over lines 316;
3. Disconnect the AC power to power amp 330 via a command over line E or an output from watchdog circuit 345;
4. Command the amplifier to halt the motor by a zero velocity command sent through the D-A converter 315; and
5. Disconnect power to the circuit which holds brake 207 in a brake released position via a signal on line F.

When microprocessor 300 shuts down the system, it uses all five methods. When watchdog circuit 345 shuts down the system, it uses methods 1,3, and 5. When the Kill button 346 is pressed, it uses methods 1 and 5. Microprocessor 300 senses a system shutdown by other safety system and immediately uses all other shut down approaches. The watchdog circuit 345 and microprocessor 300 have separate systems to accomplish the shutdown approaches 1, 3, and 5.

Examples of various emergency conditions that might be experienced by the system and produce shutdown are discussed in the software flow charts below.

Crowbar Circuit (FIG. 20)

The crowbar circuit 335 illustrated in detail in FIG. 20 is utilized to supervise the integrity of the velocity servo loop and disable the system rapidly when loss of integrity is detected. An example of loss of integrity is loss of tachometer operation which causes the amplifier to be driven to an extreme condition regardless of the velocity input condition. In this case, full power could be applied to the servo motor in the absence of any input velocity command to the servo amplifier.

Crowbar circuit 335 functions by motor speed from power amp current and motor voltage independent of the tachometer output value. This estimate is compared to the velocity command input to the power amplifier from the computer system. If the crowbar circuit determines that the motor speed is too high, it shorts out the motor and turns off the power amplifier.

The motor terminal voltage is a linear function of its angular velocity and the current through the windings. Except at low speeds, the angular velocity term dominates this function. The absolute value of the motor voltage is calculated in Motor Voltage Isolation and Absolute Value circuit 401. The absolute value of the motor current is calculated by the Current Sense Absolute Value circuit 402. The absolute value of the velocity command signal into the servo loop is calculated in Velocity Command Absolute Value Circuit 403. The outputs of these three absolute value circuits 401, 402, and 403 are proportioned and summed with a constant (to correct for baseline errors) in summer circuit 404.

The summed analog signal resulting is fed to an Integrator with Limits circuit 405 which makes the crowbar circuit insensitive to very transient conditions, such as would occur if there were an attempt to abruptly stop the motor by an input command from the computer. Lag in the velocity servo loop would produce a brief illegal condition which the integrator prevents the crowbar circuit from recognizing. The output of the Integrator 405 is fed to a Latching Comparator circuit 406. When an illegal condition is detected, Latching Comparator 406 is triggered and latched in an operated condition and its output (1) drives an Isolated Drive and Triac circuit 408 to short out the motor, (2) operates Amp Shut Down Drive circuit 410 to send a signal to shut down the Power Amp (which should eliminate current to the motor), and (3) lights indicator LED 409 to show that the crowbar circuit has been triggered. A reset 407 is provided to reset the latching comparator for convenience of technicians during testing of the system.

The triac in circuit 408 is capable of accepting full amplifier current which effectively disables the amplifier and cause the motor to regeneratively brake. The triac is mounted to a small aluminum block with heat capacity sufficient to absorb the energy of a full scale dynamic motor braking operation. If the power amplifier should continue to provide full scale current to the triac, in spite of the crowbar circuit's command to turn it off and the internal safety systems in the amplifier itself, a series fuse in the leads to the motor will blow and disconnect the amplifier from the motor.

Figure 21:
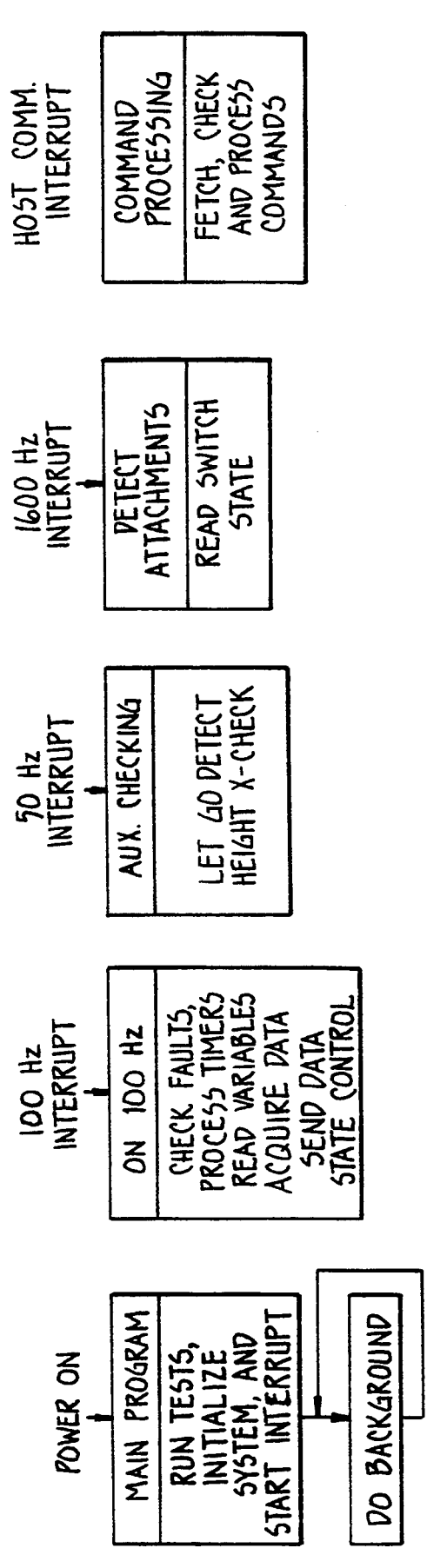
FIGS. 21 and 22 are diagrams that illustrate the structure and function of an interrupt driven software control program for a lift task apparatus in accordance with this invention.
Figure 22:
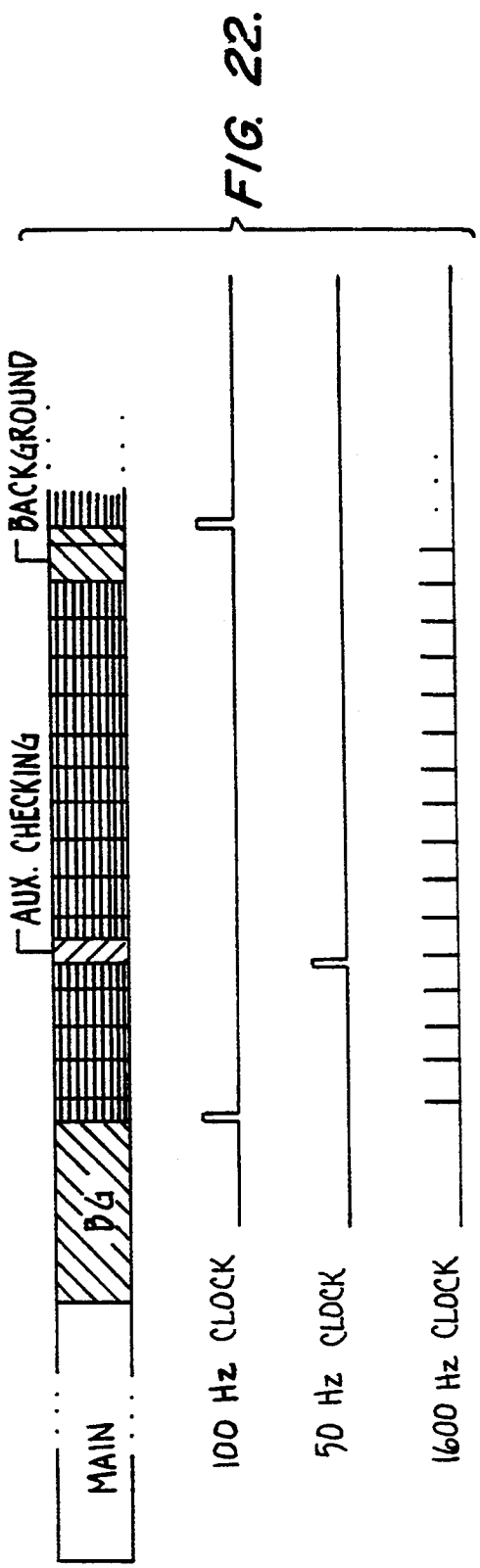

Control Program Structure (FIGS. 21, 22)

FIGS. 21 and 22 illustrate the general structure of the control program software utilized in one embodiment of this invention. As shown in FIG. 21, there are six general program modules called Main Program, On 100 Hz, Auxiliary Checking, Detect Attachments, and Command Processing. The Main Program starts running on Power Up of the system and then enters its Do Background Loop which runs continuously when not being interrupted by other program modules. The functions performed in the Main Program are running tests, initializing the system (hardware and variables) and starting the interrupt timers. The next three modules are executed when their associated interrupt clock ticks occur. ON 100 Hz executes on each tick of the 100 Hz clock as shown in FIG. 22. It may be interrupted by any of the other interrupt driven modules, except that critical portions of the routine may be protected by disable interrupt commands so that they will finish their execution prior to processing of an interrupt.

The On 100 Hz routine does fault checking, timer processing, reading of variables, aquisition of data, sending of data to the host computer and state control processing.

The Auxiliary Checking module executes on each tick of a 50 Hz clock as shown in FIG. 22. It performs Let. Go checking and a height cross-check safety routine. If the microprocessor used in the system has adequate processing speed, this Auxiliary Checking module could be included in the On 100 Hz module.

The Detect Attachments module executes on each tick of a 1600 Hz clock and reads in sequence the state of each of the switches related to the shelves and the attachment sensors on the end of the arm of the lift system.

The Command Processing module executes when the Host Computer send a communication interrupt and it fetches, checks the validity of, and processes commands from the Host Computer.

Figure 23:
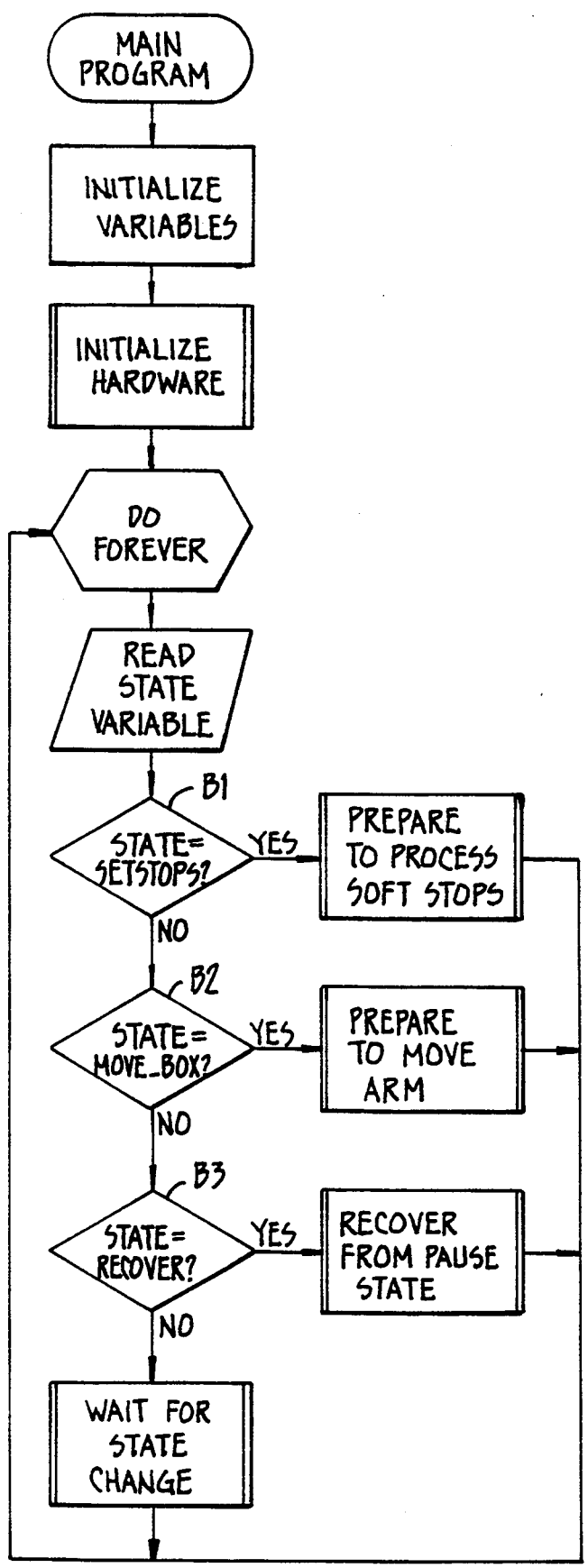
FIGS. 23-41 are flow charts illustrating the operating features and functions of various software control program modules for use in connection with the microprocessor based controller system of FIG. 19 in a lift task apparatus in accordance with this invention.

Main Program and Background Loop (FIG. 23)

The Main Program is entered on power up of the system and first performs standard program steps of initializing the variables and initializing the hardware of the system. The program then enters the background loop which runs continuously except when interrupted by other program modules. The first step in this Background loop is to read the State Variable which has been communicated from the host computer and stored in a control program variable memory location. Then three sequential state checking steps are executed to determine if the State Variable read is one of Setstops, MoveBox, or Recover. These are states associated with processing commands and information from the host computer.

If the state variable read is Setstops, checking step B1 returns a YES, and a routine is executed to prepare the system for processing the setting of softstops which is actually done in the On 100 Hz routine. If the state variable read is Movebox, checking step B2 returns a YES and a routine is executed to prepare to move the arm to a commanded Z coordinate of the system. If the state variable read is Recover, checking step B3 returns a YES and a routine is executed to recover from a Pause state. If none of these three states are the one that is read, this module executes a routine to look for a change in the State Variable which may be set either from the Host Computer or by a routine executing in the On 100 Hz module. When a state change is detected, the program loops back and executes again.

Figure 24:
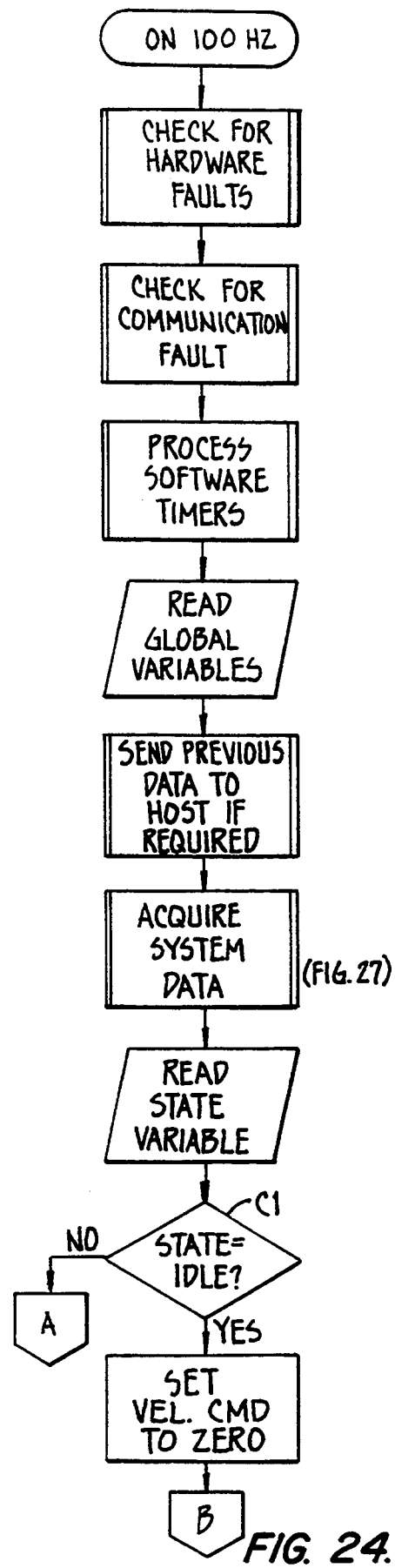
Figure 25:
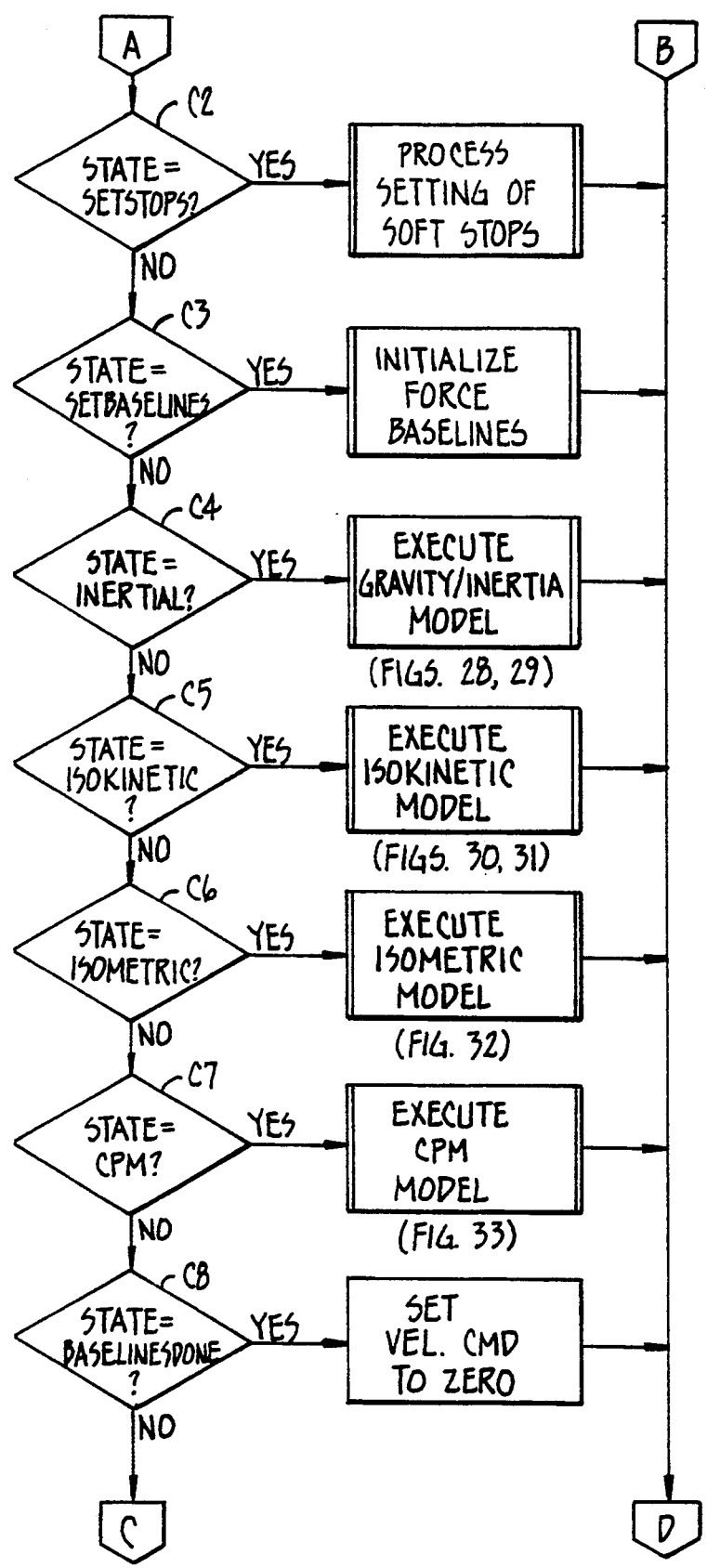
Figure 26:
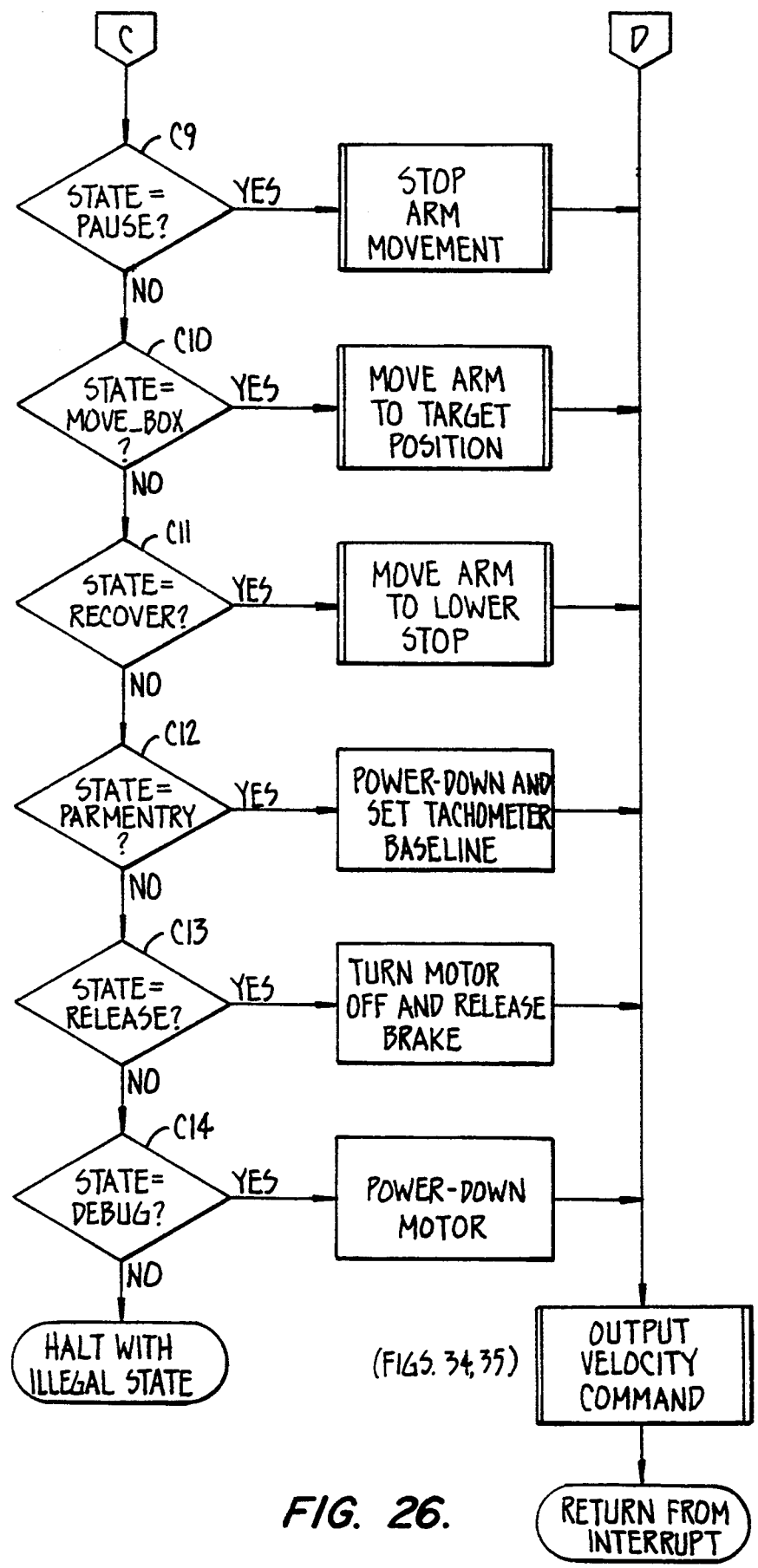

On 100 Hz Module (FIGS. 24–26)

The first portion of the On 100 Hz Module is shown in FIG. 24. First two routines are executed to check for hardware faults or communication faults. If any faults are detected, the system is typically shut down and will not execute further until the faults are cleared. Steps involved in safety shut down of the system are discussed above in connection with the watchdog timer circuit and the crowbar circuit. After these fault check routines are executed, software timers are processed as required and then stored global variables are read. Then previously acquired data is sent to the host computer for display or storage according to the operations being carried out by the host for the particular exercise mode being executed.

After sending data to the host, an Acquire System Data routine is performed, during which all of the real time machine parameters are read. This routine is shown in detail in FIG. 27 and will be described below. Following this the state variable is read and the routine goes through a series of checking steps to determine which state the system is in and executes the appropriate routine associated with that state.

Idle State

The Idle state is simply a state in which the machine is not doing any lift task exercise or other activity. Checking step C1 determines whether the state variable corresponds to the Idle state. If this returns a YES, then Vel.Cmd is set to a zero value and the routine passes to executing the Output Velocity Command routine as shown on FIG. 26.

Setstops State

Referring now to the portion of the On 100 Hz Routine shown on FIG. 25, the Setstops state involves simply setting the values of the the upper stop parameter, U.Stop, and the lower stop parameter, L.Stop, into associated memory locations for those therapist settable variables. Accordingly if checking step C2 returns a YES, a routine is exeuted to process the setting of upper and lower soft stops for the system. This is a simple routine and need not be shown or disccussed in detail.

Initialize Force Baselines

The routine to initialize the force baselines of the system involves two separate baseline determinations, one static and the other dynamic. The static part involves determining the baseline force value measured by the load cell on the end of the arm when the arm is stationary and there are no external forces being applied except the weight of the box or other attachment placed thereon. This Box. Weight parameter is later used to baseline correct the force measurement during an actual lift task exercise motion. It should be understood that this Box.Weight parameter also contains a component which represents the baseline output of the force measurement system itself (i.e. without any load thereon) but it is not necessary to measure this separately.

The dynamic part of this baseline initialization routine involves determining the contribution to the force measured by the load cell on the end of the arm which is contributed by the acceleration of the box or attachment itself in the earth gravitational field. To accomplish this, the arm is subjected to a patterned acceleration such as a movement of the box with sinusoidal velocity values and correlated accelerometer and baseline corrected force measurement data is accumulated. Then using recursive data analysis techniques, the stored acceleration and force data is examined to determine a function which correlates inertially produced force with acceleration as measured by the accelerometer at the end of the arm. This correlation function is then applied during operation of the system in a lift task performance mode to convert the accelerometer output signal value to an inertial force value to be subtracted from the measured force value to determine the actual force applied by the patient.

The reason for performing this force baseline initialization routine is that the lift task system of this invention is intended to model a simulated mass value in the gravity/inertia mode of operation where the simulated mass value is unrelated to the actual mass value of the box being used. It is thus apparent that all of the components of the force measurement represented by the actual mass of the box and the force produced by acceleration thereof must be removed from the measured force value so that system control is based solely on the force applied by the patient.

Inertial, Isokinetic, Isometric and CPM States

These states each correlate with one of the operating modes of the lift task system of this invention. The series of checking steps C4–C7 determine if the state variable correlates with one of these states and, if so, executes the associated lift task mode control routine. Each of these routines is shown in a separate flow chart and will be discussed in detail below.

Other States

The other states of the system associated with checking steps C 7 through C 14 are self explanatory and will not be discussed here.

Figure 27:
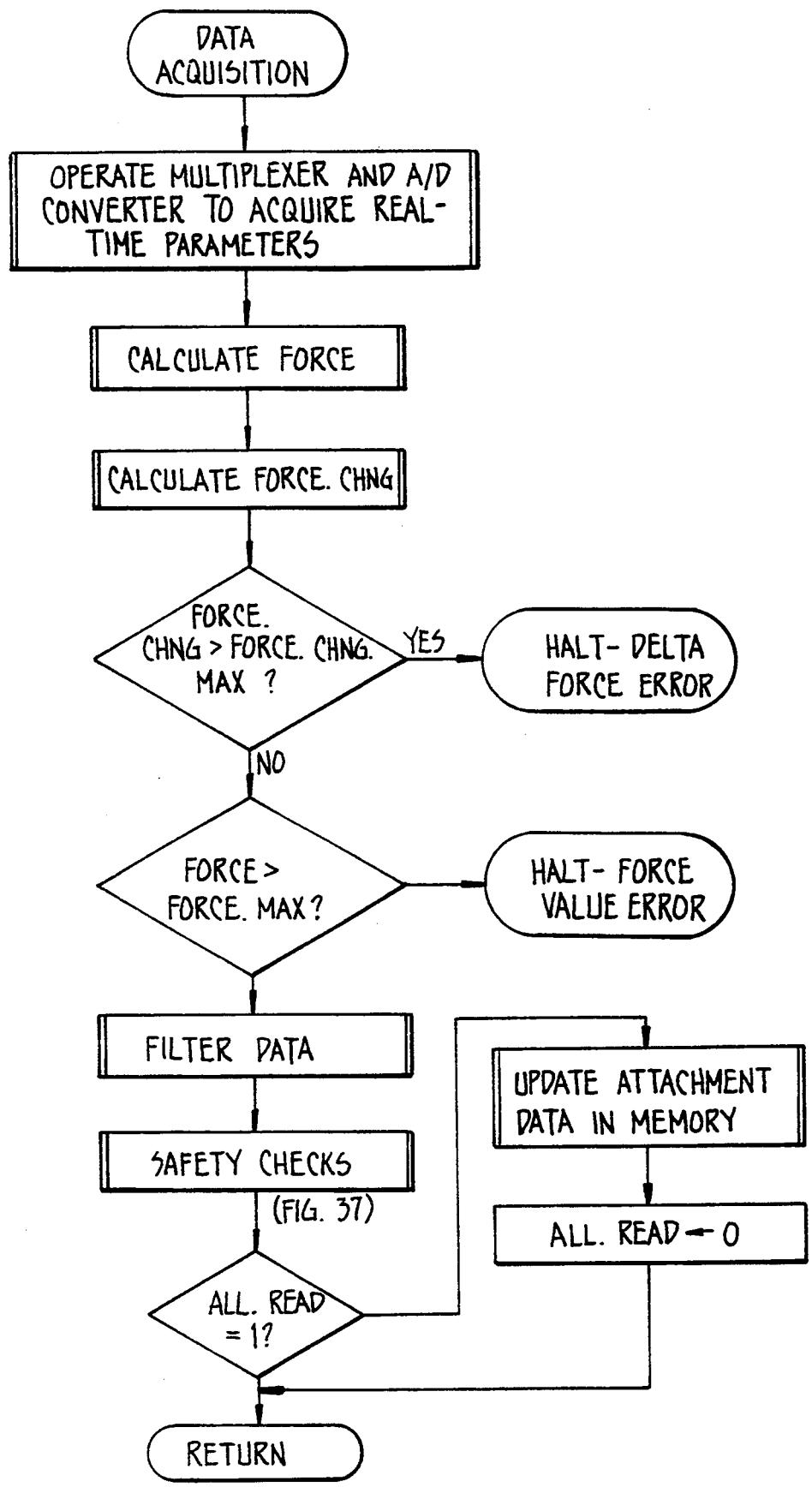

Data Acquisition Routine (FIG. 27)

The data acquisition routine shown in FIG. 27 is called and executed each time the ON 100 Hz routine shown in FIGS. 24–26 is executed. The first step of this routine is to operate the A/D Coverter 320 and multiplexor 325 (FIG. 19) to acquire the current values of all of the real-time parameters of the system shown as inputs to the multiplexor. The next step is to calculate the value of Force from the Lift. Force value by subtracting the previously measured weight of the attachment and the inertial component of force due to acceleration of that mass using the current value of the accelerometer output. The form of equation for this calculation is $$Force = Lift.Force - Attach.Wt - Cur.Accel/D$$

where
Force is the force actually being placed on the attachment by the patient,
Lift.Force is the current value of the force on the force measuring load cell on the end of the arm,
Attach.Wt is the weight of the attachment on the arm previously measured during the "shake the box" routine, Cur.Accel is the current value of acceleration as reported by the accelerometer on the end of the arm, and D is a gain factor which was calculated during the "shake the box" routine as the factor to apply to the value of Cur.Accel to come up with the amount of force due to acceleration of the attachement.

Following this force calculation step, the amount of change in force from the last sampling period is calculated and the system is halted if either the force change amount is too large or the force value is too large, since either of these conditions indicate some failure or unreliability of the measurement system or system components that acquire the real time data. For example if the A/D Converter were to have a sudden gain change or were to fail in a mode that produced a maximim digital value, then one of these error conditions would be tiggered and the system would halt.

Figure 37:
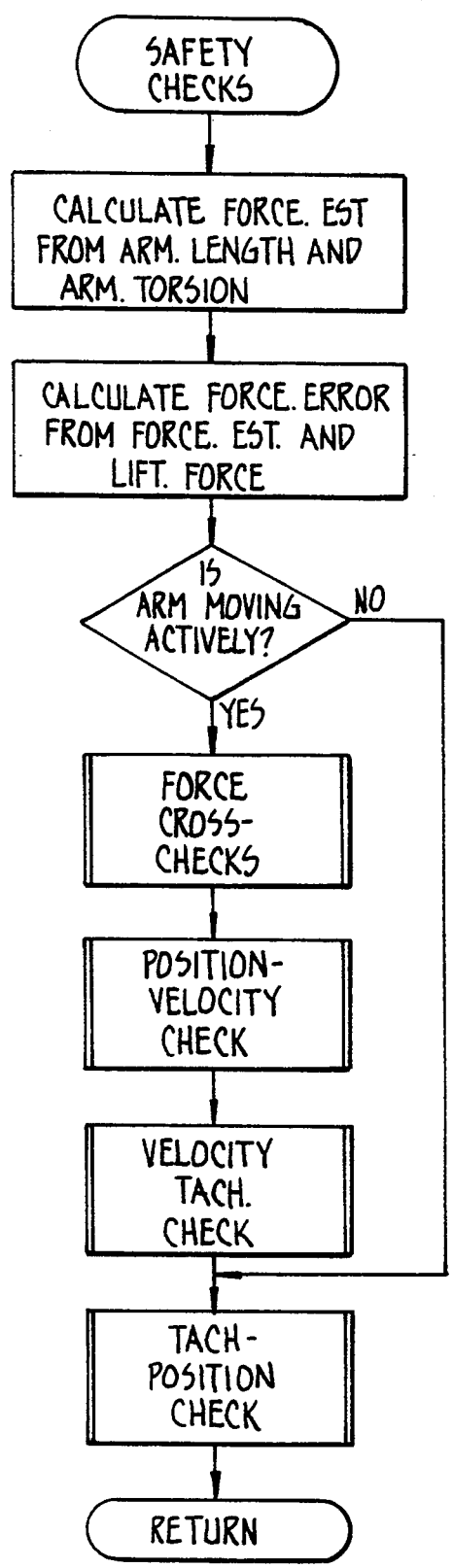

If these error checking steps both return NO, certain of the acquired data parameters are filtered by averaging them over a certain number of data acquisition cycles. Then the Safety Check routines shown in FIG. 37 are executed. If none of the safety check routines produce a halt of the system, a checking step is executed to determine if the All.Read flag has been set, and if it has, the attachment information stored in memory is updated and the All.Read flag is reset to 0, or else the currently stored data and the All.Read flag value are left as is. This completes execution of this routine.

Figure 28:
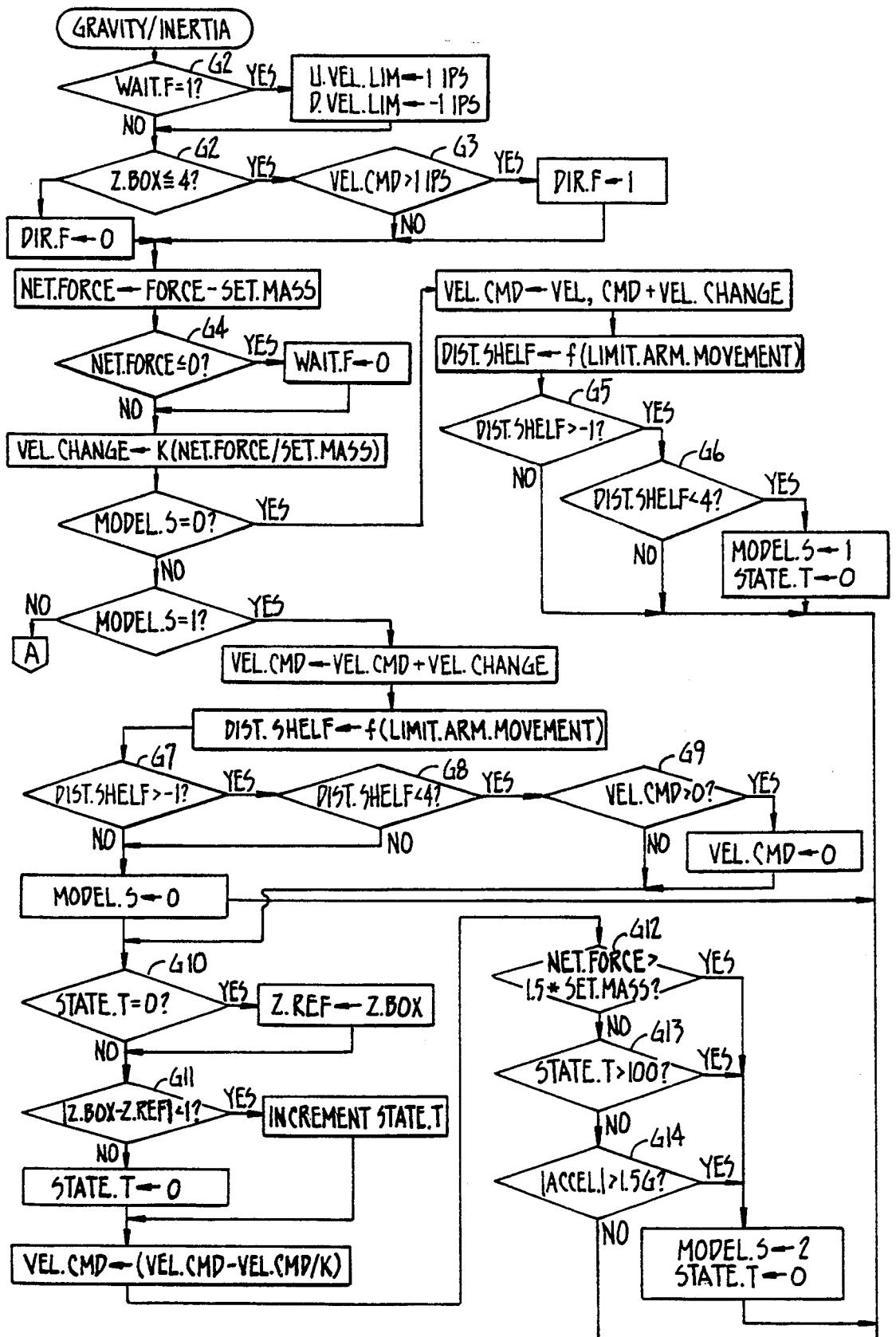
Figure 29:
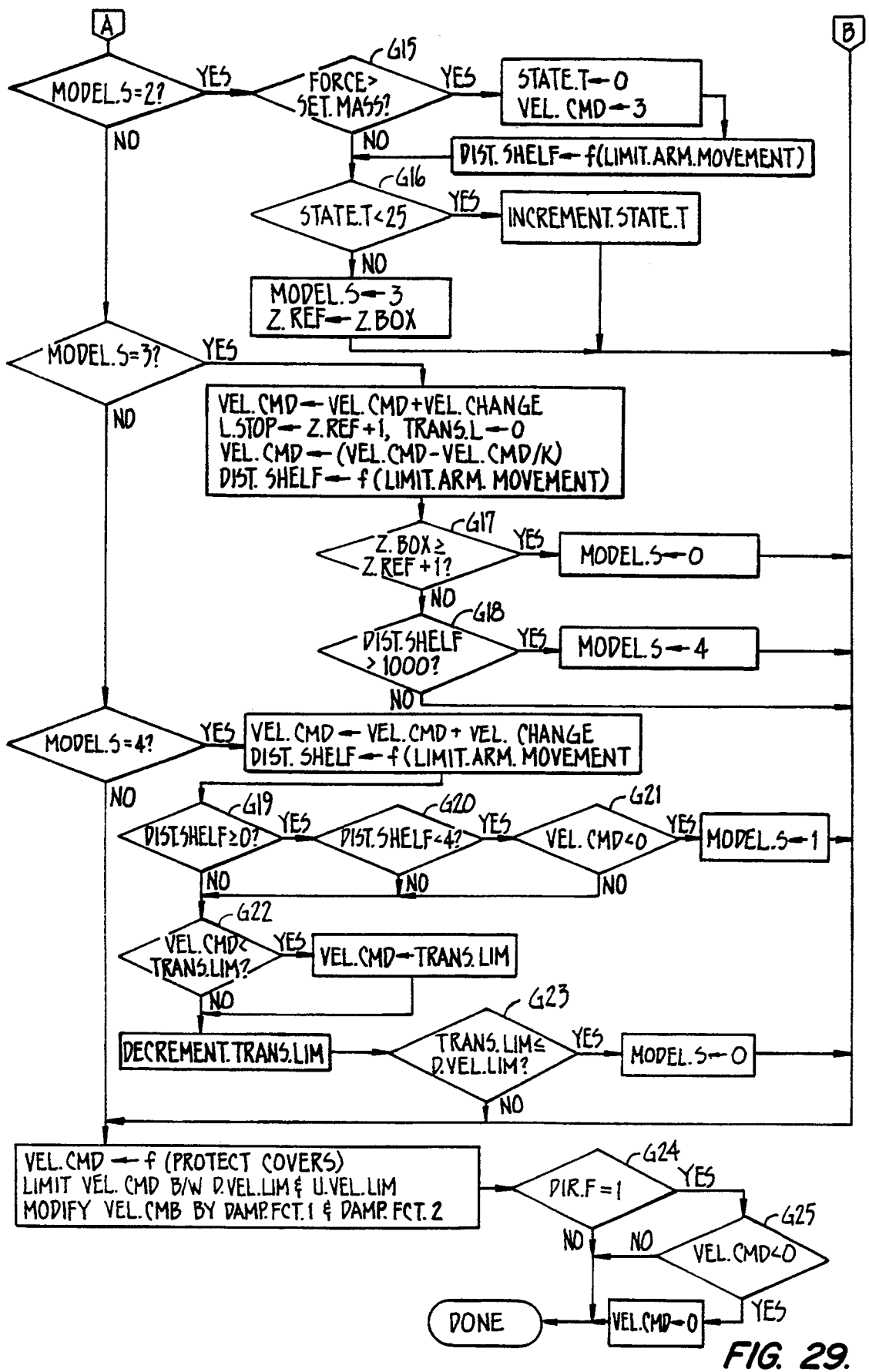

Gravity-Inertial Model (FIGS. 28,29)

Prior to first entering the Gravity/Inertia model, the parameters Dir.F and Model.S are set to 0 and the Wait.F parameter is set to 1. The first step G1 of the Gravity-Inertial Model checks if the Wait.F value is 1, and if this returns YES, then the U.Vel.Lim is set to 1 IPS and D.Vel.Lim is set to $-1$ IPS. This limits the magnitude of the velocity command when the model is first entered so the system will not misbehave at that time. It should be undertstood that each time the model is entered during exectution of the On 100 Hz Routine, the global values for these two velocity limit parameters will be passed to the model and will only be replaced by these lower limits when the Wait.F value is 1, i.e. only during the start up phase of the model before the subject starts lifting the box or other attachment.

The next checking steps G2 and G3 determine whether the box is moving upward and has passed an initial four inches of travel. If both checks return YES, then the value of Dir.F is set to 1 so that thereafter the last step of the routine will not permit the box to be set down until the four inch point has been reached. If either of these checks returns NO, then the value of Dir.F is set to 0 and the last step of this routine will not have any effect on operation.

Next the value of Net.Force is calculated as shown. Checking step G4 looks for a negative Net.Force value and sets the Wait.F value to 0 if it finds it. Next the value of Vel.Change is calculated as shown. Then a series of model state checking steps is executed to determine what state the model is in and to execute an appropriate state related routine.

Model State 0

In model state 0, the value of Vel.Cmd is calculated as shown and then the Limit.Arm.Movement function is called and the returned parameter set into Dist.Shelf. (See FIGS. 46 and 47 and description below). Then the Dist.Shelf parameter is checked by steps G5 and G6 to determine if the box is above and near the shelf position. If both steps return YES, then the box is about to be set on the shelf and Model.S is set to 1 and State.T (state timer) is set to 0, so that the next time in a routine to control setting the box on the shelf will execute in Model State 1.

Model State 1

In this state, the value of Vel.Cmd is calculated and the Limit.Arm.Movement function is called and the same two checking steps on the value of Dist.Shelf are performed here as steps G7 and G8. If both return YES, and if step G9 returns YES because the value of Vel.Cmd is positive, then Vel.Cmd is set to 0 so that the box will not be able to be lifted upward if it is near the top of the shelf. The box can move sideways, however, and if either checking step of Dist.Shelf returns NO, this means the box has been slid off the shelf and Model.S is set to 0.

If the box is still above the shelf and coming down, then if step G10 returns YES because the value of State.T is 0, then Z.Ref is set to the value of Z.Box. Step G11 checks to see if the box has moved vertically less than one inch, and if this returns YES, then the value of State.T is incremented or else it is reset to 0. Thus State.T will stay at 0 until the box stops moving. Next Vel.Cmd is subjected to a viscous model using the calculation shown and then three checking steps are executed to see of the model state should change. Step G12 looks for a value of Net.Force that indicates that the box is pressing hard on the shelf. Step G13 looks for a value of State.T that indicates the box has been stationary for one second (100 executions of the On 100 Hz routine). Step G14 looks for a value of the Accelerometer output that indicates the box has collided with the top of the shelf. If any of these return YES, Model.S is set to 2 and State.T to 0.

Model State 2

In Model State 2 (FIG. 29), checking step G15 is executed to determine if the box is pressing down on the shelf more than the value of Set.Mass and if this returns YES, State.T is set to 0 and Vel.Cmd to 3 inches per second and the Limit.Arm.Movement function is called so that it can provide its protective functions if needed.

Next checking step G16 is executed to determine if the value of State.T has been incremented to 25 ($\frac{1}{4}$ seceond). If not, State.T is incremented, otherwise Model.S is set to 3 and Z.Ref is set to Z.Box. Thus this model state brings the box to a light resting condition on the shelf for at least one fourth of a second.

Model State 3

In this model state, the new Vel.Cmd value is calculated, the value of L.Stop is set to Z.Ref $+1$ inch, the value of Trans.L (transition limit) is set to 0, the Vel.Cmd value is subjected to viscous damping to control movement upward off of the shelf, and the Limit.Arm.Movement function is called. Checking step G17 then checks to see if the value of Z.Box is such that the box is at least one inch above the shelf and if so, sets Model.S to 0. Checking step G18 checks for the box having been slid off the shelf so that Dist.Shelf has a high value and if so, sets Model.S to 4. Model state 3 thus manages removal of the box from the shelf either by lifting it off vertically or sliding it off horizontally.

Model State 4

In this model state, the new value of Vel.Cmd is calculated and the Limit.Arm.Movement function is called. Then model state 1 is set if the three checking steps G19-G21 show that the box is being put back on the shelf. Otherwise, checking step G22 ensures that the value of Vel.Cmd is not less than a negative velocity transition limit and then this transition limit is decremented toward the value of D.Vel.Lim so that the box cannot accelerate downward quickly when slid off the shelf. Once Trans.Lim has been decremented down to or below D.Vel.LIm, checking step G23 returns Model.S to 0.

The next step is to call the Protect.Covers function which will limit the value of Vel.Cmd if the box is being put down on the covers at the base of the shelf brackets to avoid a collision there. Then the value of Vel.Cmd is limited to be between the up and down velocity limits, followed by modifying Vel.Cmd by applying two damping functions in sequence. The purpose of the application of the damping functions is to stabilize the servo system.

The first damping function is based on modelling a viscous damper which is attached to an inertial reference point which is moving with the system at a velocity which is not permitted to differ from the actual box velocity by more than a predetermined fixed amount. The second damping function provides strong anti-oscillation measures for the system. The second damping function has a first step that produces a decay of the previously modelled damping factor toward zero. The next step is to determine if a direction change has occured and if so, the damping factor is incremented by the value of Vel.Change, i.e. the current acceleration value.

Next the routine forces Vel.Cmd to 0 if Dir.F is 1 and Vel.Cmd is less than 0, to provide smooth initial operation of the system as discussed previously.

Figure 30:
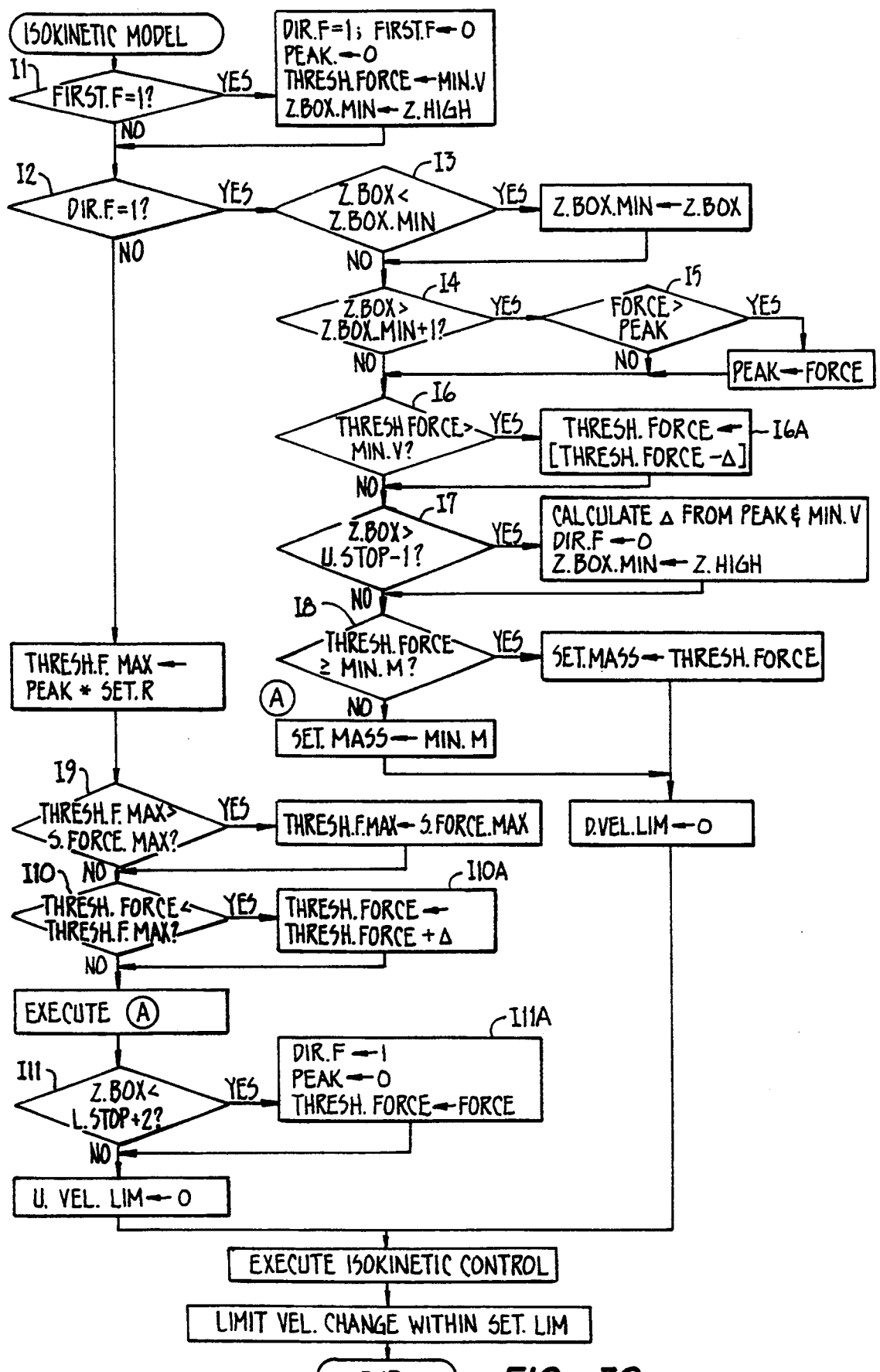
Figure 31:
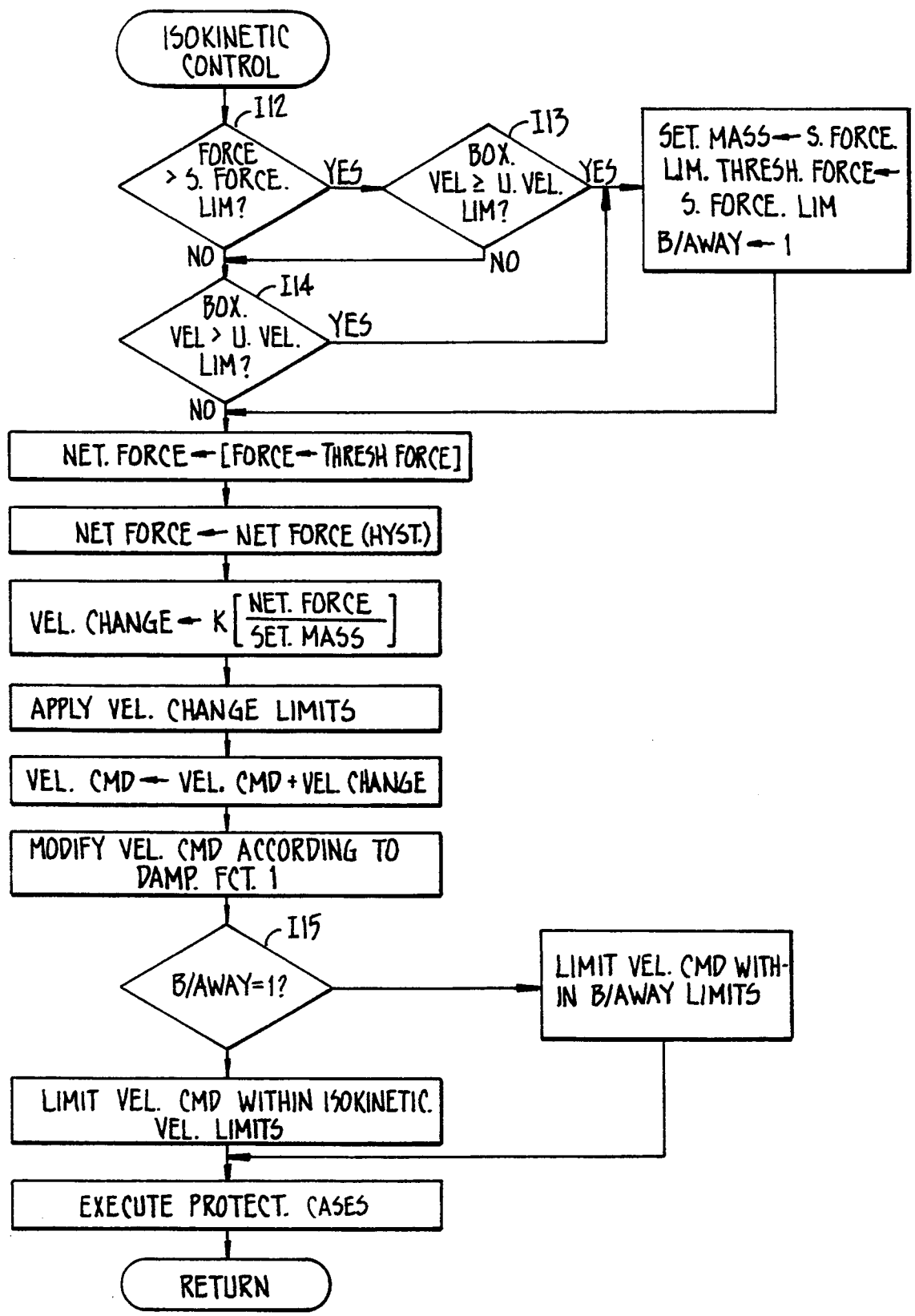

Isokinetic Model (FIGS. 30,31)

For purposes of understanding the software control routine of the Isokinetic Model, it should be explained that the inertial model used here utilizes a threshold force value Thresh.Force and a modelled or simulated mass value Set.Mass which are not always equal to each other. The purpose of this isokinetic lift task is not to simulate the inertial response of an object having a Set.Mass value but to produce an isokinetic upstroke control with concentric muscle loading and an isokinetic downstroke control with eccentric muscle loading. On the first upstroke it is desirable to model a small threshold force value as if lifting a light box so that it is easy to start the box and arm moving upward, but to model a somewhat larger mass to limit the rate of acceleration of the box and arm toward the upstroke isokinetic velocity limit as if the mass of the box were heavier.

On the downstroke, the threshold force value is ramped up toward a maximum threshold force value so that it is easy for the patient to keep the box from moving down initially, but gradually the machine will overcome the patient's upward force with the higher threshold force value (like gradually increasing the weight of the box) and the box will start moving down. Initially the mass value which determines rate of acceleration will be at a minimum value, but as soon as the threshold force value exceeds that minimum value, the mass value will follow the value of threshold force so that the arm and box will accelerate more rapidly toward isokinetic velocity limits.

Now, looking at the steps of the Isokinetic Model software routine, the first step I1 is a checking step to determine if the First time flag is 1. If this returns a YES, then First.F is set to 0, the direction flag Dir.F is set to 1 (up), the Peak.Force parameter is initialized to 0, and the Thresh.Force parameter is set to preselected minimum value Min.V to prepare for upward movement and data collection on peak force. The value of Min.V is preferably equivalent to a small force, e.g. four pounds. Later a parameter called Min.M for minimum mass will be used in the routine and the value of this parameter is preferably four or five times larger, e.g. equivalent to about twenty pounds.

Next checking step I2 is performed on the value of the direction flag Dir.F. If the value is 1, as it is initially (the box or interface being at the value of L.Stop), then the up direction control routine is executed. If the value is 0, the downstroke control routine portion is executed.

Upstroke Control Routine Section

The first step in this routine is checking step I3 which checks on the value of Z.Box, the current height parameter value, to see if it is less than Z.Box.Min. If this returns a YES, then Z.Box.Min is set to the current value of Z.Box. The next checking step I4 is to determine if Z.Box is greater than Z.Box.Min plus one inch. If this returns a YES, then the current Force value is checked against the value of Peak and stored as the Peak value if it is greater than the value already stored. This Peak value of the force exerted by the patient is used in downstroke routine to set the value of the maximum weight and mass for the eccentric downward movement phase of the isokinetic lift exercise. The purpose of these other steps will be explained in the detailed description below of a sequence of repetitions of an isokinetic lift.

The next checking step I6 determines whether the Thresh.Force parameter is currently greater than the value Min.V. and if it is, the value of Tresh.Force is decremented by the value of Delta, which is calculated at the end of the upstroke movement. The purpose of this is to gradually reduce the threshold force to the minimum value to permit easy acceleration to the isokinetic velocity setting on an upstroke movement phase which follows a downstroke movement as described in the example below. The purpose of this will be clear from that description.

Next a cheching step I7 is performed to determine if the box (or other interface device) is getting close to the upper stop position. If this returns a YES, then a value for Delta is calculated from the values of Peak.Force and Min.V, with the algorithm being selected to provide for a substantially constant time delta in ramping the threshold force from the minimum value, Min.V to the value of Peak at the beginning of the downstroke movement. Next the value of Dir.F is set to 0 and Z.Box.Min is set to a preselected high value.

If the checking step I7 returns a NO, checking step I8 is executed to determine if the value of Thresh.Force is greater than or equal to the value of Min.M. If checking step I8 returns a YES, the value of Set.Mass is set to the value of Thresh.Force; otherwise the value of Set.Mass is set to the value of Min.M. The purpose of this will be discussed below in a description of a sequence of operation of isokinetic lift exercise.

Next the value of the down velocity limit parameter, D.Vel.Lim, is set to 0 to preclude downward movement of the arm until the upper stop is reached. In other words the patient is allowed to stop the arm but can not reverse direction until reaching the upper stop.

The Downstroke Routine Section

Now, if the early checking step I2 on the direction flag value returned a NO, the value of the maximum threshold force parameter, Thresh.F.Max is set to the value of Peak multiplied by Set.R which is a ratio parameter which may be a machine parameter (e.g. value 1) or a value allowed to be set by the therapist within some limits. As will be seen this models a maximum mass (inertia) and weight value for the downstroke which is a multiple of the peak force measured on the upstroke, i.e. making it feel like a heavy box or object to be lowered on the downstroke as an eccentric load.

At this point checking step I9 is performed to determine if the value of Thresh.F.Max is greater than the maximum force value entered by the therapist, and if it is, Thresh.F.Max is then reset to the value of S.Force.-Max. The next portion of the routine, steps I10 and I10A, checks the value of Thresh.Force relative to the value of Thresh.F.Max and increments it by Delta if it is less than Thresh.F.Max. At this point, if desired, the new value of Thresh.Force can be limited to be no higher than Thresh.F.Max in case the addition of Delta increased it above that value.

The purpose of this is simply to ramp the value of Thresh.Force up toward the maximum threshold value so that the amount of upward force that must be exerted by the patient to stop the descent of the box is gradually increased and will eventually exceed the force being exerted by the patient to start the box moving down.

Next the sub-routine A is exectuted as described in connection with the upstroke section of the Isokinetic Model. While the value of Thresh.Force is below the value of Min.M, the value of Set.Mass used to determine rate of acceleration will be kept at Min.M, but as soon as the value of Thresh.Force exceeds Min.M, Set.-Mass will be set equal to Thresh.Force, so the two parameters will ramp up together toward the value of Thresh.F.Max.

Next checking step I11 is performed to determine if the box is close to the lower stop, and if it is, the value of Dir.F is changed to 1 (for up), Peak.Force is reset to 0 and Thresh.Force is set to Net.Force as the starting value for the upstroke. Then, the value of U.Vel.Lim is set to 0 so that the only permitted direction of movement is down and the isokinetic control routine is executed.

Isokinetic Control Routine (FIG. 31).

The first portion of the Isokinetic Control routine involves a set of checking steps I12, I 13, and I14 for determining if the system is in a breakaway condition. The initial checking step I12 determines if the value of Force is greater than the value of the set force limit entered by the therapist. If this returns YES, then a second checking step I13 is performed to determine if the value of Box.Vel is greater than or equal to the value of the set isokinetic upward velocity limit entered by the therapist. If both of these conditions are true, then the system is in a breakaway condition and the breakaway flag is set to 1 and the values of both Set.-Mass and Thresh.Force are set to the value of S.Force.-Limit set by the therapist. As the rest of the routine executes, these new settings will permit a slow acceleration of the box and arm above the isokinetic velocity limit toward the breakaway velocity limits.

If checking step I12 returns a NO, then checking step I14 executes to determine if the value of Box.Vel is greater than the value of U.Vel.Lim, the upward isokinetic velocity limit set by the therapist. If this returns a YES, then the system is in a breakaway condition also and the same steps are executed as above.

The next step is to calculate Net.Force by subtracting the value of Thresh.Force from the value of Force (i.e. the patient exerted force).

The next step is to add some hysteresis to the value of Net.Force to make the behavior of the system more stable in the event of rapid changes of force applied by the patient. This is done by comparing the current value of Net.Force with the stored last value. If the current value differs from the last value by less than a preselected delta value, e.g. two pounds, then the current value is reset to the last value. If the current value differs from the last value by more than the delta, the current value is reset to the last value plus the delta value and that is stored as the last value. So for example, if the last value were ten pounds and the new value were 100 pounds and the delta were two pounds, Net.-Force would be set to twelve pounds and last value would be set to twelve pounds. Then if the next time through the value of Net.Force were eleven pounds, it would be reset to the last value of twelve pounds.

Then the inertial model is executed to determine the value of Vel.Change and then Vel.Change limits are applied to limit the acceleration, e.g. between $+/-1$ g. Then the value of Vel.Cmd is incremented by the value of Vel.Change, followed by application of damping function 1 as described above in connection with the Gravity/Inertia Model.

The value of B/Away.F is then tested in checking step I15 and depending on the value returned, Vel.Cmd is either limited between breakaway limits or between isokinetic velocity limits set by the therapist. Then a machine safety routine to protect from running into the cases covering the base of the shelf ladders is executed. This routine would not be present in any less fully featured embodiments of the invention which did not use shelves.

An Example of Isokinetic Model Execution

To illustrate operation of the Isokinetic Model, assume the following parameters are set by the therapist.

| | |
|---|---|
| L · Stop | 10 inches |
| U · Stop | 50 inches |
| U · Vel · Lim | 30 in./sec. |
| D · Vel · Lim | 20 in./sec. |
| S · Force · Lim | 80 pounds (upstroke) |
| S · Force · Max | 120 pounds (downstroke) |
| Set · R | 150 percent |

Also assume that the factory set parameters are

| | |
|---|---|
| Min · V | 4 pounds |
| Min · M | 20 pounds |
| Hyst · Val | 2 pounds |
| Z · Box · High | 80 inches |

The lift exercise routine will start with the arm at the lower stop value, Z.Box=ten inches and the First.F value of 1, so the isokinetic model will first initiaize the parameters as shown and the value of Thresh.Force will be four pounds and the value of Dir.F will be 1. The next checking step on the value of Dir.F will return Y, and the next checking step on the value of Z.Box will return Y, so the value of Z.Box.Min will be set to Z.Box or ten inches. The next checking step on the value of Z.Box will return N since there is no upward movement yet, so the next checking step on the value of Thresh.Force will be executed and will also return N.

The following checking step on the value of Z.Box will return N since we are not close to the upper stop and the following checking step on the value of Thresh.Force will return N since it is still at Min.V which is less than Min.M. Consequently, Set.Mass will be set to Min.M, followed by seting D.Vel.Lim to 0, and the isokinetic control routine will execute. Let's assume that the patient has applied a force of plus six pounds. Both checking steps related to breakaway conditions will return Ns, so the value of Net.Force will be calculated and return a value of two pounds. Applying hysteresis will produce a net force of two pounds and the value of Vel.Change will be calculated using a Set.Mass of twenty pounds. The value of Vel.Cmd will be incremented by the value of Vel.Change and the box and arm will respond by starting to move upward.

The next time through the Isokinet Model routine, essentially the same execution path will be followed, except Z.Box will be greater than Z.Box.Min so the checking step I3 will return N. This execution path will continue until the box has moved up an inch, at which time the peak force capture steps are executed each time. Assuming the patient keeps an upward force on the box, the box will accelerate upward until the isokinetic velocity is reached. Then further acceleration will not occur unless the value of S.Force.Lim is exceeded. The Isokinetic Control routine will limit the velocity to the U.Vel.Lim of thirty inches per second.

If the patient stops exerting upward force above the value of Min.V, the box will slow below the isokinetic velocity limits and eventually stop, but will not drop. If the patient continues to push up, the routine will execute on the same path until the value of Z.Box exceeds 49 inches. Let's assume the patient has exerted a peak upward force of sixty four pounds. The next time through the routine, I7 will return a Y, the Delta will be calculated, Dir.F set to 0, and Z.Box.Min set to 80 inches. Let's assume that Delta is calculated by subtracting the value of Miv.V from Peak and dividing by 20 so that Delta is 1.5.

The next time through the routine, I2 will return N, so the value of Thresh.F.Max will be set to 150% of Peak or 96 pounds. This is below S.Force.Max of 120 pounds to I9 will return N. Now the value of Thresh.Force is still Min.V or four pounds, so I10 returns Y and Thresh.Force is incremented by 1.5 pounds. As long as the patient is still pushing up on the box the box will stay at the upper limit and not start to fall until this routine has executed enough times for steps I10 and I10A to ramp the value of Thresh.Force up to exceed the upward force exerted by the patient. Then the box will begin to be accelerated down by the system until isokinetic down velocity is reached. The value of Thresh.Force will keep increasing with the value of Set.Mass at Min.M (20 pounds) until Thresh.Force exceeds 20 pounds, and then subroutine A will cause Set.Mass and Thresh.Force to ramp up in value together until both are at or close to Thresh.F.Max or 96 pounds. Then no further ramping will occur.

It will be appreciated that the use of steps I10 and I10A to increment the value of Thresh.Force instead of immediately setting its value to Thresh.F.Max avoids sudden application of a perceived heavy eccentric load on the patient and builds up that load gradually for patient safety and comfort.

AS long as the patient isn't exerting an upward force larger than the value of Thresh.Force, the box will accelerate down to the D.Vel.Lim of 20 inches per second and maintain that speed. If the patient exceeds the value of Thresh.Force then the box will slow and eventually stop, but not move upward. The box will drop until Z.Box is less than L.Stop plus two inches or twelve inches in this case. Then step I11 will return Y instead of N, and step I11A will execute to reset the value of Peak, change the Direction Flag value and set the value of Thresh.Force to Force, i.e. the value of the force that the patient is exerting in the upward direction as the lower limit is reached. Let's assume the patient is still exerting 40 pounds of upward force so Thresh.Force is set to 40.

The next time through the routine, I2 will return Y, and I3 returns Y, so Z.Box.Min is set to Z.Box. I4 returns N, but I6 returns Y since Thresh.Force is 40 and Min.V. is 4. Step I6A executes to decrement the value of Thresh.Force by 1.5. If the patient is still exerting 40 pounds, the value of Net.Force calculated in the Isokinetic Control Routine will be 1.5 pounds which will start the upward acceleration, but at a slow rate. Subroutine A will keep setting the value of Set.Mass to the value of Thresh.Force until the routine has executed enough times at 100 Hz rate to return Thresh.Force to Min.M or 20 pounds. Then the Value of Thresh.Force will continue to decrement toward Min.V of four pounds, but Set.Mass will stay at 20 pounds.

By setting Thresh.Force equal to the actual patient applied force at the end of the downstroke and then decrementing both Thresh.Force and Set.Mass toward their respective minimum values, a smooth transition between the downstroke and upstroke movement is achieved. It will be appreciated that if Thresh.Force were reset to Min.V immediately on the start of the upstroke and the patient has been applying a large upward force, Net.Force would suddenly increase in value, producing a sudden acceleration of the box upward and this is undesirable from a patient safety and comfort standpoint.

Special Examples

The preferred embodiment of this invention shown in the Isokinetic Control routine of FIG. 31 includes provision for the therapist to set a S.Force.Lim value related to the upstroke and a S.Force.Max value related to the downstroke. This allows the therapist to protect the patient from overexertion by allowing the machine to exit from isokinetic velocity limits if the patient is pushing up with a force higher than the S.Force.Lim during the upstroke. However, the Isokinetic Control routine only declares a breakaway condition if the patient exerted force exceeds this therapist set maximum at a time when the Box.Vel value is at or above the set isokinetic velocity limit. This eliminates entering a breakaway condition if, for example, the patient were to jerk up hard on the box at the start of the upstroke before the box started moving up.

Variations in Implementation

It should be understood that variations could be introduced into this routine if desired. For example, during the upstroke, the routine might include a check on whether the patient has stopped moving up for one second before reaching the upper stop position and switch to the eccentric loading downstroke at that time. The routine could include a programmable pause period at the end of each stroke portion if desired. On the downstroke, the routine could include a breakaway to upstroke isokinetic movement if the patient pushed up at greater than the threshold force value after isokinetic velocity were reached.

Instead of calculating a Delta value, this could be a set parameter that would provide a smooth ramp and reasoanble transition conditions under most circumstances of operation. A Concentric/Concentric control routine could be implemented if desired.

Figure 32:
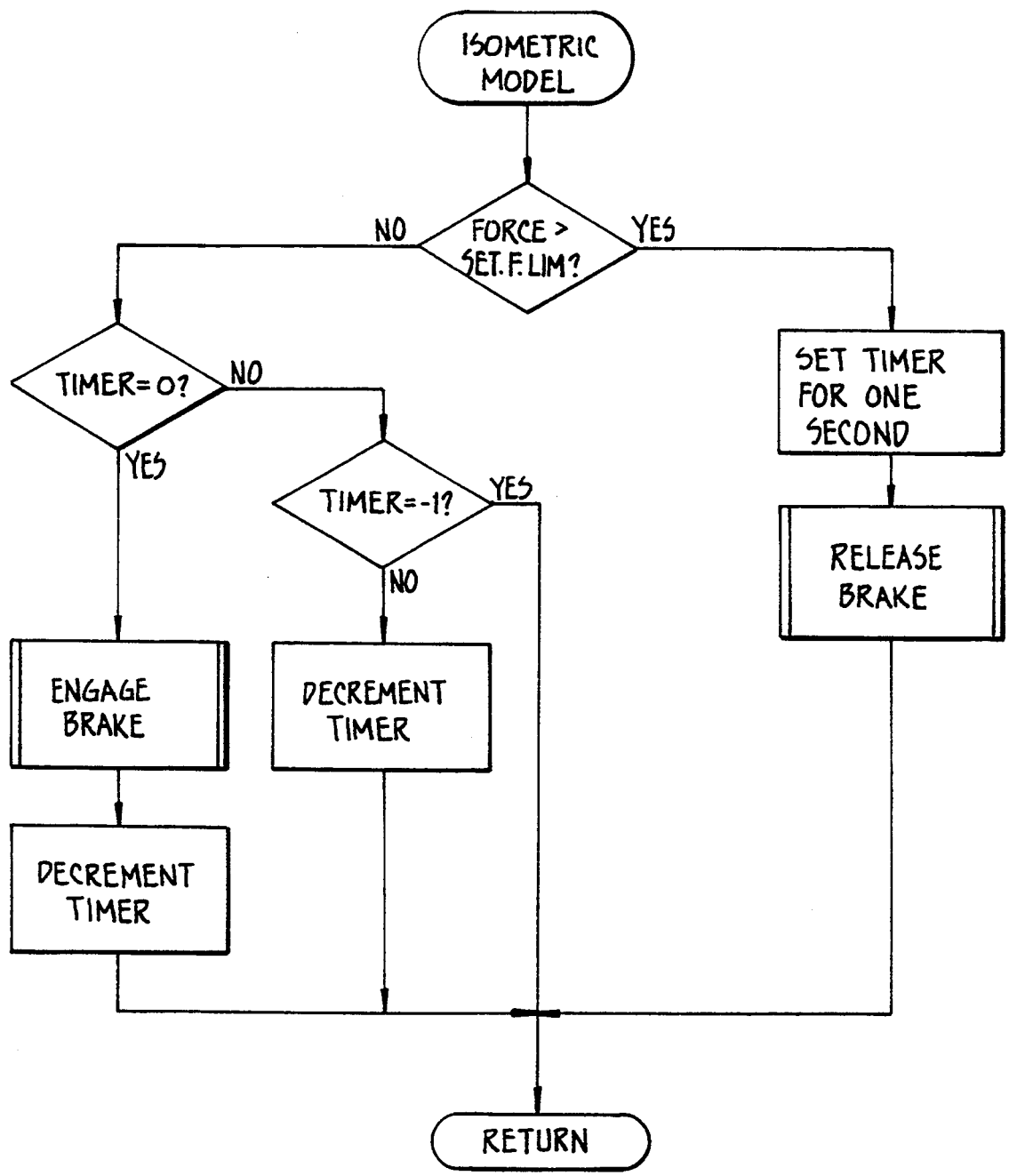

Isometric Model (FIG. 32)

The isometric mode of operation of the lift system of this invention is mainly controlled by commands from the host processor. The host commands movement of the arm to the location at which the isometric lift is to be performed and then shuts off the motor sets the timer to zero. The controller software is mostly taking data on the force exerted by the patient and sending it back to the host.

The isometric model shown in FIG. 32 illustrates that controller software is monitoring the applied force and if it exceeds a set force limit value entered by the therapist, the the brake is released for one second and then reengaged if the force has dropped below the set force limit. Although the motor has been turned off, the arm of the lift system can move slowly when the brake is released and this will tend to unload the excess force that the patient is applying to the system.

Figure 33:
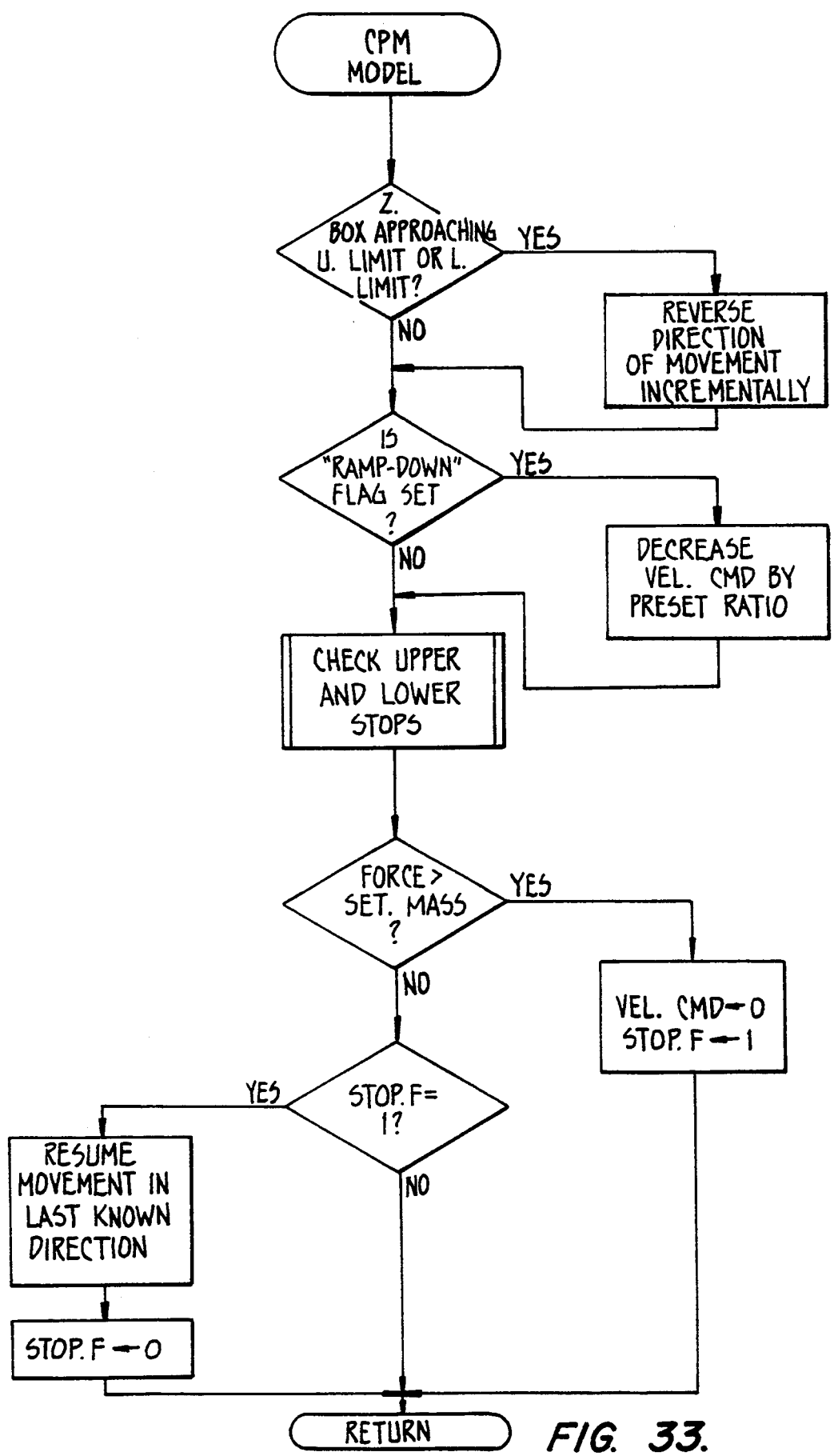

CPM Model (FIG. 33)

The purpose of the CPM Model is simply to control the arm of the lift system to move at a selected velocity between a set upper limit value, U.Limit, and a set lower limit value, L.Limit. At the turn around points the arm is decelerated to a stop and then accelerated toward the selected velocity. Referring to FIG. 33, the first step is a checking step to determine if the value of Z.Box, the position of the arm, is approaching one of these limits. If it is approaching a limit, then the Vel.Cmd parameter is modified to start reversing the direction of movement of the arm and to accelerate it in the other direction toward the set Vel.Cmd value. Otherwise the set Vel.Cmd value remains the same.

The next checking step determines if a Ramp Down flag has been set by some action of the Host, such as completion of the number of repetitions of the up and down movement or by the therapist hitting the escape key to stop the exercise. If this flag is set, then the value of Vel.Cmd is decreased by a preset ratio to bring the arm to a stop.

The Check Upper and Lower Stops routines examines the value of Z.Box and if it equals the value of L.Limit or U.Limit the Vel.Cmd value is set to 0 to make sure the the limit is not exceeded. The next checking step compares the value of Force to the value of Set.Mass and sets the value of Vel.Cmd to 0 and sets a Stop.F flag to 1 if the Force is higher than Set.Mass. This permits the therapist to set a maximum force limit that the patient can exert on the system before it will come to a stop. Following this a checking step is executed to determine if the Stop.F flag is set, and if it is, the value of Vel.Cmd will be incremented to start the arm moving in the direction it was going prior to being stopped and the Stop.F flag is reset to 0. From these two checking steps, it can be seen that as long as the excess force is applied, the arm will remain stationary, but when the excess force is removed, the arm will begin to move again in the direction it was moving before being stopped by excessive force.

Figure 34:
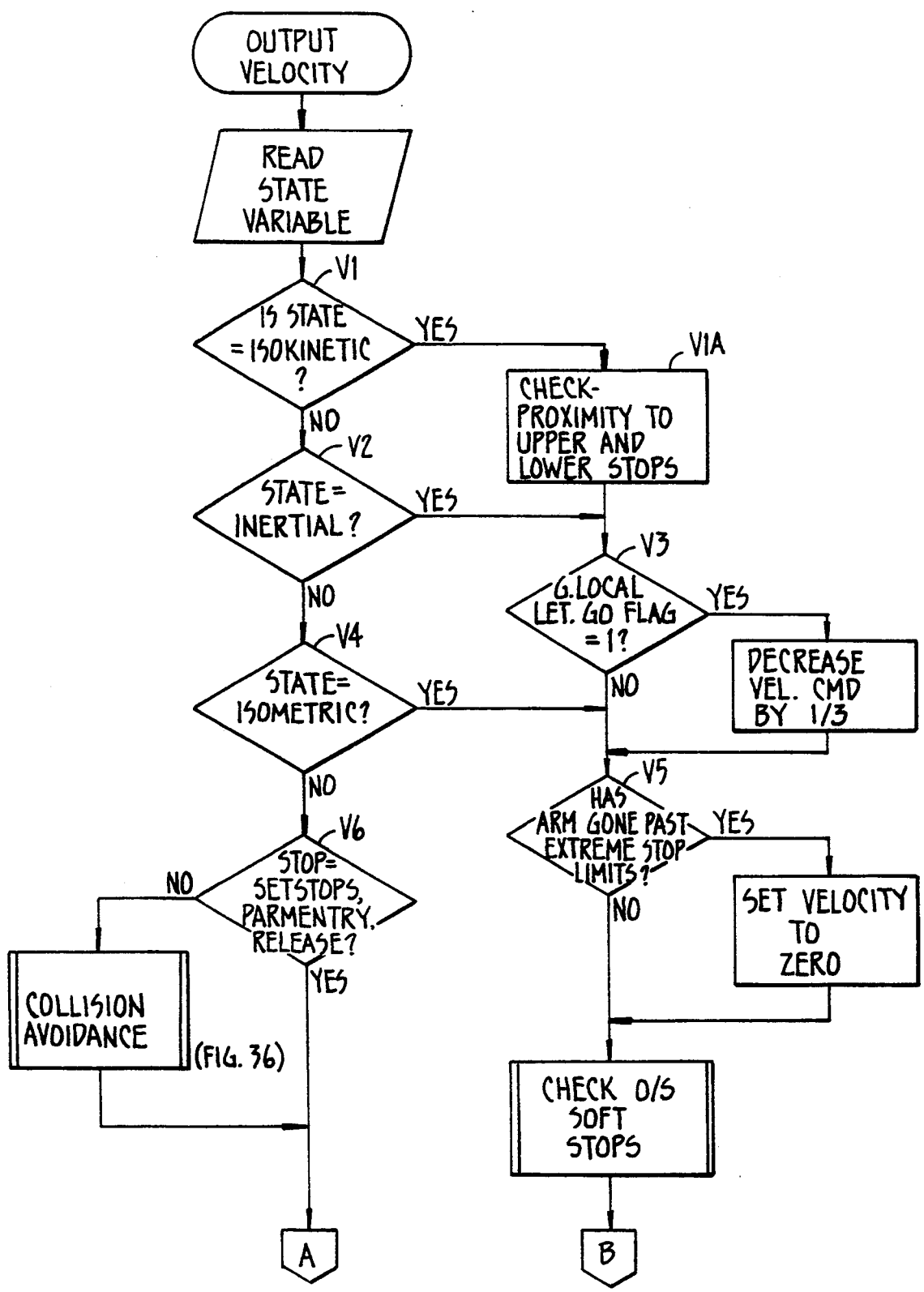
Figures 35, 36:
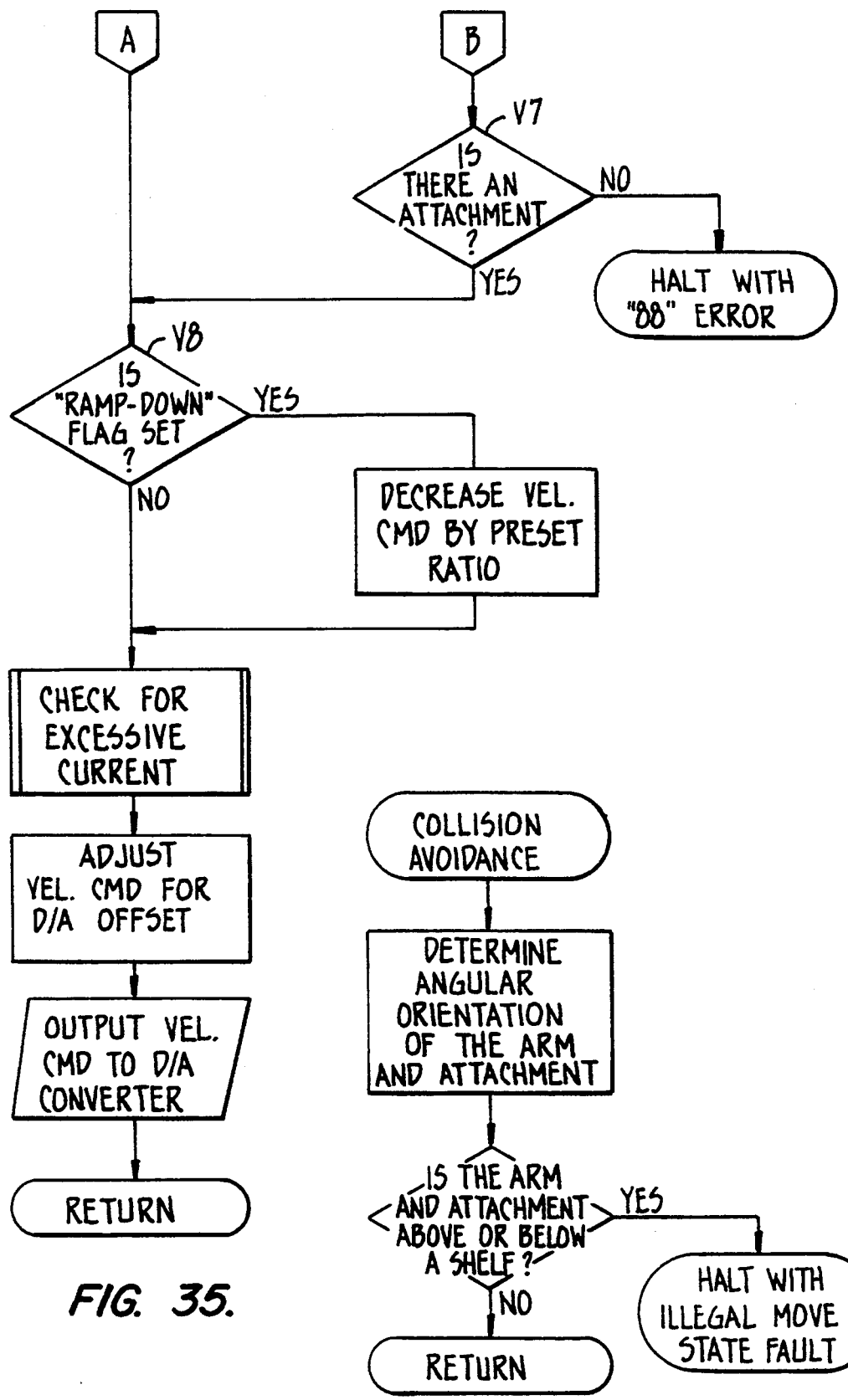

Output Velocity Routine (FIGS. 34, 35)

The Output Velocity routine shown in FIGS. 34 and 35 is executed each time at the very end of the On 100 Hz module. The purpose of this routine is to do further processing of the value of the velocity command parameter, Vel.Cmd, which has been passed to it by the state related routine that has just finished being executed. The first step of the routine is to read the state variable. Then checking step V1 is executed to determine if the state is Isokinetic. If this step returns a YES, then a routine is executed to check the proximity of the box or other attachment to the upper and lower soft stop values and changes the Vel.Cmd value to decelerate the box if it is close to a stop position. This can be done in a number of ways, e.g. by calculating the difference between the Z coordinate of the box and the stored Z coordiante of the the stop and using that value to address a look up table for the maximum allowable velocity at that distance. Then the value of Vel.Cmd can be compared with that maximum value and set to that maximum value if it is greater than it.

If checking step V1 returns NO, checking step V2 determines if the state is inertial (associated with the Gravity/Inertia mode. If a YES is returned by step V2 or if both steps V1 and V1A have executed, checking step V3 is executed to determine if the value of the Let.Go flag is 1, meaning it has been set during execution of the Let Go Detection routine of FIG. 45. If checking step V3 returns a YES, then the velocity command Vel.Cmd is reduced by one third to slow the descent of the box or attachment each time this routine executes. Eventually the dropped box or attachment will slow down to a very low velocity until a lower stop position is reaached.

If both checking steps V1 and V2 return NO, then checking step V4 determines if the state is Isomentric. If V4 returns a YES, or if either of steps V1 or V2 returned YES, then checking step V % is executed to determine if the arm has gone past extreme stop limits set into the system as a machine variable. This is a backup to the use of the upper and lower hall effect limit switches which will be triggered by travel of the arm to extreme Z coordinate positions. This checking step would actually involve separate comparisons of the current Z.Box value with the stored upper and lower max limit values. If V5 returns YES, the value of Vel.Cmd is set to zero so the box will not move any further.

If checking step V5 returns a NO, then a routine is executed to determine if the value of Z.Box is outside the upper and lower stop limits, i.e. the box actually went past the defined soft stop. This routine sets a Halt state if it detects that the box is outside the therapist defined limits.

Next checking step V7 (FIG. 35) determines if there is an atteachement actually mounted on the arm. This is done by looking at the values of the two hall effect sensors associated with signalling the type of attachement on the arm. If both sensors are untriggered, that means that no attachment is on the arm and the system is halted. This is an important step, because if the attachment has been removed after the baseline compensation step was performed, for example, the value of Net.- Force is no longer valid and reliable system operation cannot be assured.

Referring back to FIG. 34, if all of the checking steps V1, V2, and V4 return NO, then checking step V6 is executed to determine if the system is in any of the states Setstop, parmentry, or release, and if this returns NO, a shelf collision protection routine shown in FIG. 36 is executed.

Now regardless of the execution path taken by this routine, checking step V8 is executed to determine if the Ramp.Down flag has been set. This flag will be set by a command from the host under a variety of conditions, such as if the therapist hit the ESC key to halt the exercise or if the host computer has deterined that the accumulated work set by the therapist has bene completed. If V8 returns YES, the value of Vel.Cmd is decreased by a preset ratio to gradually bring the arm and box to a stop.

Following this a routine to check for excessive motor current is executed. This is done by looking at the value of the current signal from the Power Amp. If current is excessive, the machine is halted. Next a routine is executed to adjust the value of Vel.Cmd to account for the offset of the digital to analog converter and then the Vel.Cmd value is sent to the D/A converter to be converted to an analog signal into the power amplifier.

If a position based controller such as disclosed in the above referenced Dempster et al. patent application were used, this Vel.Cmd signal would be further processed to develop a POS. Cmd signal to send to the power amp.

Collision Avoidance (FIG. 36)

The collision avoidance routine of FIG. 36 reads the current angular orientation of the arm of the lift system, i.e. the Theta coordinate and then uses that value, together with the attachment information stored in memory to determine if the arm and attachment are in a position above or below a shelf. If the associate checking routine returns a YES, then the system is halted with an Illegal Move State fault.

Safety Checks (FIG. 37)

This safety checking routine is called from the Data Acquisition routine of FIG. 27. The first step of this routine is to calculate a value for Force.Est from the values of Arm.Length and Arm.Torsion. This is an estimated force value based on the dividing the arm torque as reported by the secondary load cell on the arm by the length of the arm which is determined from the value of the arm length potentiometer. Then a value for Force.Error is calculated from the values of Force.- Est and Lift.Force. Following this a checking step determines if the arm is moving actively and all of the safety check routines except the Tach-Position Check routine are bypassed if the arm is not moving actively in one of the exercise modes.

Force Cross Checks Routine

If the arm is moving actively, the Force Cross Checks routine is executed. Basically, this routine looks for a Force.Error value greater than a preselected amount (e.g. 30 pounds) which has lasted for a preselected time duration (e.g. 100 msec). If thses conditions are met, then the system is halted with a Force Check error declared. This routine also calculates the slope of the change in the calculated Force.Error value and if that slope exceeds a preselected error value (e.g. 0.25 pounds/msec) while the arm is moving downward at a velocity greater than a preselected velocity threshold and these two conditions last for more than a preselected time duration (e.g. 40 means), then the system is halted with an Error Slope fault declared. This type of error would be produced if a force is applied to the arm other than at the the point of attachement at the end of the arm. This would occur, for example, if the arm were coming down on an object interfering with arm travel.

Position-Velocity Check

This routine estimates the velocity of the arm as measured by successive position values from the optical encoder and checks that against the value of the Vel.Cmd signal being set to the power amplifier to drive the servo motor. This checking routine looks for both positive and negative cross check errors lasting for more than a preseleted duration of time (e.g. 100 msec) and if one is detected the system is halted with a Position-Velocity Error declared.

Velocity-Tachometer Check

This routine checks the value of Vel.Cmd against the value of actual velocity reported by the tachometer. If a cross check error of a preselected larger amount occurs throughout all of a shorter preselected time duration or a cross check error of a preselected smaller amount occurs throughout all of a longer preselected time duration, then the system is halted with declaration of a Velocity-Tach Error.

Tachometer-Position Check

This routine checks the value of actual velocity as determined from change in position reported by the optical encoder output with the value of actual velocity as reported by the tachometer. If these two values disgree by a prselected amount for more than a preselcted time duration, then they system is halted with a Tach-Position Error declared. This routine also checks the position change value against a preset maximum position change value and if that maximum position change value is exceeded, the system is halted with a Delta-Position Error declared.

Figure 38:
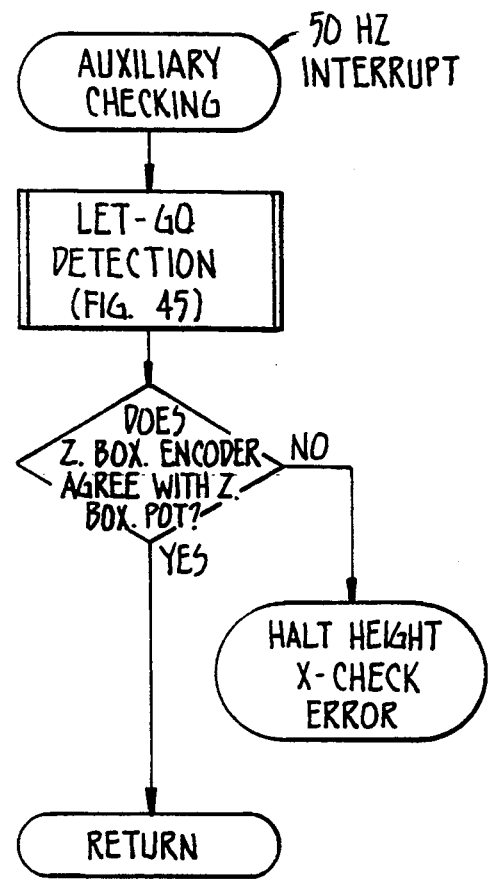

Auxiliary Checking on 50 Hz Interrupt (FIG. 38)

Figure 45:
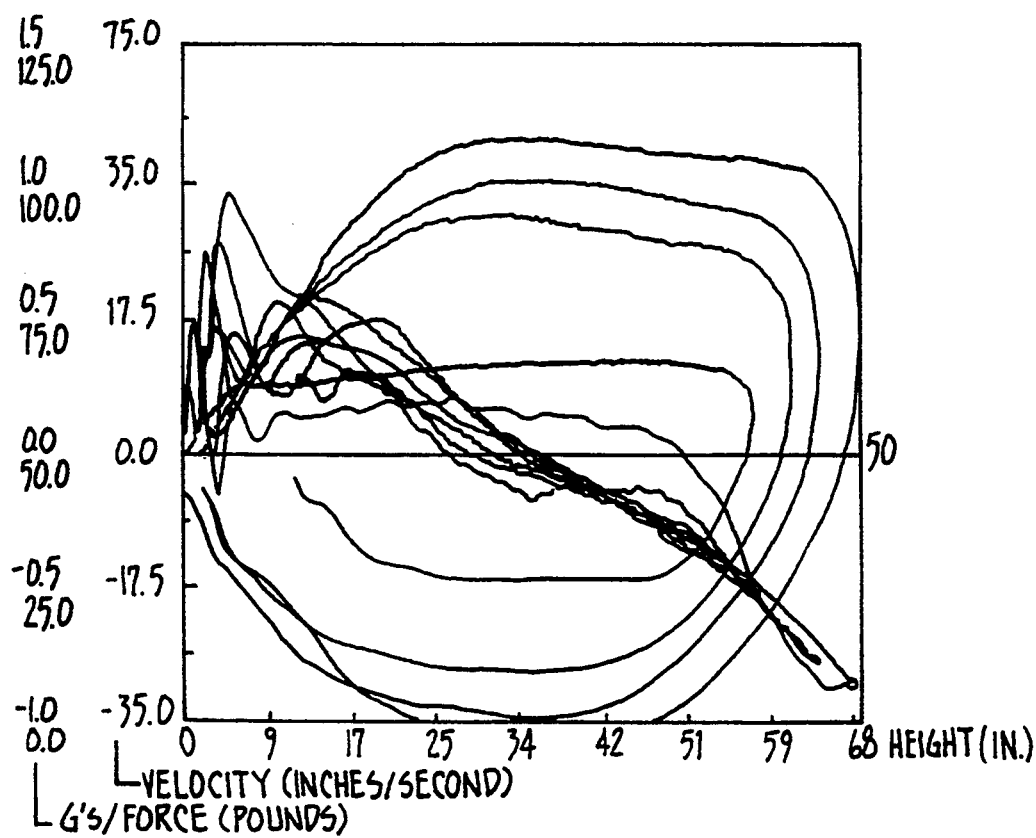

This auxiliary checking routine executes on each tick of the 50 Hz interrupt clock. First the "Let-Go" Detection routine of FIG. 45 is executed. Then a checking routine is executed to determine if the value of Z.Box- .Encoder (i.e. the height of the arm as determined by the rotary position encoder 180) agrees with the value of Z.Box.Pot (i.e. the height of the arm as measured by the arm height potentiometer 363). At some point prior to the start of an exercise routine, the value of Z.Box- .Encoder is initialized to be equal to the value of Z.Box.Pot. Thereafter the height delta changes reported by the rotary position encoder are added to the initialized Z.Box.Encoder value as a separate tracking on arm height. If these two height measurements do not agree within a preset margin of error, then the system is halted with a Height Cross Check Error declared. This error condition could be produced by failure of the rotary position encoder or failure of the A/D converter.

Figure 39:
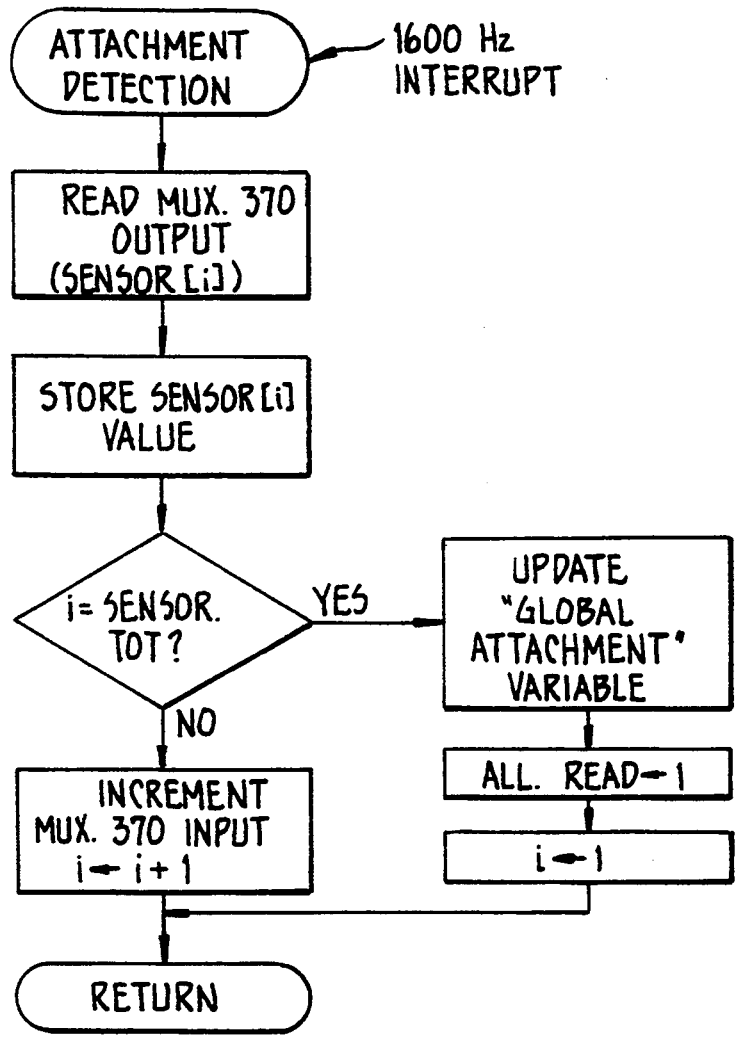

Attachment Detection on 1600 Hz Interrupt (FIG. 39)

This routine executes on each tick of the 1600 Hz clock to read the value of the sensor output currently at the output of the Multiplexor 370 (FIG. 19). This single value is then stored temporarily and then a checking step is executed to determine if the value of i equals the total number of sensors to be read. If this returns YES, then the Global Attachment variable is updated based on the values of the two sensors associated with the attachement mounted on the end of the arm. The All.-Read flag is set to 1, and the value of i is reset to 1. If this checking step returns a NO, then the Mux.370 input is incremented by one so the next sensor value will be read on the next 1600 Hz clock tick.

Referring back to the Data Acquisition routine shown in FIG. 27, it will be seen that the All.Read flag is reset to 0 by this routine after all the termporarily stored attachement data is stored in the memory of the controller.

Figure 40:
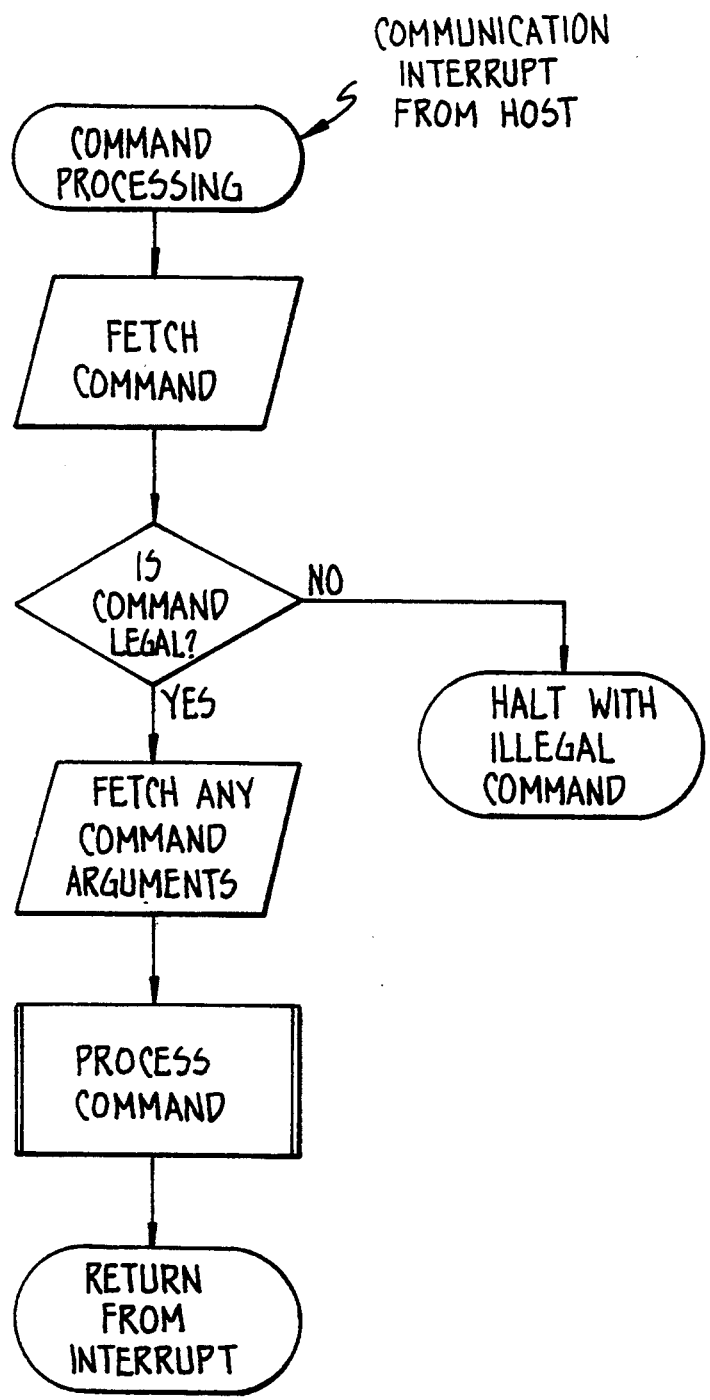

Command Processing—Host Communication Interrupt (FIG. 40)

The command processing routine shown in FIG. 40 is executed when the Host computer sends an communication interrupt to the controller. This routine fetches the command coming from the Host, and then checks its legality by comparing it to valid commands stored in the memory of the controller system. If the command is not a legal one, the system is halted with an Illegal Command declared. If the command is a legal one, any command arguments which are associated with the command are fetched from the Host. For example,if the command is to go to a particular Z.Box location, the command argument is the location to which the arm is to be moved. After the command and argument are available, the command is processed. Processing of the command may, for example, result in a change of the State Variable so that the On 100 Hz Routine will call a different routine.

Figure 41:
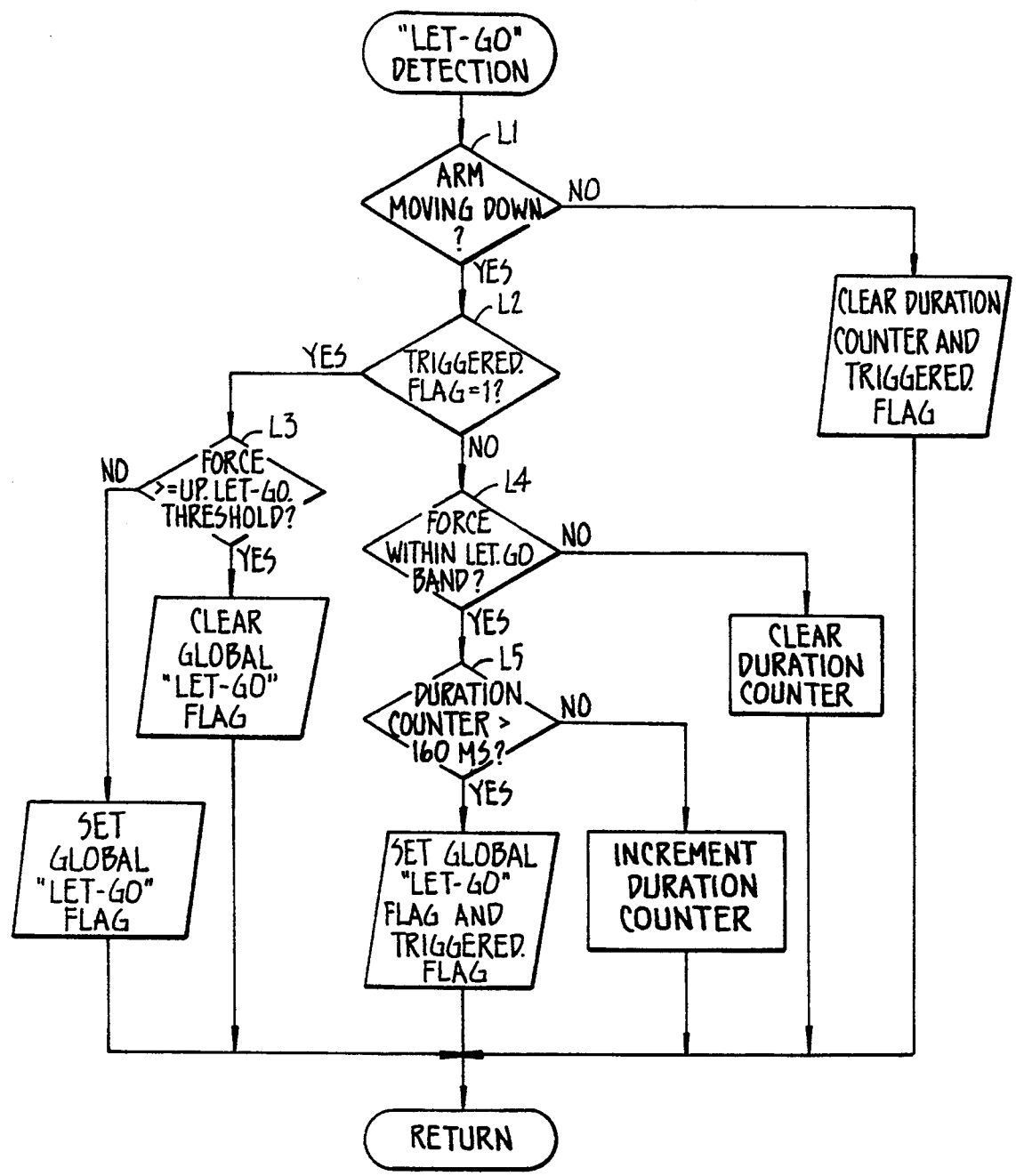

"Let Go" Detection Routine (FIG. 41)

The "Let Go" Detection routine is executed during the 50 Hz Interrupt routine and operates to determine if the patient has let go of or dropped the box or other attachment during the execution of either an Isokinetic Lift task routine or a Gravity/Inertia lift task routine. If the lift task system is in the Gravity/Inertia model, dropping the box results in the Net.Force value in the algorithm in which acceleration is calculated becomes a negative number equal to the Box.Weight set by the therapist which will produce a downward acceleration of the box as if it were falling freely through space. This "Let.Go" routine prevents this free fall of the box from happening. Similarly, if the system is in the Isokinetic mode and the patient drops the box or other attachment during the downstroke portion of the operation of that mode, the attachment will accelerate downward toward isokinetic velocity limits. The "Let Go" detection routine prevents this from occuring.

Referring to FIG. 45, the first checking step L1 of this routine determines if the arm is moving downward. If it is not, then there is no concern about a let go condition and the duration counter is cleared to a zero value, the Triggered Flag is reset to zero, and that completes execution of the routine on that 50 Hz clock tick.

If the L1 checking step returns YES, then checking step L2 is executed to determine if the Triggered Flag has a value 1 due to being set to that value during a prior execution of this routine. If step L2 returns YES, then checking step L3 is executed to determine if the Let Go condition has been removed. Step L3 compares the value of Force to the Up.Let-Go.Threshold value and if Force equals or exceeds that threshold, then the Global Let-Go Flag is cleared to zero but the Triggered Flag is not reset to zero. If the Force is less than that threshold, then the Global Let-Go Flag is again set. From this it can be seen that, once the Let-Go condition has been detected, the Triggered Flag will remain set until the arm starts moving up, and the Global Let-Go Flag will remain be at a zero value only if the patient continues to exert upward force greater than the Up.Let-Go.Threshold.

Now, referring back to checking step L2, if this returns NO, then checking step L4 is exeuted to determine if the value of Force is within the Let.Go Band, i.e. is Force less than a small Up.Let-Go.Threshold value but greater than a small Down.Let-Go.Threshold value. In otherwords, this step determines whether the patient is putting any substantial amount of upward or downward force on the attachment. If step L4 returns NO, this means that a Let-Go condition does not exist and the Duration Counter is cleared to complete execution of the routine. If step L4 returns YES, then checking step L5 is executed to check the value of the Duration Counter to see if it exceeds a number equivalent to 160 milliseconds. If this step returns NO, the duration counter is incremented to complete execution of the routine. If this step returns YES, then a Let-Go condition is declared by setting both the Global Let-Go flag and the Triggered Flag to a value of one.

Referring back to the Output Velocity routine (FIG. 34) it will be remembered that this routine checks the value of the Global Let Go Flag if the State Variable is either Isokinetic or Intertial and if the value of the flag is ONE, the value of Vel.Cmd is reduced by one-third of its value. As long as the Globa Let-Go Flag remains set, the arm will not accelerate downward but will actually decelerate toward a zero velocity. However, if the Let-Go condition is removed, the system will revert to its former operation.

Lift Task Test Set Up and Results Data

Lift task test selections and entry of test parameters is done on host computer 16 in accordance with a user interface which incorporates a series of menus. The provision of a particular user interface based on the technical features shown in the drawings and described above is well within the skill of the average programmer. To illustrate portions of one embodiment of such an interface and the test results that may be achieved with the system and method of this invention, reference is made to Tables 1–5 attached, together with FIGS. 42–45 and a sample test report in Appendix A.

Isometric Lift Tests (Table 1 & Appendix A)

Table 1 illustrates a Run Protocol screen for an Isometric test and illustrates some of the therapist selectable parameters which may be entered. The patient interface "Device" may be selected from a menu of available devices which will pop up on the screen when the cursor is placed at that field and an edit command is given. Similarly the "Grip" parameter may be entered and the Max Force parameter at which the system will release the brake and allow the arm to move upward.

Under the "Stops" section, the therapist can program three different stop locations and label them Arm, Leg, or Torso, referring to three standard lift test positions for isometric lift tests. For each of the three different Stop locations, the therapist can program the Height: the Z-axis coordinate at which the isometric lift will be executed; the Pause: the number of seconds of pause between each repetition at each position; the Duration: the period of time over which force data is taken during each repetition; and the Reps: the number of repetitions at each of the stop positions.

Under "Run Time Options" the Shelves and Feet positions are False or Off since these have no relevance to this type of test. The "Stops" option is True or On since this is relevant to this type of test. The "Biofeed" (i.e. patient biofeedback) option is set to Force Bars, meaning that the amount of lift force being exerted during each lift will be displayed to the patient in real time on the CRT screen of the host computer 16. This is the relevant patient biofeedback display for this type of test.

Appendix A illustrates the reporting of some of the results from an isometric test, giving the average of the maximum lift force exerted over the three repetitions at arm and leg positions and the coefficient of variation (CV) for the three reps.

Figure 42:
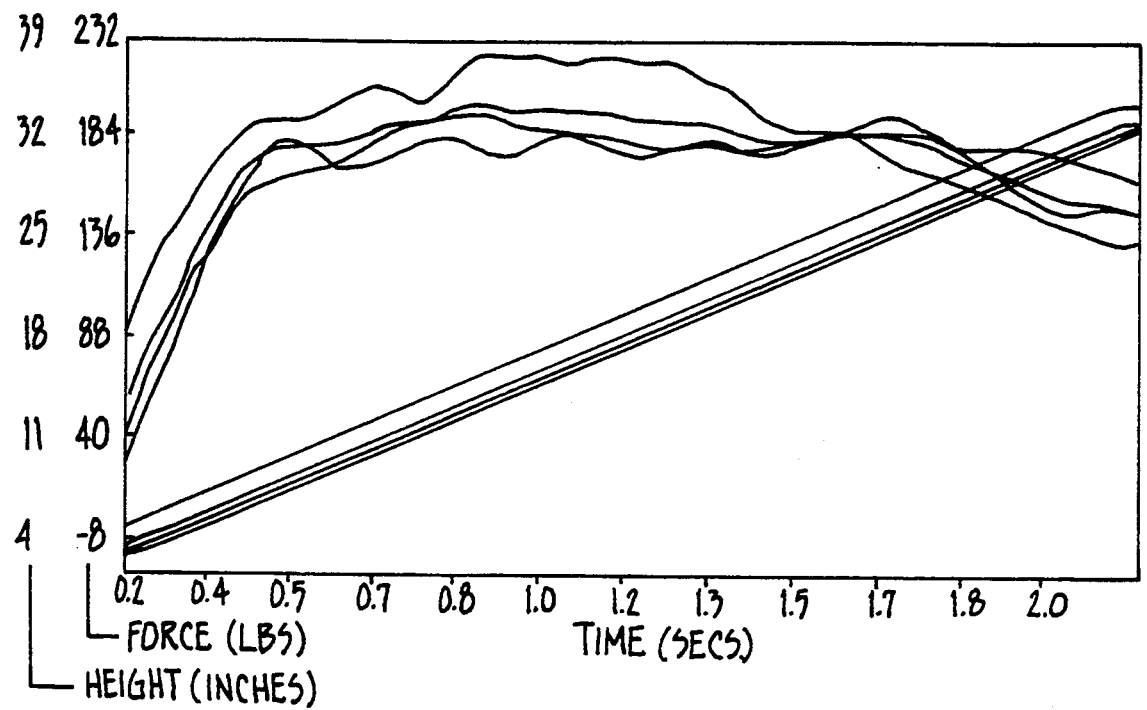
FIGS. 42-45 are pictorial illustrations of various graphs and screen displays produced in a host computer system in one embodiment of a lift task apparatus in accordance with this invention.
Figure 44:
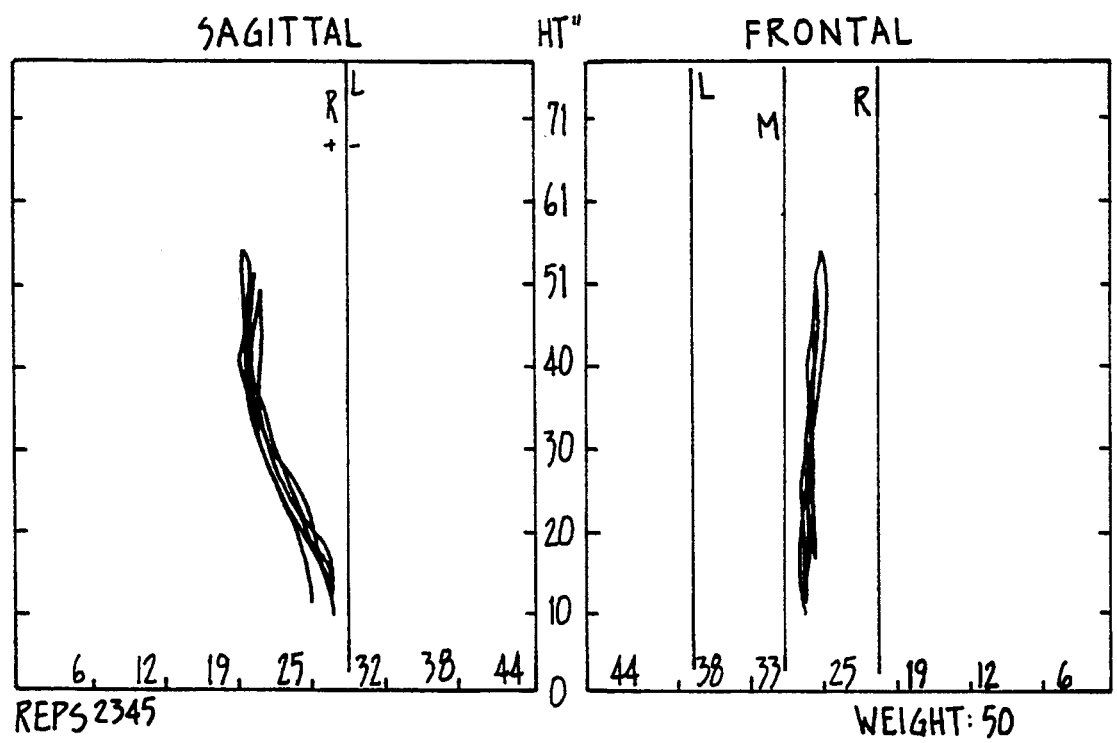

Isokinetic Lift Tests (Tables 2 & 3, FIGS. 42, 44, 45, and Appendix A)

Table 2 illustrates a Run and Modify Screen for an Isokinetic Lift Test and illustrates selectable parameters for this type of lift task testing. If the Device selected is a Box, the Grips data field is presented and the therapist can enter the Grip type being used according to whether it is the grip holes in the box or one of the color coded grip positions. These are listed on a pop up menu for selection. Other parameters that can be entered are Up Vel: the isokinetic velocity limit on the concentric phase upstroke; Dn Vel: the isokinetic velocity limit on the eccentric downstroke phase (which may be different from that on the upstroke); Up Max Frce: the maximum force allowed on the upstroke phase (the parameter S.Force.Lim in FIG. 31 which determines the Breakaway condition for the upstroke phase); and Dn Max Frce: the maximum threshold force (weight) allowed on the downstroke phase (the parameter S.Force.Max in FIG. 30).

Stops setting is preferably done by using the cursor keys on the host computer keyboard to move the arm to a desired stop position and then hitting either the "Home" key on the keyboard to define that as an Upper Stop position (U.Stop in FIG. 30) or the "End" key to define that as a Bottom Stop position (L.Stop in FIG. 30) The actual height in inches for the defined stops the displayed in the "Stops" area of the CRT screen of Table 2.

Under Run Limits, a "Seconds" parameter may be set as the maximum duration of the exercise bout and the number of "Reps" can be selected. The Exercise Mode flag may be set to ON (requiring the therapist to hit the enter key to start acquiring data or OFF.

Under Run Time Options, the "Shelves" option must be False for Isokinetic exercise and can't be set True; the Feet Option may be set True if the therapist wishes to record coordinate positions of the feet on the mat 18 shown in FIG. 1; the "Stops" option will typically be set True since stops will usually be used in this exercise mode and the "Biofeed" option may be set to one of Force Pushbars display, Force vs. Height display, Force and Velocity vs. Height display (e.g. FIG. 45), Saggital and Frontal Position (e.g. FIG. 44) or Overhead Position display.

Table 3 and Appendix A illustrate some of the Isokinetic test results that may be displayed on a screen and/or printed on a printer and/or included in a combined evaluation test report.

Figure 43:
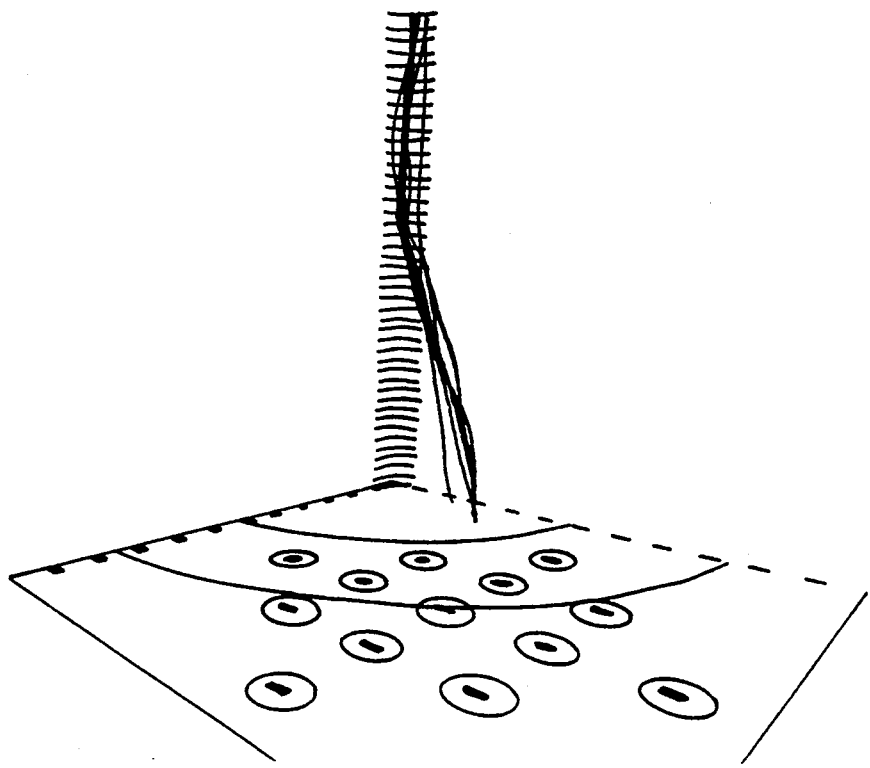

Gravity/Inertia Lift Tests (Tables 4 & 5, FIGS. 43-45, and Appendix A)

Table 4 illustrates the parameters that may be set by the therapist for a gravity/inertia lift which is intended to simulate a real world lift of a mass having a Weight set by the Therapist. The Device and Grip position can be entered as in the Isokinetic test discussed above. Stops may be set but are usually irrelevant to this type of lift task. Run limits may also be set as in the Isokinetic lift task mode previously described. Starting foot locations are often more important in this Lift Task mode and shelf assignments are permitted. Up to two shelves on each of the right and left shelf racks may be utilized but a more typical task involves lifting a box from the ground to place it on a shelf or lifting a box off of a shelf and setting it on the floor.

Table 5 illustrates test data presentations from the Gravity/Inertia test mode and FIGS. 43-45 illustrate the types of graphical data displays that are available in this test mode as hard copy printouts or screen displays.

It should be apparent from the above description of a lift task system of this invention that a highly advantageous exercise, diagnostic and research capability is achieved by this system. The three dimensional movement capability associated with the point of attachment at the end of the arm assembly 13 together with the design of the attachments enables simulation of of the "feel" of real world lifting tasks. The instrumenting of these motion parameters, together with the sophisticated real time software control routines provided for use with each of the different exercise modes produces a system which is safe in operation, accurate in its measurement of force and facile in its control of machine performance based thereon.

One example of comprehensive lift task testing protocols that can be defined on the system of this invention is a special gravity/inertia routine that involves incrementing the "Weight" parameter on each lift repetition until the patient can no longer perform the prescribed lift task, be it lifting from floor to a shelf or lifting a box off of a shelf onto the floor or from a high shelf to a lower shelf.

It will also be recognized that the lift task testing capability of this system is safer than testing using actual weights. The "Let-Go" detection feature of the software control system of this invention makes it safe for the patient to drop the box even when a high weight value has been assigned to it.

Figure 46:
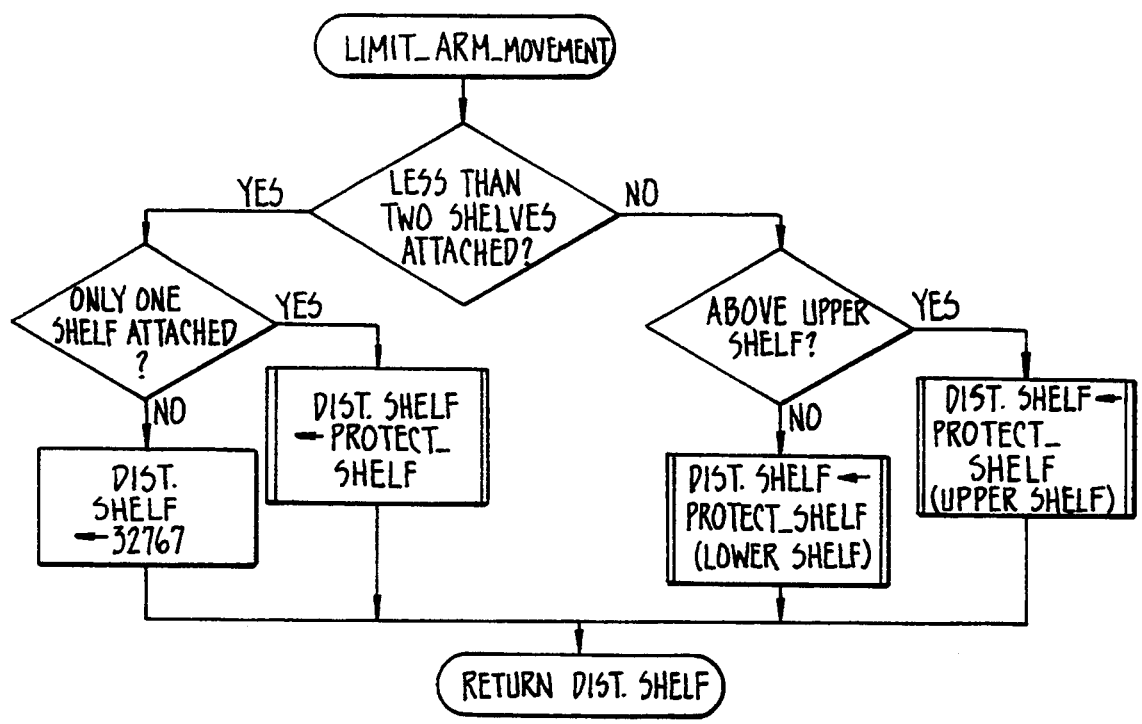
FIGS. 46 and 47 are software flow charts depicting a collision avoidance safety feature of a lift task apparatus in accordance with this invention.
Figure 47:
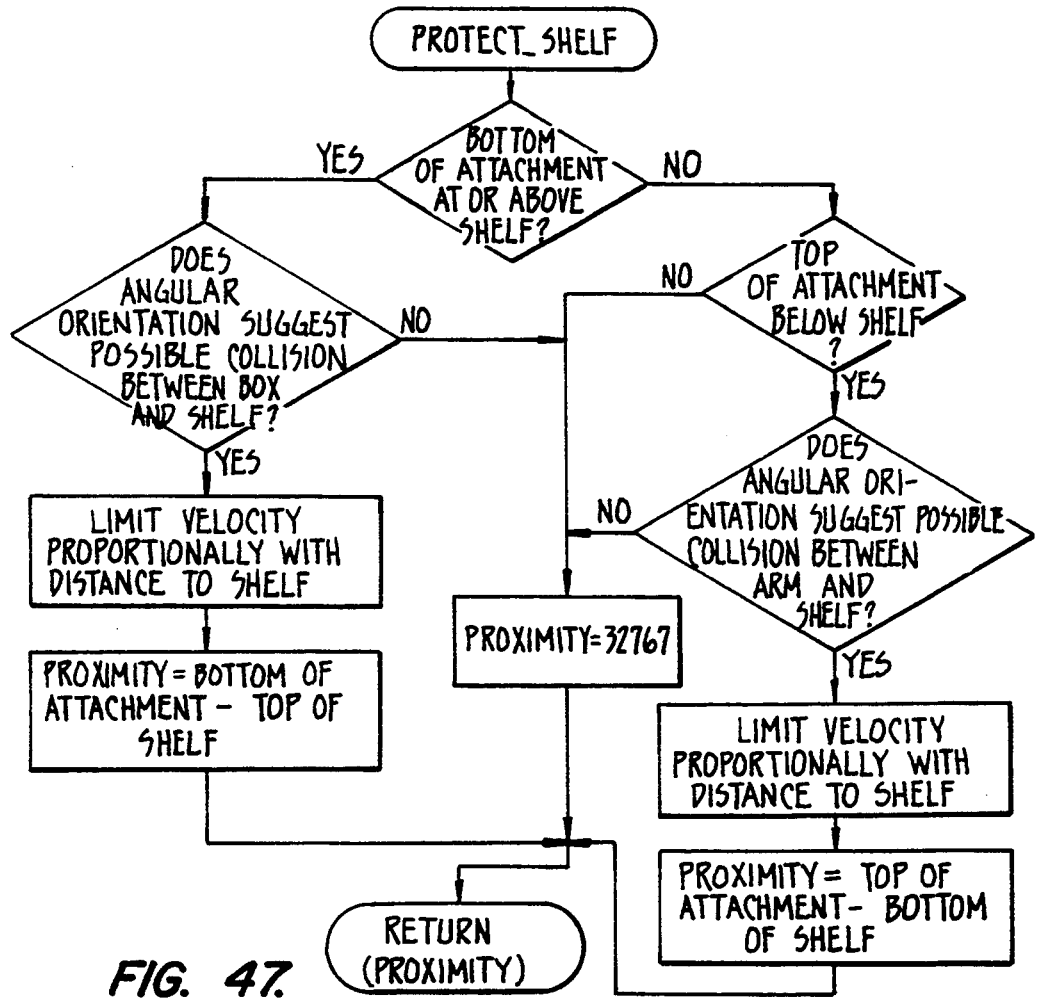

Limit.Arm.Movement Function (FIGS. 46, 47)

This function first looks to see if less than two shelves are attached to the shelf bracket racks and if this returns YES, a checking routine is executed to see if one shelf is attached and if this returns NO, there are no shelves and the value of Dist.Shelf is set to the maximum integer value. If the checking routine for one shelf returns YES, then the Protect.Shelf function is called and the returned value set into Dist.Shelf.

If the first checking step returns NO, then there are two shelves and a checking routine is executed to determine if the arm and box are above the upper shelf. If this returns YES, then Protect.Shelf is run relative to parameters passed relating to the upper shelf and its location as sensed by the system. Otherwise Protect.Shelf is run with parameters relating to the lower shelf on the rack.

Protect.Shelf Function (FIG. 47)

This function first checks whether the bottom of the attachment or box is at or above the shelf level. If this returns YES, then a checking routine is executed to determine if the value of the Angle parameter of the arm is such that the box could collide wiht the shelf if moved up or down. This step is passed parameters on the attachment and the shelf location and a look up table is used to determine if the box or other attachment is within a safe working envelope. If this checking routine returns NO because the box is at an angular position away from the shelf, then Proximity is set to the maximum integer value and that value is returned from the function. If this routine returns YES, then the value of Vel.Cmd is limited proportionally to the verical distance to the shelf so it will decelerate and stop before arriving at the shelf. Then Proximity is set to the distance from the bottom of the attachment (Z.Box) less the z coordinate of the top of the shelf.

If the first checking step returns a NO, then a a checking step is executed to determine if the top of the attachment, i.e. the knob if below the shelf coordinate. IF it is not, then it must be away from the shelf, so the maximum value is set in Proximity and it is returned. If the step returns YES, then the checking routine is done on the angular position of the box to determine if a collision with the shelf is possible. If not, then Proximity is set to max value, and if YES is returned, Vel.Cmd is limited as before dan Proximity is set to the distance between the top of the attachment and the bottom of the shelf.

While the apparatus and method of this invention have been described in detail in connection with a preferred embodiment and various modification and variations on the preferred embodiment, it should be understood that numerous other modifications could be made without departing from the scope of the invention as claimed in the appended claims. For example, it should be apparent that the load measuring system could be a torque measurement on the output shaft of the servo drive system, but the performance of the system in the servo control loop, especially in the gravity/inertia mode is likely to be degraded due to the phase difference between force application to the interface device and the torque measurement on the shaft. Furthermore force determination is more complicated since the torque measured on the shaft must be converted to force using the distance of force application so a more complicated calculation of actual user applied force is involved.

It should also be apparent that other vertical transmission drive arrangements, such as a ball screw and threaded rod drive could be used but again with some degraded system performance. If movement of the interface device and arm is limited to a vertical movement, a different form of load cell without self cancellation of extraneous forces could be used together with an attachment mounting arrangement that applied force to the load cell only in the vertical direction without any torsional moments or side thrust forces.

It should be apparent that skilled persons in the art of real time computer control systems could make many modifications in the software control routines to achieve the same or substantially the same overall control system functionality.

In addition, it should be understood that the principles of the method of this invention could be applied in a wide variety of different forms of apparatus having the basic functionality required to perform the method steps.

TABLE 1

```
LIDO LIFT
Version 2.2
```

RUN PROTOCOL

| Protocol Name | Parameters | Stops |
|---|---|---|
| 1. Work Capacity<br>2. Defined<br>3. User Defined<br>4. User Defined<br>5. User Defined<br>6. User Defined<br>7. User Defined | Exercise 1 of 1<br>Type:    Isometric<br>Device:  T-Handle<br>Grip:    12"<br>Max Force: 400 | Stop 1 of 3<br>Label:<br>ARM<br>Height:   44.0<br>Pause:    20<br>Duration: 5<br>Reps:     3 |

| Foot Location | Run Time Options |
|---|---|
| Left Foot X:  28<br>Left Foot Y:  36<br>Right Foot X: 28<br>Right Foot Y: 29 | Shelves:  FALSE<br>Feet:     FALSE<br>Stops:    TRUE<br>Biofeed:Force Bars |

Spacebar to Edit  ^v-Chg Field  ↵-Run Tests  )-Parameters  F1-Help  Esc-Quit

TABLE 2

```
┌─────────────────────────────────┐
│          LIDO LIFT              │
│         Version 2.2             │
└─────────────────────────────────┘
```

MODIFY & RUN PROTOCOL

Protocol Name                Parameters                    Stops

```
┌───────────────────┐  ┌───────────────────────┐  ┌──────────────────────┐
│                   │  │ Exercise 1 of 3       │  │ Stop Limits          │
│ 1. Work Capacity  │  │ Type:    Isokinetic   │  │ Top:       67.6      │
│ 2.    Defined     │  │ Device:  Small Box A  │  │ Bottom:     0.0      │
│ 3. User Defined   │  │ Grip:    grips        │  │                      │
│ 4. User Defined   │  │ Up Vel:       10      │  │ Run Limits           │
│ 5. User Defined   │  │ Dn Vel:       10      │  │ Seconds:    60       │
│ 6. User Defined   │  │ Up Max Frce:  35      │  │ Reps:        3       │
│ 7. User Defined   │  │ Dn Max Frce:  35      │  │ Exercise Mode: ON    │
└───────────────────┘  └───────────────────────┘  └──────────────────────┘
```

Foot Location                                        Run Time Options

```
┌───────────────────┐                             ┌──────────────────────┐
│ Left Foot X:  28  │                             │ ‡Shelves:    FALSE   │
│ Left Foot Y:  36  │                             │  Feet:       FALSE   │
│ Right Foot X: 28  │                             │  Stops:      FALSE   │
│ Right Foot Y: 20  │                             │  Biofeed:Force Bars  │
└───────────────────┘                             └──────────────────────┘
```

Spacebar to Edit  ^v-Chg Field  <-Foot Loc              F1-Help  Esc-Back

TABLE 3
ISOKINETIC TEST DATA

—Rep# 2—

| | | | |
|---|---|---|---|
| Peak Force Lifting   | 199.2 lbs | Ht at Peak Force Lifting  | 19.1 Inches |
| Peak Force Lowering  |   0.0 lbs | Ht at Peak Force Lowering | 33.3 Inches |
| Average Force Lifting  | 175.5 lbs | Total Work Lifting  | 433.9 ft-lbs |
| Average Force Lowering |   0.0 lbs | Total Work Lowering |   0.0 ft-lbs |

|  | Raising | Lowering |
|---|---|---|
| Peak Force (lbs) | 227.8 | 0.0 |
| Average Force (lbs) | 178.7 | 0.0 |
| Height At Peak Force (inches) | 19.5 | 33.3 |
| Total Work (ft-lbs) | 1333.4 | 0.0 |
| Average Work (ft-lbs) | 444.5 | 0.0 |
| Peak Power (ft-lbs / sec) | 272.9 | 0.0 |
| SD Force (lbs) | 14.5 | 0.0 |
| CV Force | 8 | 0 |

TABLE 4

```
┌─────────────────────────────────┐
│          LIDO LIFT              │
│         Version 2.2             │
└─────────────────────────────────┘
```

MODIFY & RUN PROTOCOL

Protocol Name                Parameters                    Stops

```
┌───────────────────┐  ┌────────────────────────┐  ┌──────────────────────┐
│                   │  │ Exercise 1 of 3        │  │ Stop Limits          │
│ 1. Work Capacity  │  │ Type:  Gravity/Inertia │  │ Top:       67.6      │
│ ‡2.   Defined     │  │ Device:  Small Box A   │  │ Bottom:     0.0      │
│ 3. User Defined   │  │ Grip:    grips         │  │                      │
│ 4. User Defined   │  │ Weight:   15           │  │ Run Limits           │
│ 5. User Defined   │  │                        │  │ Seconds:    60       │
│ 6. User Defined   │  │                        │  │ Reps:        3       │
│ 7. User Defined   │  │                        │  │ Exercise Mode: ON    │
└───────────────────┘  └────────────────────────┘  └──────────────────────┘
```

Foot Location            Shelf Assignments              Run Time Options

```
┌───────────────────┐  ┌────────────────────┐     ┌──────────────────────┐
│ Left Foot X:  28  │  │ Left Shelf A:   0  │     │ Shelves:    FALSE    │
│ Left Foot Y:  36  │  │ Left Shelf B:   0  │     │ Feet:       FALSE    │
│ Right Foot X: 28  │  │ Right Shelf A:  0  │     │ Stops:      FALSE    │
│ Right Foot Y: 20  │  │ Right Shelf B:  0  │     │ Biofeed:Fr/Sag       │
└───────────────────┘  │ Shelf Check:  OFF  │     └──────────────────────┘
                       └────────────────────┘
```

Spacebar to Edit  ^v-Chg Field  <─┘-Run Tests  >-Parameters  F1-Help  Esc-Quit

TABLE 5
GRAVITY/INERTIA TEST DATA

| | | |
|---|---|---|
| Peak Force | 98.2 | lbs |
| Peak Upward Accel Lifting | 1 | G's |
| Avg Upward Accel Lifting | 0.2 | G's |
| Peak Upward Accel Lowering | 0.5 | G's |
| Avg Upward Accel Lowering | 0.3 | G's |
| Velocity Peak Lifting | 58.5 | in/sec |
| Velocity Average Lifting | 26.5 | in/sec |
| Velocity Peak Lowering | 52.5 | in/sec |
| Velocity Average Lowering | 26.4 | in/sec |
| Lifting Peak/Avg Accel Ratio | 409 | % |
| Lowering Peak/Avg Accel Ratio | 183 | % |

| | | Lifting | Lowering |
|---|---|---|---|
| Top Ht | (inches) | 54.0 | |
| Bottom Ht | (inches) | 11.0 | |
| Sagittal Plane | | Lifting | Lowering |
| Mean Track | (inches) | + 4.8 | + 6.0 |
| Peak Deviation | (inches) | + 5.2 | + 8.0 |
| Frontal Plane | | Lifting | Lowering |
| Mean Track | (inches) | Rt 2.3 | Rt 2.6 |
| Peak Deviation | (inches) | Rt 3.8 | Rt 3.0 |
| Peak Acceleration | (G's) | 1 | 0.5 |
| Peak Force | (lbs) | 98.2 | |

APPENDIX A. SAMPLE TEST REPORT 01-19-90  
11:56am

Backs 'R' Us  
L5/S1 Back Street  
Lumbar City, California 99999

LIFTING EVALUATION
Capacities & Recommendations

Client: Thomas , Kapenda  
ID:

FUNCTIONAL LIFTING EVALUATION

On 12-21-89 Mr. Thomas completed a functional lifting evaluation on the Lido Lift. The following is a report of that examination including the test results and an evaluation of Kapenda's lifting ability.

The examination consisted of three tests, isometric, isokinetic and Gravity/Inertia. The isometric and isokinetic tests each produced predictions of maximum dynamic lifting capacity. The Gravity/Inertia test is a 'real world' simulation designed to refine the isometric and isokinetic predictions and verify maximum capacity.

The following table, OVERALL TEST CONCLUSIONS, is the final product of all of these tests. The details of each of the individual tests are outlined in the following pages.

OVERALL TEST CONCLUSIONS

| Frequency | Maximum Capacity (lbs) | Recommended Capacity(1) (lbs) |
|---|---|---|
| Occasional | 134 | 87 |
| Frequent (2) | 81 | 61 |
| Constant (2) | 62 | 53 |

The maximum capacity level is by definition the physical limit of the individual. By working at the recommended capacity level the risk of injury will be reduced to approximately 1/3 of the risk observed when individuals work at their maximum capacity. (1)

LIFTING EVALUATION
Capacities & Recommendations

Isometric Results:
The following table indicates Keranda's strength (force produced), consistency (coefficient of variation - CV) and percentile ranking at each of the tested positions for the Standardized Isometric Test. (3)

RESULTS OF ISOMETRIC TEST

| Lift Type | Percentile Ranking (4) | Average Force (lbs) | CV for 3 Efforts |
|---|---|---|---|
| Arm | 70 | 96.9 | 2.6% |
| Leg | 68 | 254.7 | 11.4% |

Isometric Conclusions:
Based on a comparison of Mr. Thomas's strength against normative data at these three positions, the following prediction of his functional capacity has been made:

LIFTING CAPACITY BASED UPON ISOMETRIC TEST

| Frequency | Predicted Capacity(5) (lbs) | Recommended Capacity(1) (lbs) |
|---|---|---|
| Occasional | 114 | 74 |
| Frequent (2) | 69 | 52 |
| Constant (2) | 53 | 45 |

The average CV for all three isometric tests combined is 4.7%. Based on this value we have reason to believe that Mr. Thomas performed maximally, however the CV value for the LEG effort is higher than it should be, throwing some doubt onto the validity of the LEG measurement.

The average percentile ranking for Mr. Thomas is 46%. This indicates strength that is below average for the general population of males employed in industry. (4) Therefore Kapenda will not be able to perform certain lifting tasks safely.

Isokinetic Results:

The following table indicates Mr. Thomas's isokinetic strength (force produced) as measured by the best three out of five repetitions at 15 inches per second.

RESULTS OF ISOKINETIC TEST

| Rep | Peak Force (lbs) | Average Force (lbs) |
|---|---|---|
| 5 | 214.0 | 182.0 |
| 2 | 199.2 | 172.9 |
| 3 | 187.6 | 169.1 |
| Average | 200.3 | 174.6 |

The average CV for all three isokinetic reps combined is 8%. Based on this value we have a high degree of confidence that Kapenda gave us his best effort and that the dynamic capacity predictions are valid.

Isokinetic Conclusions:

Based on the results of Mr. Thomas's isokinetic strength the following prediction of his dynamic lifting capacity has been made:

LIFTING CAPACITY BASED UPON ISOKINETIC TEST

| Frequency | Predicted Capacity (lbs) | Recommended Capacity(1) (lbs) |
|---|---|---|
| Occasional | 154 | 100 |
| Frequent (2) | 93 | 70 |
| Constant (2) | 72 | 61 |

Tested Gravity Inertia Strength

The maximum predicted capacity from isometric was averaged with the maximum predicted isokinetic capacity to give a starting weight of 134 pounds for Gravity/Inertia testing. Mr. Thomas was able to lift 134 pounds successfully, while meeting all of the criteria for a maximal lift.

Definitions:

Work capacities are based on the articles referenced below. "The Dictionary of Occupational Titles", United States Department of Labor (6) defines Occasional, Frequent and Constant as follows:

FREQUENCY OF TASK

| Frequency | % of Time | Approximate Repetitions per Week |
|---|---|---|
| Occasional | 0 - 33 | 1 - 100 |
| Frequent | 34 - 66 | 100 - 500 |
| Constant | 67 - 100 | 500+ |

References:

(1) Chaffin DB, Herrin GD, Keyserling WM: Pre-employment strength testing: an updated position. JOM 20: pp 403-408, June 1978.
(2) Snook, SH: The design of manual handling tasks, Ergonomics 21:963-985, 1978.
(3) Chaffin DB: Ergonomics guide for the assessment of human strength. J of AIHA, July 1975.
(4) Batti'e, MC et.al.: Isometric lifting strength as a predictor of industrial back pain reports. Spine: Volume 14, Number 8, 1989.
(5) Chaffin DB, Herrin GD, Keyserling WM, Foulke, JA: Pre-employment strength testing in selecting workers for materials handling jobs. NTIS PB89-196076, Ch. 4, October 1976.
(6) U.S. Department of Labor: Dictionary of Occupational Titles, 4th Edition Supplement, Appendix D, pp 101-102, 1986.

Sincerely yours,                                   Protocol Name: Comprehensive 2

U.R. Smart, PhD.

What is claimed is:

1. An apparatus for performing a lift task comprising:
interface means adapted to be grasped and lifted by a human subject and having an actual mass value;
means for setting a simulated mass value for said interface means independent of said actual mass value;
force measuring means for measuring the value of vertical force exerted by said human subject upon said interface means, said force measuring means comprising:
load measuring means for measuring total vertical force applied to said interface means;
acceleration measuring means for measuring the actual vertical acceleration of said interface means;
weight calculating means for calculating an actual mass value of said interface means;
inertia calculating means for calculating an inertia calibration factor for said interface means; and
force calculating means for calculating the actual force applied by said human subject as a function of the current output of said load measuring means, said actual mass value, the current output of said acceleration measuring means and said inertia calibration factor; and
exercise control means, coupled to said interface means and responsive to said force measuring means, for providing a controlled vertical movement of said interface means as a function of said simulated mass value such that said interface means responds to a lifting force by said human subject in a manner that simulates the inertia of an object having a mass value equal to said simulated mass value in a gravitational field.

2. The apparatus according to claim 1 wherein said exercise control means further comprises:
   servo motor drive means for providing the controlled vertical movement of the interface means;
   velocity servo control means, coupled to said servo motor drive means, for controlling the vertical velocity of said interface means in response to a velocity command signal; and
   means for deriving and supplying to said velocity servo control means said velocity command signal as a predetermined function of a prior velocity command signal, said value of vertical force and said simulated mass value.

3. The apparatus according to claim 1 wherein said actual mass value of said interface means is unknown;
   wherein said apparatus further comprises a horizontal arm for carrying said interface means on a free end thereof, the horizontal arm being capable of upward and downward movement;
   wherein said exercise control means further comprises transmission means coupled to said servo motor drive means such that said velocity servo control means, said servo motor drive means and said transmission means cooperatively control the upward and downward movement of said horizontal arm means;
   wherein said load measuring means is coupled between said horizontal arm and said interface means for measuring the total vertical force applied to said horizontal arm by said interface means;
   wherein said acceleration measuring means is mounted on said horizontal arm for measuring the actual vertical acceleration of said horizontal arm and said interface means;
   wherein said weight calibration means includes means for positioning said interface means with only its mass exerting force on said load measuring means and for recording the output of said load measuring means as an actual mass value of said interface means; and
   wherein said inertia calibration means includes means for driving said servo motor means to move said horizontal arm through a predetermined pattern of different acceleration values, for recording a sequence of outputs of said load measuring means and associated outputs of said acceleration measuring means, and for calculating from said recorded sequence of outputs the inertia calibration factor which correlates said actual acceleration value with load values.

4. The apparatus according to claim 1 wherein the exercise control means further comprises:
   servo motor means, coupled to said interface means, for driving said interface means for said controlled vertical movement;
   velocity command means, coupled to said servo motor means, for controlling said servo motor means in response to a velocity command parameter, the velocity command means including:
   means for calculating a velocity change parameter as a function of said actual force and said simulated mass value;
   means for calculating a new velocity command parameter as a function of a current velocity command parameter and said velocity change parameter; and
   means for controlling said servo motor means in response to said new velocity command parameter.

5. The apparatus according to claim 4 wherein the exercise control means further comprises:
   let-go detection means for detecting when said actual force is within a selected range of values for a selected time duration and for generating a let-go signal in response thereto; and
   wherein said velocity command means includes means for applying a safety control factor to said new velocity command parameter in response to said let-go signal so that said interface means descends at a lower velocity than originally indicated by said new velocity command parameter.

6. The apparatus according to claim 4 further comprising:
   means for inputting and storing a velocity limit value;
   wherein said velocity command means includes means for calculating said velocity command parameter so that a velocity of said interface means is limited to said velocity limit value.

7. The apparatus according to claim 4 wherein said exercise control means further comprises:
   means for defining an upper motion limit and a lower motion limit;
   means for defining an upstroke mode and a downstroke mode;
   wherein said upstroke mode designates a lift task wherein said interface means is to be moved from said lower motion limit to said upper motion limit;
   wherein said downstroke mode designates a lift task wherein said interface means is to be moved from said upper motion limit to said lower motion limit;
   means for inputting and storing an upstroke velocity limit value and a downstroke velocity limit value; and
   wherein said velocity command means includes means for calculating said velocity command parameter so that a velocity of said interface means is limited to said upstroke velocity limit value during said upstroke mode and to said downstroke velocity limit value during said downstroke mode.

8. The apparatus according to claim 1 wherein said exercise control means further comprises:
   means for defining an upper motion limit and a lower motion limit;
   means for defining an upstroke mode, said upstroke mode designating a lift task wherein said interface means is to be moved from said lower motion limit to said upper motion limit; and
   means for precluding downward movement of said interface means when said exercise control means is in upstroke mode.

9. The apparatus according to claim 1 wherein said exercise control means further comprises:
   means for defining an upper motion limit and a lower motion limit;
   means for defining a downstroke mode, said downstroke mode designating a lift task wherein said interface means is to be moved from said upper motion limit to said lower motion limit; and
   means for precluding upward movement of said interface means when said exercise control means is in downstroke mode.

10. The apparatus according to claim 1 wherein said exercise control means further comprises:
  means for defining an upstroke mode, said upstroke mode designating a lift task wherein said interface means is to be moved from said lower motion limit to said upper motion limit; and
  means for precluding downward movement of said interface means when said exercise control means is in said upstroke mode.

11. The apparatus according to claim 1 wherein said exercise control means further comprises:
  means for defining an upper motion limit and a lower motion limit;
  means for defining an upstroke mode and a downstroke mode;
  wherein said upstroke mode designates a lift task wherein said interface means is to be moved from said lower motion limit to said upper motion limit;
  wherein said downstroke mode designates a lift task wherein said interface means is to be moved from said upper motion limit to said lower motion limit;
  means for simulating an upstroke weight value of said interface means during said upstroke mode;
  means for simulating a downstroke weight value of said interface means during said downstroke mode; and
  wherein said downstroke weight value is greater than said upstroke weight value.

12. The apparatus according to claim 11 wherein said force measuring means further comprises peak force measuring means for measuring a peak force value applied to said interface means by said human subject during said upstroke mode, and wherein said exercise control means simulates said downstroke weight value as a multiple of said peak force value.

13. The apparatus according to claim 11 further comprising:
  means for inputting and storing an upstroke velocity limit value and a downstroke velocity limit value; and
  wherein said exercise control means includes means for controlling the movement of said interface means so that a vertical velocity of said interface means is limited to said upstroke velocity limit value during said upstroke mode and to said downstroke velocity limit value during said downstroke mode.

14. An apparatus for performing a lift task comprising:
  an interface device adapted to be grasped and lifted by a human subject;
  mounting means for mounting said interface device for combined movement within a range of z, r, and theta coordinates of a cylindrical coordinate system with said z coordinate having a vertical orientation;
  force measuring means for measuring the amount of vertical force applied to said interface device by said human subject and for producing an output force signal;
  acceleration measuring means for directly measuring the amount of linear vertical acceleration of said interface device and for producing an output acceleration signal for simulating an inertia of the interface device in a gravitational field; and
  movement control means, operatively associated with said mounting means and responsive to at least one of said output force signal and said output acceleration signal for controlling movement of said interface device along said z coordinate and for controlling z coordinate velocity and acceleration of said interface device in accordance with a preselected lift task function.

15. An apparatus for performing a lift task comprising:
  an interface device adapted to be grasped and lifted by a human subject;
  mounting means for mounting said interface device for combined movement within a range of z, r, and theta coordinates of a cylindrical coordinate system with said z coordinate having a vertical orientation;
  force measuring means for measuring the amount of vertical force applied to said interface device by said human subject and for producing an output force signal;
  acceleration measuring means for measuring the amount of vertical acceleration of said interface device and for producing an output acceleration signal; and
  movement control means, operatively associated with said mounting means and responsive to at least one of said output force signal and said output acceleration signal for controlling movement of said interface device along said z coordinate and for controlling z coordinate velocity and acceleration of said interface device in accordance with a preselected lift task function;
  wherein said mounting means comprises:
    a vertical support column;
    a carriage;
    carriage mounting means for mounting said carriage for vertical movement on said vertical support column;
    a support arm;
    arm mounting means for mounting said support arm for damped swinging movement in a horizontal plane on said carriage; and
    wherein said support arm comprises:
      a first arm member mounted at one end thereof to said carriage by said arm mounting means; and
      a second arm member mounted in a freely sliding relation on said first arm member with said interface device mounted on a free end of said second arm member.

16. The apparatus according to claim 14 wherein the movement control means further comprises:
  servo motor means, coupled to said interface device, for driving said interface device for vertical movement;
  velocity command means, coupled to said servo motor means, for controlling said servo motor means in response to a velocity command parameter, the velocity command means including:
    means for calculating a velocity change parameter as a function of said vertical force applied to said interface device by said human subject;
    means for calculating a new velocity command parameter as a function of a current velocity command parameter and said velocity change parameter; and
    means for controlling said servo motor means in response to said new velocity command parameter.

17. The apparatus according to claim 16 wherein the movement control means further comprises:

let-go detection means for detecting when said vertical force applied to said interface device by said human subject is within a selected range of values for a selected time duration and for generating a let-go signal in response thereto; and wherein said velocity command means includes means for applying a safety control factor to said new velocity command parameter in response to said let-go signal so that said interface device vertically descends at a lower velocity than originally indicated by said new velocity command parameter.

18. The apparatus according to claim 16 further comprising: means for inputting and storing a velocity limit value;

wherein said velocity command means includes means for calculating said velocity command parameter so that a velocity of said interface means is limited to said velocity limit value.

19. The apparatus according to claim 16 wherein said exercise control means further comprises:

means for defining an upper motion limit and a lower motion limit;

means for defining an upstroke mode and a downstroke mode;

wherein said upstroke mode designates a lift task wherein said interface means is to be moved from said lower motion limit to said upper motion limit;

wherein said downstroke mode designates a lift task wherein said interface means is to be moved from said upper motion limit to said lower motion limit;

means for inputting and storing an upstroke velocity limit value and a downstroke velocity limit value; and wherein said velocity command means includes means for calculating said velocity command parameter so that a velocity of said interface means is limited to said upstroke velocity limit value during said upstroke mode and to said downstroke velocity limit value during said downstroke mode.

20. An apparatus for performing a lift task comprising:

a horizontal arm;
a vertical support;
a carriage means,
mounted on said vertical support, for carrying said horizontal arm for vertical upward and downward movement;
transmission means, coupled to said carriage means, for driving said carriage means in said upward and downward movement;
servo motor means, coupled to said transmission means, for powering said transmission means to drive said carriage means;
servo control means, coupled to said servo motor means, for controlling the operation of said servo motor means in driving said transmission means;
load measuring means, mounted on a free end of said horizontal arm for measuring the amount of vertical force applied to said horizontal arm and for producing an output force signal;
acceleration measuring means, mounted on said horizontal arm, for directly measuring the linear vertical acceleration of the horizontal arm and for producing an output acceleration signal for simulating an inertia of the interface device in a gravitational field;
interface means, coupled to said load measuring means, for enabling a human subject to apply vertical force to said horizontal arm; and
wherein said servo control means receives said output force signal and said output acceleration signal for controlling said servo motor means for driving said transmission means as a prearranged function of a preselected lift task control mode and associated control mode parameters including a simulated mass value for said interface means, said output force signal and said output acceleration signal.

21. An apparatus for performing a lift task comprising:

a horizontal arm;
a vertical support;
a carriage means, mounted on said vertical support, for carrying said horizontal arm for vertical upward and downward movement;
transmission means, coupled to said carriage means, for driving said carriage means in said upward and downward movement;
servo motor means, coupled to said transmission means, for powering said transmission means to drive said carriage means;
servo control means, coupled to said servo motor means, controlling the operation of said servo motor means in driving said transmission means;
load measuring means, mounted on a free end of said horizontal arm for measuring the amount of vertical force applied to said horizontal arm and for producing an output force signal;
acceleration measuring means, mounted on said horizontal arm, for measuring the vertical acceleration of the horizontal arm and for producing an output acceleration signal;
interface means, coupled to said load measuring means, for enabling a human subject to apply vertical force to said horizontal arm; and
wherein said servo control means receives said output force signal and said output acceleration signal for controlling said servo motor means for driving said transmission means as a prearranged function of a preselected lift task control mode and associated control mode parameters including a simulated mass value for said interface means, said output force signal and said output acceleration signal;
wherein said servo control means comprises:
a central processor;
converter means, coupled to said acceleration measuring means, to said load measuring means and to said central processor, for converting said output acceleration signal and said output force signal from analog to digital signal values for input to said central processor at a preselected data acquisition rate; and
said processor including:
an interface calibration module operative during a calibration interval prior to operation of said apparatus in said preselected lift task control mode;
said interface calibration module including:
means for storing as an interface weight parameter the digital signal value corresponding to said output force signal when said interface means is being acted on only by earth gravitational forces;
means for controlling said servo motor means during an inertial calibration interval prior to performing a lift exercise task to move said interface means through a pattern of different acceleration values;

means for storing the associated digital signal values corresponding to said output force signal and said output acceleration signal during said inertial calibration interval; and means for analyzing said stored associated digital signal values to determine an inertial calibration factor which translates an output acceleration signal into a corresponding inertial force value due to acceleration applied to said interface means; and a velocity command calculating module for calculating a velocity command value to supply to said servo motor control means during operation of said apparatus in said preselected lift task control mode, said velocity command calculation module including:

means for storing set mass and set threshold force parameter values associated with inertia and weight of an object to be simulated as the object to be lifted by a human subject;

means for reading and storing the digital signal value corresponding to said output force signal as a lift force parameter value and for reading and storing the digital signal value corresponding to said output acceleration signal as a current acceleration parameter value;

means for calculating a force parameter as the actual force being applied by a human subject to said interface means as a predetermined function of said lift force parameter, said interface weight parameter, said current acceleration parameter, and said inertial calibration factor, means for calculating a simulated net force applied to said interface means as a function of said force parameter and said set threshold force parameter, means for calculating a velocity change parameter as a function of said net force parameter and said set mass parameter, and means for calculating and storing a new velocity command parameter as a function of the currently stored velocity command parameter and said velocity change parameter.

22. The apparatus according to claim 21, wherein said preselected lift task control mode is a gravity inertia lift task mode for simulating the lifting of an object having a set mass value independent of the actual mass of said interface means, and said set mass parameter and said set threshold force parameter are the same value such that said apparatus simulates the inertial response of an object having said set mass value in an earth gravitational field.

23. The apparatus according to claim 14 wherein said central processor further comprises a let-go detection module including:

let-go detection means for producing a let-go signal when the value of said force parameter is within a preselected band of let go values for a preselected let-go time duration, and means for applying a preselected safety control factor to said new velocity command parameter in response to said let-go signal.

24. An apparatus for performing a lift task comprising:

a horizontal arm;

a vertical support;

carriage means, mounted on said vertical support, for carrying said horizontal arm for vertical upward and downward movement;

transmission means, coupled to said carriage means, for driving said carriage means in said upward and downward movement;

servo motor means, coupled to said transmission means, for powering said transmission means to drive said carriage means;

servo control means, coupled to said servo motor means, for controlling the operation of said servo motor means in driving said transmission means;

interface means, having an actual mass value and being coupled to said horizontal arm, for enabling a human subject to apply vertical force to said horizontal arm;

means for setting a simulated mass value for said interface means independent of said actual mass value;

force measuring means for measuring the value of vertical force exerted by said human subject upon said interface means, said force measuring means comprising:

load measuring means for measuring total vertical force applied to said interface means and for producing an output load signal;

acceleration measuring means for measuring the actual vertical acceleration of said interface means;

weight calculating means for calculating an actual mass value of said interface means;

inertia calculating means for calculating an inertia calibration factor for said interface means; and force calculating means for calculating the actual force applied by said human subject as a function of the current output of said load measuring means, said actual mass value, the current output of said acceleration measuring means and said inertia calibration factor; and wherein said servo control means is coupled to said force measuring means for controlling said servo motor means for driving said transmission means in response to said force measuring means so that said interface means responds to a lifting force by said human subject in a manner that simulates the inertia of an object having a mass value equal to said simulated mass value in a gravitational field.

25. The apparatus according to claim 24, wherein said carriage means includes hinge means for carrying said horizontal arm and providing for rotation of a free end of said horizontal arm through an angular range of motion about said vertical support, said interface being carried on said free end of said horizontal arm for rotation therewith.

26. The apparatus according to claim 24, wherein said horizontal arm comprises:

a fixed arm member mounted on said carriage means;

a movable arm member mounted for translation with respect to said fixed arm member in a horizontal plane; and wherein said interface means is coupled to a free end of said movable arm member for translation therewith.

27. The apparatus according to claim 24 wherein said carriage means includes hinge means for carrying said horizontal arm and for providing for rotation of said horizontal arm through an angular range of motion; and wherein said horizontal arm comprises:
- a fixed arm member mounted on said hinge means; and
- a movable arm member mounted for translation with respect to said fixed arm member in a horizontal plane;
- wherein said interface means is coupled to a free end of said movable arm member for translation therewith so that said interface means can be moved throughout a three dimensional working envelope including a horizontal working envelope component defined by the angular range of motion of said horizontal arm on said hinge means and the linear range of motion of said movable arm member relative to said fixed arm member.

28. The apparatus according to claim 27 further comprising:
- first position tracking means for producing an output height signal to said servo control means corresponding to the vertical height of said carriage means on said vertical support;
- second position tracking means for producing an output angle signal to said servo control means corresponding to the angle of said horizontal arm in said horizontal plane about said vertical support; and
- third position tracking means for producing an output radius signal to said servo control means corresponding to the position of said movable arm member relative to said fixed arm member; and
- wherein said servo control means controls the operation of said servo motor means in response to said height, angle and radius signals in a cylindrical coordinate system.

29. The apparatus according to claim 28, wherein said interface means is a box of predetermined spatial box geometry, wherein said movable arm member has a predetermined spatial arm geometry, wherein said apparatus further comprises shelf means providing a horizontal shelf adapted to support said box and having a known spatial shelf geometry and known shelf location in terms of said cylindrical coordinate system, and wherein said servo motor control means comprises:
- a central processor;
- converter means for converting said output load signal, said height signal, said angle signal and said radius signal from analog signal values to corresponding digital signal values for input to said central processor at a preselected data acquisition rate; and
- control program means for operating said central processor to produce a control command signal for driving said servo motor, said control program means including:
  - means defining a safe working three dimensional envelope for said box and movable arm member as a function of said predetermined spatial box geometry, spatial arm geometry, and spatial shelf geometry and spatial shelf location within said cylindrical coordinate system,
  - means for assessing the current spatial position of said movable arm member and said box relative to said safe working envelope, and
  - means for determining when said arm member and box cross the boundary of said safe working envelope and for limiting the movement of said movable arm member in a coordinate direction of said cylindrical coordinate system in response to said determination.

30. The apparatus according to claim 29, wherein said shelf means comprises:
- a shelf bracket having a plurality of shelf mounting locations at various known Height coordinate locations; and
- a shelf location sensor for signalling to said central processor at which of said shelf mounting location a shelf has been placed.

31. The apparatus according to claim 27 wherein said interface means has a spatial interface geometry, and wherein said servo control means further comprises:
- means for defining a safe working three dimensional envelope for said interface means as a function of said spatial interface geometry;
- means for assessing the current spatial position of said interface means;
- means for determining when said interface means crosses the boundary of said three dimensional envelope; and
- means for limiting the movement of said interface means to maintain the interface means within said three dimensional envelope.

32. The apparatus according to claim 31 wherein said limiting means includes means for limiting the vertical movement of said interface means to maintain said interface means within said three dimensional envelope.

33. The apparatus according to claim 24 wherein said servo control means further comprises:
- velocity command means, coupled to said servo motor means, for controlling said servo motor means in response to a velocity command parameter, the velocity command means including:
  - means for calculating a velocity change parameter as a function of said actual force and said simulated mass value;
  - means for calculating a new velocity command parameter as a function of a current velocity command parameter and said velocity change parameter; and
  - means for controlling said servo motor means in response to said new velocity command parameter.

34. The apparatus according to claim 33 wherein said servo control means further comprises:
- let-go detection means for detecting when said actual force is within a selected range of values for a selected time duration and for generating a let-go signal in response thereto; and
- wherein said velocity command means includes means for applying a safety control factor to said new velocity command parameter in response to said let-go signal so that said interface means descends at a lower velocity than originally indicated by said new velocity command parameter.

35. The apparatus according to claim 33 further comprising:
- means for inputting and storing a velocity limit value;
- wherein said velocity command means includes means for calculating said velocity command parameter so that a velocity of said interface means is limited to said velocity limit value.

36. The apparatus according to claim 33 wherein said servo control means further comprises:
- means for defining an upper motion limit and a lower motion limit;

means for defining an upstroke mode and a downstroke mode;

wherein said upstroke mode designates a lift task wherein said interface means is to be moved from said lower motion limit to said upper motion limit;

wherein said downstroke mode designates a lift task wherein said interface means is to be moved from said upper motion limit to said lower motion limit;

means for inputting and storing an upstroke velocity limit value and a downstroke velocity limit value; and wherein said velocity command means includes means for calculating said velocity command parameter so that a velocity of said interface means is limited to said upstroke velocity limit value during said upstroke mode and to said downstroke velocity limit value during said downstroke mode.

37. The apparatus according to claim 24 wherein said servo control means further comprises:

means for defining an upper motion limit and a lower motion limit;

means for defining an upstroke mode, said upstroke mode designating a lift task wherein said interface means is to be moved from said lower motion limit to said upper motion limit; and means for precluding downward movement of said interface means when said servo control means is in upstroke mode.

38. The apparatus according to claim 24 wherein said servo control means further comprises:

means for defining an upper motion limit and a lower motion limit;

means for defining a downstroke mode, said downstroke mode designating a lift task wherein said interface means is to be moved from said upper motion limit to said lower motion limit; and means for precluding upward movement of said interface means when said servo control means is in downstroke mode.

39. The apparatus according to claim 38 wherein said servo control means further comprises:

means for defining an upstroke mode, said upstroke mode designating a lift task wherein said interface means is to be moved from said lower motion limit to said upper motion limit; and means for precluding downward movement of said interface means when said servo control means is in said upstroke mode.

40. The apparatus according to claim 24 wherein said servo control means further comprises:

means for defining an upper motion limit and a lower motion limit;

means for defining an upstroke mode and a downstroke mode;

wherein said upstroke mode designates a lift task wherein said interface means is to be moved from said lower motion limit to said upper motion limit;

wherein said downstroke mode designates a lift task wherein said interface means is to be moved from said upper motion limit to said lower motion limit;

means for simulating an upstroke weight value of said interface means during said upstroke mode;

means for simulating a downstroke weight value of said interface means during said downstroke mode; and wherein said downstroke weight value is greater than said upstroke weight value.

41. The apparatus according to claim 40 wherein said force measuring means further comprises peak force measuring means for measuring a peak force value applied to said interface means by said human subject during said upstroke mode, and wherein said servo control means simulates said downstroke weight value as a multiple of said peak force value.

42. The apparatus according to claim 40 further comprising:

means for inputting and storing an upstroke velocity limit value and a downstroke velocity limit value; and wherein said servo control means includes means for controlling the movement of said interface means so that a vertical velocity of said interface means is limited to said upstroke velocity limit value during said upstroke mode and to said downstroke velocity limit value during said downstroke mode.

43. An apparatus for performing a lift task comprising:

a horizontal arm;

interface means, having an actual mass value and being coupled to said horizontal arm for enabling a human subject to apply vertical force to said horizontal arm;

a vertical support;

carriage means, mounted on said vertical support, for carrying said horizontal arm for vertical upward and downward movement, said carriage means including hinge means for carrying said horizontal arm and for providing rotation of said horizontal arm through an angular range of motion;

wherein said horizontal arm comprises a fixed arm member mounted on said hinge means and a movable arm member mounted for translation with respect to said fixed arm member in a horizontal plane;

wherein said interface means is coupled to a free end of said movable arm member for translation therewith so that said interface means can be moved throughout a three dimensional working envelope including a horizontal working envelope component defined by the angular range of motion of said horizontal arm on said hinge means and the linear range of motion of said movable arm member relative to said fixed arm member;

transmission means, coupled to said carriage means, for driving said carriage means in said upward and downward movement;

servo motor means, coupled to said transmission means, for powering said transmission means to drive said carriage means;

servo control means, coupled to said servo motor means, for controlling the operation of said servo motor means in driving said transmission means;

load measuring means, coupled to said horizontal arm, for measuring the amount of vertical force applied to said horizontal arm and for producing an output load signal;

wherein said servo control means receives said output load signal for controlling said servo motor means for driving said transmission means as a prearranged function of a preselected lift task control mode and said output load signal;

first position tracking means for producing an output height signal to said servo control means corresponding to the vertical height of said carriage means on said vertical support;

second position tracking means for producing an output angle signal to said servo control means corresponding to the angle of said horizontal arm in said horizontal plane about said vertical support; and third position tracking means for producing an output radius signal to said servo control means corresponding to the position of said movable arm member relative to said fixed arm member; and wherein said servo control means controls the operation of said servo motor means in response to said height, angle and radius signals in a cylindrical coordinate system.

44. The apparatus according to claim 43 wherein said interface means is a box of predetermined spatial box geometry, wherein said movable arm member has a predetermined spatial arm geometry, wherein said apparatus further comprises shelf means providing a horizontal shelf adapted to support said box and having a known spatial shelf geometry and known shelf location in terms of said cylindrical coordinate system, and wherein said servo motor control means comprises:

a central processor;

converter means for converting said output load signal, said height signal, said angle signal and said radius signal from analog signal values to corresponding digital signal values for input to said central processor at a preselected data acquisition rate;

control program means for operating said central processor to produce a control command signal for driving said servo motor, said control program means including:

means for defining a safe working three dimensional envelope for said box and movable arm member as a function of said predetermined spatial box geometry, spatial arm geometry, and spatial shelf geometry and spatial shelf location within said cylindrical coordinate system;

means for assessing the current spatial position of said movable arm member and said box relative to said safe working envelope; and means for determining when said arm member and box cross the boundary of said safe working envelope and for limiting the movement of said movable arm member in a coordinate direction of said cylindrical coordinate system in response to said determination.

45. The apparatus according to claim 44 wherein said shelf means comprises:

a shelf bracket having a plurality of shelf mounting locations at various known height coordinate locations; and a shelf location sensor for signalling to said central processor at which of said shelf mounting locations a shelf has been placed.

46. The apparatus according to claim 43 wherein said interface means has a spatial interface geometry, and wherein said servo control means further comprises:

means for defining a safe working three dimensional envelope for said interface means as a function of said spatial interface geometry;

means for assessing the current spatial position of said interface means;

means for determining when said interface means crosses the boundary of said three dimensional envelope; and means for limiting the movement of said interface means to maintain the interface means within said three dimensional envelope.

47. The apparatus according to claim 46 wherein said limiting means includes means for limiting vertical movement of said interface means to maintain said interface means within said three dimensional envelope.

48. The apparatus according to claim 43 wherein said servo control means further comprises:

velocity command means, coupled to said servo motor means, for controlling said servo motor means in response to a velocity command parameter, the velocity command means including:

means for calculating a velocity change parameter as a function of said actual force and said simulated mass value;

means for calculating a new velocity command parameter as a function of a current velocity command parameter and said velocity change parameter; and means for controlling said servo motor means in response to said new velocity command parameter.

49. The apparatus according to claim 48 wherein said servo control means further comprises:

let-go detection means for detecting when said actual force is within a selected range of values for a selected time duration and for generating a let-go signal in response thereto; and wherein said velocity command means includes means for applying a safety control factor to said new velocity command parameter in response to said let-go signal so that said interface means descends at a lower velocity than originally indicated by said new velocity command parameter.

50. The apparatus according to claim 48 further comprising:

means for inputting and storing a velocity limit value;

wherein said velocity command means includes means for calculating said velocity command parameter so that a velocity of said interface means is limited to said velocity limit value.

51. The apparatus according to claim 48 wherein said servo control means further comprises:

means for defining an upper motion limit and a lower motion limit;

means for defining an upstroke mode and a downstroke mode;

wherein said upstroke mode designates a lift task wherein said interface means is to be moved from said lower motion limit to said upper motion limit;

wherein said downstroke mode designates a lift task wherein said interface means is to be moved from said upper motion limit to said lower motion limit;

means for inputting and storing an upstroke velocity limit value and a downstroke velocity limit value; and wherein said velocity command means includes means for calculating said velocity command parameter so that a velocity of said interface means is limited to said upstroke velocity limit value during said upstroke mode and to said downstroke velocity limit value during said downstroke mode.

52. The apparatus according to claim 43 wherein said servo control means further comprises:

means for defining an upper motion limit and a lower motion limit;

means for defining an upstroke mode, said upstroke mode designating a lift task wherein said interface means is to be moved from said lower motion limit to said upper motion limit; and means for precluding downward movement of said interface means when said servo control means is in upstroke mode.

53. The apparatus according to claim 43 wherein said servo control means further comprises:

means for defining an upper motion limit and a lower motion limit;

means for defining a downstroke mode, said downstroke mode designating a lift task wherein said interface means is to be moved from said upper motion limit to said lower motion limit; and means for precluding upward movement of said interface means when said servo control means is in downstroke mode.

54. The apparatus according to claim 53 wherein said servo control means further comprises:

means for defining an upstroke mode, said upstroke mode designating a lift task wherein said interface means is to be moved from said lower motion limit to said upper motion limit; and means for precluding downward movement of said interface means when said servo control means is in said upstroke mode.

55. The apparatus according to claim 43 further comprising means for setting a simulated mass value for said interface means independent of said actual mass value of said interface means, and wherein said servo control means further comprises:

means for defining an upper motion limit and a lower motion limit;

means for defining an upstroke mode and a downstroke mode;

wherein said upstroke mode designates a lift task wherein said interface means is to be moved from said lower motion limit to said upper motion limit;

wherein said downstroke mode designates a lift task wherein said interface means is to be moved from said upper motion limit to said lower motion limit;

means for simulating the inertia of an object having a mass value equal to said simulated mass value in a gravitational field during said upstroke mode; and means for simulating the inertia of an object having a mass value greater than said simulated mass value in a gravitational field during said downstroke mode.

56. The apparatus according to claim 55 wherein said load measuring means further comprises peak force measuring means for measuring a peak force value applied to said interface means by said human subject during said upstroke mode, and wherein said servo control means simulates said downstroke weight value as a multiple of said peak force value.

57. The apparatus according to claim 55 further comprising:

means for inputting and storing an upstroke velocity limit value and a downstroke velocity limit value; and wherein said servo control means includes means for controlling the movement of said interface means so that a vertical velocity of said interface means is limited to said upstroke velocity limit value during said upstroke mode and to said downstroke velocity limit value during said downstroke mode.

58. An apparatus for performing a lift task comprising:

an interface device adapted to be grasped and lifted by a human subject;

mounting means for mounting said interface device for combined movement within a range of z, r, and theta coordinates of a cylindrical coordinate system with said z coordinate having a vertical orientation;

force measuring means for measuring the amount of vertical force applied to said interface device by said human subject and for producing an output force signal;

acceleration measuring means for measuring the amount of vertical acceleration of said interface device and for producing an output acceleration signal; and movement control means, operatively associated with said mounting means and responsive to at least one of said output force signal and said output acceleration signal for controlling movement of said interface device along said z coordinate and for controlling z coordinate velocity and acceleration of said interface device in accordance with a preselected lift task function;

wherein said interface device has a spatial interface geometry, and wherein said movement control means further comprises:

means for defining a safe working three dimensional envelope for said interface device as a function of said spatial interface geometry;

means for assessing the current spatial position of said interface device;

means for determining when said interface device crosses the boundary of said three dimensional envelope; and means for limiting the movement of said interface device to maintain the interface device within said three dimensional envelope.

59. An apparatus for performing a lift task comprising:

an interface device adapted to be grasped and lifted by a human subject;

mounting means for mounting said interface device for combined movement within a range of z, r, and theta coordinates of a cylindrical coordinate system with said z coordinate having a vertical orientation;

force measuring means for measuring the amount of vertical force applied to said interface device by said human subject and for producing an output force signal;

acceleration measuring means for measuring the amount of vertical acceleration of said interface device and for producing an output acceleration signal; and movement control means, operatively associated with said mounting means and responsive to at least one of said output force signal and said output acceleration signal for controlling movement of said interface device along said z coordinate and for controlling z coordinate velocity and acceleration of said interface device in accordance with a preselected lift task function;

wherein said movement control means further comprises:

means for defining an upper motion limit and a lower motion limit;

means for defining an upstroke mode, said upstroke mode designating a lift task wherein said interface device is to be moved from said lower motion limit to said upper motion limit; and means for precluding downward movement of said interface device when said movement control means is in upstroke mode.

60. An apparatus for performing a lift task comprising:

an interface device adapted to be grasped and lifted by a human subject;

mounting means for mounting said interface device for combined movement within a range of z, r, and theta coordinates of a cylindrical coordinate system with said z coordinate having a vertical orientation;

force measuring means for measuring the amount of vertical force applied to said interface device by said human subject and for producing an output force signal;

acceleration measuring means for measuring the amount of vertical acceleration of said interface device and for producing an output acceleration signal; and movement control means, operatively associated with said mounting means and responsive to at least one of said output force signal and said output acceleration signal for controlling movement of said interface device along said z coordinate and for controlling z coordinate velocity and acceleration of said interface device in accordance with a preselected lift task function;

wherein said movement control means further comprises:

means for defining an upper motion limit and a lower motion limit;

means for defining a downstroke mode, said downstroke mode designating a lift task wherein said interface device is to be moved from said upper motion limit to said lower motion limit; and means for precluding upward movement of said interface device when said exercise control means is in downstroke mode.

61. The apparatus according to claim 60 wherein said movement control means further comprises:

means for defining an upstroke mode, said upstroke mode designating a lift task wherein said interface device is to be moved from said lower motion limit to said upper motion limit; and means for precluding downward movement of said interface device when said exercise control means is in said upstroke mode.

62. An apparatus for performing a lift task comprising:

an interface device adapted to be grasped and lifted by a human subject;

mounting means for mounting said interface device for combined movement within a range of z, r, and theta coordinates of a cylindrical coordinate system with said z coordinate having a vertical orientation;

force measuring means for measuring the amount of vertical force applied to said interface device by said human subject and for producing an output force signal;

acceleration measuring means for measuring the amount of vertical acceleration of said interface device and for producing an output acceleration signal; and movement control means, operatively associated with said mounting means and responsive to at least one of said output force signal and said output acceleration signal for controlling movement of said interface device along said z coordinate and for controlling z coordinate velocity and acceleration of said interface device in accordance with a preselected lift task function;

wherein said movement control means further comprises:

means for defining an upper motion limit and a lower motion limit;

means for defining an upstroke mode and a downstroke mode;

wherein said upstroke mode designates a lift task wherein said interface device is to be moved from said lower motion limit to said upper motion limit;

wherein said downstroke mode designates a lift task wherein said interface device is to be moved from said upper motion limit to said lower motion limit;

means for simulating an upstroke weight value of said interface device during said upstroke mode;

means for simulating a downstroke weight value of said interface device during said downstroke mode; and wherein said downstroke weight value is greater than said upstroke weight value.

63. The apparatus according to claim 62 wherein said force measuring means further comprises peak force measuring means for measuring a peak force value applied to said interface device by said human subject during said upstroke mode, and wherein said movement control means simulates said downstroke weight value as a multiple of said peak force value.

64. The apparatus according to claim 62 further comprising:

means for inputting and storing an upstroke velocity limit value and a downstroke velocity limit value; and wherein said movement control means includes means for controlling the movement of said interface device so that the z coordinate velocity of said interface device is limited to said upstroke velocity limit value during said upstroke mode and to said downstroke velocity limit value during said downstroke mode.

* * * * *